US007282519B2

(12) United States Patent
Garvey et al.

(10) Patent No.: US 7,282,519 B2
(45) Date of Patent: Oct. 16, 2007

(54) NITROSATED AND NITROSYLATED DIURETIC COMPOUNDS, COMPOSITIONS AND METHODS OF USE

(75) Inventors: David S. Garvey, Dover, MA (US); L. Gordon Letts, Dover, MA (US); Manuel Worcel, Boston, MA (US); Richard A. Earl, Westford, MA (US); Maiko Ezawa, Acton, MA (US); Xinqin Fang, Lexington, MA (US); Subhash P. Khanapure, Clinton, MA (US); Chia-En Lin, Burlington, MA (US); Ramani R. Ranatunge, Lexington, MA (US); Cheri A. Stevenson, Haverhill, MA (US)

(73) Assignee: NitroMed, Inc., Lexington, MA (US)

( * ) Notice: Subject to any disclaimer, the term of this patent is extended or adjusted under 35 U.S.C. 154(b) by 109 days.

(21) Appl. No.: 10/921,936

(22) Filed: Aug. 20, 2004

(65) Prior Publication Data

US 2005/0059655 A1 Mar. 17, 2005

Related U.S. Application Data

(60) Provisional application No. 60/535,542, filed on Jan. 12, 2004, provisional application No. 60/498,309, filed on Aug. 28, 2003.

(51) Int. Cl.
*A61K 31/34* (2006.01)
*A61K 31/44* (2006.01)
*A61K 31/497* (2006.01)
*C07D 307/52* (2006.01)

(52) U.S. Cl. .................. 514/461; 514/326; 514/254.1; 544/379; 546/207; 549/472; 558/480

(58) Field of Classification Search ............... 514/471, 514/601, 461, 326, 254.1; 549/77, 472; 568/30; 558/482, 480; 546/207; 544/379
See application file for complete search history.

(56) References Cited

U.S. PATENT DOCUMENTS

| 3,252,975 | A | 5/1966 | de Stevens et al. |
| 3,254,076 | A | 5/1966 | Lund et al. |
| 4,559,340 | A | 12/1985 | Neustadt et al. |
| 4,675,324 | A | 6/1987 | Ueda et al. |
| 4,992,451 | A | 2/1991 | Koike et al. |
| 5,773,434 | A | 6/1998 | Larson et al. |
| 6,083,947 | A | 7/2000 | Granger et al. |
| 6,166,008 | A | 12/2000 | Johnson et al. |
| 6,811,965 | B2 | 11/2004 | Vodovotz et al. |
| 6,818,647 | B2 | 11/2004 | Wolff et al. |
| 6,864,280 | B2 | 3/2005 | Igarashi et al. |
| 2004/0043987 | A1 | 3/2004 | Gouliaev et al. |
| 2004/0053974 | A1 | 3/2004 | Takaoka et al. |
| 2004/0105818 | A1 | 6/2004 | Every et al. |
| 2004/0254176 | A1 | 12/2004 | Grigorieff et al. |
| 2005/0004145 | A1 | 1/2005 | Widder et al. |
| 2005/0038017 | A1 | 2/2005 | Wolff et al. |

FOREIGN PATENT DOCUMENTS

| EP | 0598770 | 7/1992 |
| EP | 1336602 | 8/2003 |
| EP | 1595540 | 11/2005 |
| FR | 6869 | 12/1966 |
| GB | 863474 | 3/1961 |
| GB | 899037 | 6/1962 |
| GB | 1129360 | 10/1968 |
| JP | 2-180867 | 7/1990 |
| WO | WO97/26884 | 7/1997 |
| WO | WO97/49692 | 12/1997 |
| WO | WO98/09948 | 3/1998 |
| WO | WO98/12185 | 3/1998 |
| WO | WO99/21422 | 5/1999 |
| WO | WO99/42456 | 8/1999 |
| WO | WO99/67231 | 12/1999 |
| WO | WO 01/70694 A1 | 9/2001 |
| WO | WO 01/70709 A2 | 9/2001 |
| WO | WO 02/24207 A1 | 3/2002 |
| WO | WO 03/081246 A1 | 10/2003 |
| WO | WO 2004/056360 A1 | 7/2004 |
| WO | WO 2004/060375 A1 | 7/2004 |
| WO | WO 2005/014043 A1 | 2/2005 |

OTHER PUBLICATIONS

Jul. 29, 2005. International Search Report form PCT Application No. PCT/US2004/026911.

(Continued)

*Primary Examiner*—Rebecca Anderson
*Assistant Examiner*—Yong Chu
(74) *Attorney, Agent, or Firm*—Wilmer Cutler Pickering Hale and Dorr LLP

(57) ABSTRACT

The invention describes novel nitrosated and/or nitrosylated diuretic compounds or pharmaceutically acceptable salts thereof, and novel compositions comprising at least one nitrosated and/or nitrosylated diuretic compound, and, optionally, at least one nitric oxide donor and/or at least one therapeutic agent. The invention also provides novel compositions and kits comprising at least one diuretic compound of the invention, that is optionally nitrosated and/or nitrosylated, and, optionally, at least one nitric oxide donor compound and/or at least one therapeutic agent. The invention also provides methods for (a) treating conditions resulting from excessive water and/or electrolyte retention; (b) treating cardiovascular diseases; (c) treating renovascular diseases; (d) treating diabetes; (e) treating diseases resulting from oxidative stress; (f) treating endothelial dysfunctions; (g) treating diseases caused by endothelial dysfunctions; (h) treating cirrhosis; (j) treating pre-eclampsia; (k) treating osteoporosis; and (l) treating nephropathy.

6 Claims, No Drawings

OTHER PUBLICATIONS

Novello et al., J. Org. Chem., 25: 970-981 (1959).
Holdrege et al., J. Am. Chem. Soc., 4807-4810 (1959).
Whitehead et al., J. Org. Chem., 2809-2813 (1961).
Topliss et al., J. Org. Chem., 26: 3842-3850 (1961).
Werner et al., J. Am. Chem. Soc., 1161-1166 (1960).
Lund et al., Acta. Pharmacol et toxicol., 16: 297-324 (1960).
Taylor et al., J. Med & Pharm Chem., 5: 312-320 (1962).
Robertson et al., J. Med. Chem., 8: 90-95 (1965).
Shetty et al., J. Med. Chem., 13: 886-895 (1970).
Feit et al., J. Med Chem 13:1071-1075 (1970).
Hoefle et al., J. Am. Chem. Soc., 11:974-976 (1970).
Feit et al., J. Med Chem 15: 79-83 (1971).
Feit et al., J. Med Chem 16: 127-130 (1973).
Neilson et al., J. Med Chem 16: 1170-1177 (1973).
Feit et al., J. Med Chem 17: 572-578 (1974).
Nielson et al., J. Med Chem 18: 41-50 (1975).
Feit et al., J. Med Chem 19: 402-406 (1976).
Allen et al., J. Med Chem., 21: 838-840 (1978).
Feit, J. Clin. Pharmacol., 21: 531-536 (1981).
Shani et al., Pharmacology., 26: 172-180 (1983).
Woltersdorf et al., J. Med Chem 27: 840-845 (1984).
Lee et al., J. Med Chem 27: 1579-1587 (1984).
Wangemann et al., Pflugers Arch 407: (Suppl 2): S128-141 (1986).
Sakaguchi et al., Chem. Pharm. Bull., 40: 202-211 (1992).
Cotter et al., Lancet, 351: 389-393 (1998).
Costa et al., Clin. Exp. Pharmacol Physiol., 28: 528-532 (2001).
Braghiroli et al., J. Med. Chem., 45: 2355-2357 (2002).
Hernandez et al., J. Am. Col. Cardiol., 42: 709-711 (2003).
Domanski et al., J. Am. Col. Cardiol., 42: 705-708 (2003).
Carter et al., Hypertension., 43 4-9 (2004).

NITROSATED AND NITROSYLATED DIURETIC COMPOUNDS, COMPOSITIONS AND METHODS OF USE

RELATED APPLICATIONS

This application claims priority under 35 USC § 119 to U.S. Application No. 60/498,309 filed Aug. 28, 2003, and to U.S. Application No. 60/535,542 filed Jan. 12, 2004.

FIELD OF THE INVENTION

The invention describes novel nitrosated and/or nitrosylated diuretic compounds or pharmaceutically acceptable salts thereof, and novel compositions comprising at least one nitrosated and/or nitrosylated diuretic compound, and, optionally, at least one nitric oxide donor and/or at least one therapeutic agent. The invention also provides novel compositions and kits comprising at least one diuretic compound of the invention, that is optionally nitrosated and/or nitrosylated, and, optionally, at least one nitric oxide donor compound and/or at least one therapeutic agent. The invention also provides methods for (a) treating conditions resulting from excessive water and/or electrolyte retention; (b) treating cardiovascular diseases; (c) treating renovascular diseases; (d) treating diabetes; (e) treating diseases resulting from oxidative stress; (f) treating endothelial dysfunctions; (g) treating diseases caused by endothelial dysfunctions; (h) treating cirrhosis; (j) treating pre-eclampsia; (k) treating osteoporosis; and (l) treating nephropathy.

BACKGROUND OF THE INVENTION

The decline in cardiovascular morbidity and mortality in the United States over the past three decades has been the result of significant advances in research on cardiovascular disease mechanisms and therapeutic strategies. The incidence and prevalence of myocardial infarction and death from myocardial infarction, as well as that from cerebrovascular accident, have decreased significantly over this period largely owing to advances in prevention, early diagnosis, and treatment of these very common diseases.

The compounds administered for the treatment of diuresis, cardiovascular diseases, and diseases resulting from oxidative and/or endothelial dysfunctions often result in toxic, chronic and/or debilitating side effects. Cardiovascular compounds such as ACE inhibitors, beta-adrenergic blockers, antithrombotic and vasodilator compounds or anti-hyperlipidemic compounds, show, for example, respiratory toxicity resulting in asthma and/or bronchitis. Hence there is a need in the art for compounds that have improved efficacy, lower toxicity and that can be used at low dosages. The invention is directed to these, as well as other, important ends.

SUMMARY OF THE INVENTION

The invention provides novel diuretic compounds that are substituted with at least one NO and/or $NO_2$ group (i.e., nitrosylated and/or nitrosated), and pharmaceutically acceptable salts thereof. The diuretic compounds can be nitrosated and/or nitrosylated through one or more sites such as oxygen (hydroxyl condensation), sulfur (sulfhydryl condensation) and/or nitrogen. The invention also provides compositions comprising the novel compounds described herein in a pharmaceutically acceptable carrier.

The invention is also based on the discovery that administering at least one diuretic compound or a pharmaceutically acceptable salt thereof, that is optionally substituted with at least one NO and/or $NO_2$ group (i.e., nitrosylated and/or nitrosated), and, optionally, at least one nitric oxide donor compound improves the properties of the diuretic compound. Nitric oxide donors include, for example, S-nitrosothiols, nitrites, nitrates, N-oxo-N-nitrosamines, furoxans, sydnonimines, SPM 3672, SPM 5185, SPM 5186 and analogues thereof, and substrates of the various isozymes of nitric oxide synthase. Thus, another embodiment of the invention provides compositions comprising at least one diuretic compound that is optionally substituted with at least one NO and/or $NO_2$ group (i.e., nitrosylated and/or nitrosated), and at least one nitric oxide donor compound. The invention also provides for such compositions in a pharmaceutically acceptable carrier.

The invention provides compositions comprising at least one diuretic compound, that is optionally substituted with at least one NO and/or $NO_2$ group (i.e., nitrosylated and/or nitrosated), and, optionally, at least one nitric oxide donor compound and/or at least one therapeutic agent, including, but not limited to, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, anti-thrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. In a preferred embodiment the at least one therapeutic agent is selected from the group consisting of an aldosterone antagonist, an angiotensin II antagonist, an angiotensin-converting enzyme (ACE) inhibitors, a β-adrenergic antagonist, a digitalis, a diuretic, and a hydralazine compound. The invention also provides for such compositions in a pharmaceutically acceptable carrier.

Another embodiment of the invention provides compositions comprising a therapeutically effective amount of at least one diuretic compound of the invention, that is optionally substituted with at least one NO and/or $NO_2$ group (i.e., nitrosylated and/or nitrosated), and at least one therapeutic agent selected from the group consisting of an aldosterone antagonist, an angiotensin II antagonist, an angiotensin-converting enzyme (ACE) inhibitor, a β-adrenergic antagonist, a diuretic and a hydralazine compound. The invention also provides for such compositions in a pharmaceutically acceptable carrier.

The invention provides methods for (a) treating conditions resulting from excessive water and/or electrolyte retention; (b) treating cardiovascular diseases; (c) treating renovascular diseases; (d) treating diabetes; (e) treating diseases resulting from oxidative stress; (f) treating endothelial dysfunctions; (g) treating diseases caused by endothelial dysfunctions; (h) treating cirrhosis; (j) treating pre-eclampsia; (k) treating osteoporosis; and (l) treating nephropathy in a patient in need thereof comprising administering to the patient a therapeutically effective amount of at least one diuretic compound, that is optionally substituted with at least one NO and/or $NO_2$ group (i.e., nitrosylated and/or nitrosated), and, optionally, at least one therapeutic agent, such as, for example, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. The methods can optionally further comprise the administration of at least one nitric oxide donor compound. In this embodiment of the invention, the methods can involve (i) administering the nitrosated and/or nitrosylated diuretic compounds, (ii) administering the diuretic compounds, that are optionally nitrosated and/or nitrosylated, and NO donors, (iii) administering the diuretic compounds, that are optionally nitrosated and/or nitrosylated, and therapeutic agents, or (iv) administering the diuretic compounds, that are optionally nitrosated and/or nitrosylated, NO donors, and therapeutic agents. In a preferred embodiment the at least one therapeutic agent is selected from the group consisting of an aldosterone antagonist, an angiotensin II antagonist, an angiotensin-converting enzyme (ACE) inhibitor, a β-adrenergic antagonist, a diuretic, and a hydralazine compound. The diuretic compounds, nitric oxide donors, and/or therapeutic agents can be administered separately or as components of the same composition in one or more pharmaceutically acceptable carriers.

Another embodiment of the invention provides kits comprising at least one diuretic compound, that is optionally nitrosated and/or nitrosylated, and, optionally, at least one nitric oxide donor compound. The kit can further comprise at least one therapeutic agent, such as, for example, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. The diuretic compound, the nitric oxide donor and/or therapeutic agent, can be separate components in the kit or can be in the form of a composition in one or more pharmaceutically acceptable carriers.

These and other aspects of the invention are described in detail herein.

DETAILED DESCRIPTION OF THE INVENTION

As used throughout the disclosure, the following terms, unless otherwise indicated, shall be understood to have the following meanings.

"Conditions resulting from excessive water and/or electrolyte retention" include but are not limited to lower extremity swelling, fatigue, body fluid retention, cardiac enlargement, shortness of breath, pulmonary edema, cerebral edema, edema associated at least in part with a cause selected from the group consisting of congestive heart failure, cirrhosis of the liver, poor blood circulation, lymphatic system failure, chronic nephritis, malnutrition, use of birth control pills, premenstrual syndrome, sunburn, hypertension, Meniere's disease, glaucoma, cystic fibrosis and/or an imbalance of sodium and potassium, and the like.

"Cardiovascular disease or disorder" refers to any cardiovascular disease or disorder known in the art, including, but not limited to, congestive heart failure, restenosis, hypertension (e.g. pulmonary hypertension, labile hypertension, idiopathic hypertension, low-renin hypertension, salt-sensitive hypertension, low-renin, salt-sensitive hypertension, thromboembolic pulmonary hypertension; pregnancy-induced hypertension; renovascular hypertension; hypertension-dependent end-stage renal disease, hypertension associated with cardiovascular surgical procedures, hypertension with left ventricular hypertrophy, and the like), diastolic dysfunction, coronary artery disease, myocardial infarctions, cerebral infarctions, atherosclerosis, atherogenesis, cerebrovascular disease, angina, (including chronic, stable, unstable and variant (Prinzmetal) angina pectoris), aneurysm, ischemic heart disease, cerebral ischemia, myocardial ischemia, thrombosis, platelet aggregation, platelet adhesion, smooth muscle cell proliferation, vascular or non-vascular complications associated with the use of medical devices, wounds associated with the use of medical devices, vascular or non-vascular wall damage, peripheral vascular disease, neointimal hyperplasia following percutaneous transluminal coronary angiograph, vascular grafting, coronary artery bypass surgery, thromboembolic events, post-angioplasty restenosis, coronary plaque inflammation, hypercholesterolemia, embolism, stroke, shock, arrhythmia, atrial fibrillation or atrial flutter, thrombotic occlusion and reclusion cerebrovascular incidents, and the like.

"Thromboembolic events" include, but are not limited to, ischemic stroke, transient ischemic stroke, myocardial infarction, angina pectoris, thrombosis (for example, restenosis, arterial thrombosis, coronary thrombosis, heart valve thrombosis, coronary stenosis, stent thrombosis, graft thrombosis, and first and subsequent thrombotic stroke, and the like), thromboembolism (for example, pulmonary thromboembolism, cerebral thromboembolism, and the like), thrombophlebitis, thrombocytopenia, bleeding disorders, thrombotic occlusion and reocclusion and acute vascular events. Patients who are at risk of developing thromboembolic events, may include those with a familial history of, or genetically predisposed to, thromboembolic disorders, who have had ischemic stroke, transient ischemic stroke, myocardial infarction, and those with unstable angina pectoris or chronic stable angina pectoris and patients with altered prostacyclin/thromboxane $A_2$ homeostasis or higher than normal thromboxane $A_2$ levels leading to increase risk for thromboembolism, including patients with diabetes and rheumatoid arthritis.

"Diseases resulting from oxidative stress" refers to any disease that involves the generation of free radicals or radical compounds, such as, for example, atherogenesis, atheromatosis, arteriosclerosis, atherosclerosis, vascular hypertrophy associated with hypertension, hyperlipoproteinaemia, normal vascular degeneration through aging, parathyroidal reactive hyperplasia, renal disease (e.g., acute or chronic), neoplastic diseases, inflammatory diseases, neurological and acute bronchopulmonary disease, tumorigenesis, ischemia-reperfusion syndrome, arthritis, sepsis, cognitive dysfunction, endotoxic shock, endotoxin-induced organ failure, and the like.

"Renovascular diseases" refers to any disease or dysfunction of the renal system including, but not limited to, renal failure (e.g., acute or chronic), renal insufficiency, nephrotic edema, acute glomerulonephritis, oliguric renal failure, renal deterioration associated with severe hypertension, unilateral perechymal renal disease, polycystic kidney disease, chronic pyelonephritis, renal diseases associated with renal insufficiency, complications associated with dialysis or renal transplantation, renovascular hypertension, nephropathy, glomerulonephritis, scleroderma, glomerular sclerosis, and the like "Endothelial dysfunction" refers to the impaired ability of in any physiological processes carried out by the endothelium, in particular, production of nitric oxide regardless of cause. It may be evaluated by, such as, for example, invasive techniques, such as, for example, coronary artery reactivity to acetylcholine or methacholine, and the like, or by non-invasive techniques, such as, for example, blood flow measurements, brachial artery flow dilation using cuff occlusion of the arm above or below the elbow, brachial artery ultrasonography, imaging techniques, measurement of circulating biomarkers, such as, asymmetric dimethylarginine (ADMA), and the like. For the latter measurement the endothelial-dependent flow-mediated dialation will be lower in patients diagnosed with an endothelial dysfunction.

"Methods for treating endothelial dysfunction" include, but are not limited to, treatment prior to the onset/diagnosis of a disease that is caused by or could result from endothelial dysfunction, such as, for example, atherosclerosis, hypertension, diabetes, congestive heart failure, and the like.

"Methods for treating diseases caused by endothelial dysfunction" include, but are not limited to, the treatment of any disease resulting from the dysfunction of the endothelium, such as, for example, arteriosclerosis, congestive heart failure, hypertension, cardiovascular diseases, cerebrovascular diseases, renovascular diseases, mesenteric vascular diseases, pulmonary vascular diseases, ocular vascular diseases, peripheral vascular diseases, peripheral ischemic diseases, and the like.

"Therapeutic agent" includes any therapeutic agent that can be used to treat or prevent the diseases described herein. "Therapeutic agents" include, for example, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and the like. Therapeutic agent includes the pharmaceutically acceptable salts thereof, prodrugs, and pharmaceutical derivatives thereof including, but not limited to, the corresponding nitrosated and/or nitrosylated derivatives. Although nitric oxide donors have therapeutic activity, the term "therapeutic agent" does not include the nitric oxide donors described herein, since nitric oxide donors are separately defined.

"Prodrug" refers to a compound that is made more active in vivo.

"Antioxidant" refers to and includes any compound that can react and quench a free radical.

"Angiotensin converting enzyme (ACE) inhibitor" refers to compounds that inhibit an enzyme which catalyzes the conversion of angiotensin I to angiotensin II. ACE inhibitors include, but are not limited to, amino acids and derivatives thereof, peptides, including di- and tri-peptides, and antibodies to ACE which intervene in the renin-angiotensin system by inhibiting the activity of ACE thereby reducing or eliminating the formation of the pressor substance angiotensin II.

"Angiotensin II antagonists" refers to compounds which interfere with the function, synthesis or catabolism of angiotensin II. Angiotensin II antagonists include peptide compounds and non-peptide compounds, including, but not limited to, angiotensin II antagonists, angiotensin II receptor antagonists, agents that activate the catabolism of angiotensin II, and agents that prevent the synthesis of angiotensin I from angiotensin II. The renin-angiotensin system is involved in the regulation of hemodynamics and water and electrolyte balance. Factors that lower blood volume, renal perfusion pressure, or the concentration of sodium in plasma tend to activate the system, while factors that increase these parameters tend to suppress its function.

"Anti-hyperlipidemic compounds" refers to any compound or agent that has the effect of beneficially modifying serum cholesterol levels such as, for example, lowering serum low density lipoprotein (LDL) cholesterol levels, or inhibiting oxidation of LDL cholesterol, whereas high density lipoprotein (HDL) serum cholesterol levels may be lowered, remain the same, or be increased. Preferably, the anti-hyperlipidemic compound brings the serum levels of LDL cholesterol and HDL cholesterol (and, more preferably, triglyceride levels) to normal or nearly normal levels.

"Diuretic compound" refers to and includes any compound or agent that increases the amount of urine excreted by a patient.

"Neutral endopeptidase inhibitors" refers to and includes compounds that are antagonists of the renin angiotensin aldosterone system including compounds that are dual inhibitors of neutral endopeptidases and angiotensin converting (ACE) enzymes.

"Renin inhibitors" refers to compounds which interfere with the activity of renin.

"Phosphodiesterase inhibitor" or "PDE inhibitor" refers to any compound that inhibits the enzyme phosphodiesterase. The term refers to selective or non-selective inhibitors of cyclic guanosine 3',5'-monophosphate phosphodiesterases (cGMP-PDE) and cyclic adenosine 3',5'-monophosphate phosphodiesterases (cAMP-PDE).

"Platelet reducing agents" refers to compounds that prevent the formation of a blood thrombus via any number of potential mechanisms. Platelet reducing agents include, but are not limited to, fibrinolytic agents, anti-coagulant agents and any inhibitors of platelet function. Inhibitors of platelet function include agents that impair the ability of mature platelets to perform their normal physiological roles (i.e., their normal function, such as, for example, adhesion to cellular and non-cellular entities, aggregation, release of factors such as growth factors) and the like.

"Proton pump inhibitor" refers to any compound that reversibly or irreversibly blocks gastric acid secretion by inhibiting the $H^+/K^+$-ATP ase enzyme system at the secretory surface of the gastric parietal cell.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Cyclooxygenase-2 (COX-2) selective inhibitor" refers to a compound that selectively inhibits the cyclooxygenase-2 enzyme over the cyclooxygenase-1 enzyme. In one embodiment, the compound has a cyclooxygenase-2 $IC_{50}$ of less than about 2 μM and a cyclooxygenase-1 $IC_{50}$ of greater than about 5 μM, in the human whole blood COX-2 assay (as described in Brideau et al., *Inflamm Res.*, 45: 68-74 (1996)) and also has a selectivity ratio of cyclooxygenase-2 inhibition over cyclooxygenase-1 inhibition of at least 10, and preferably of at least 40. In another embodiment, the compound has a cyclooxygenase-1 $IC_{50}$ of greater than about 1 μM, and preferably of greater than 20 μM. The compound can also inhibit the enzyme, lipoxygenase. Such selectivity may indicate an ability to reduce the incidence of common NSAID-induced side effects.

"Patient" refers to animals, preferably mammals, most preferably humans, and includes males and females, and children and adults.

"Therapeutically effective amount" refers to the amount of the compound and/or composition that is effective to achieve its intended purpose.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Sustained release" refers to the release of a therapeutically active compound and/or composition such that the blood levels of the therapeutically active compound are maintained within a desirable therapeutic range over a period of time. The sustained release formulation can be prepared using any conventional method known to one skilled in the art to obtain the desired release characteristics.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, NO•), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, $NO^-$, NO•), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo and/or are oxidized to produce nitric oxide and/or are substrates for nitric oxide synthase and/or cytochrome P450. "NO donor" also includes compounds that are precursors of L-arginine, inhibitors of the enzyme arginase and nitric oxide mediators.

"Alkyl" refers to a lower alkyl group, a substituted lower alkyl group, a haloalkyl group, a hydroxyalkyl group, an alkenyl group, a substituted alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicalkyl group.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Substituted lower alkyl" refers to a lower alkyl group, as defined herein, wherein one or more of the hydrogen atoms have been replaced with one or more $R^{100}$ groups, wherein each $R^{100}$ is independently a hydroxy, an ester, an amidyl, an oxo, a carboxyl, a carboxamido, a halo, a cyano, a nitrate or an amino group, as defined herein.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$-$C_{10}$ hydrocarbon (preferably a $C_2$-$C_8$ hydrocarbon, more preferably a $C_2$-$C_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" refers to a branched or straight chain $C_2$-$C_4$ hydrocarbon that can comprise one or two carbon-carbon double bonds.

"Substituted alkenyl" refers to a branched or straight chain $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein. "Alkynyl" refers to an unsaturated acyclic $C_2$-$C_{10}$ hydrocarbon (preferably a $C_2$-$C_8$ hydrocarbon, more preferably a $C_2$-$C_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0)octane, 7-oxabicyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamide nitrate and nitro. Exemplary heterocyclic groups include pyrrolyl, furyl, thienyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrahydrofuranyl, tetrazolyl, pyrrolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, benzothiazolinyl, quinolinyl, 2,6-dioxabicyclo(3.3.0) octane, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" refers to an unsaturated cyclic $C_2$-$C_{10}$ hydrocarbon (preferably a $C_2$-$C_8$ hydrocarbon, more preferably a $C_2$-$C_6$ hydrocarbon) which can comprise one or more carbon-carbon triple bonds.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Arylalkenyl" refers to an aryl radical, as defined herein, attached to an alkenyl radical, as defined herein. Exemplary arylalkenyl groups include styryl, propenylphenyl, and the like.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetrahydroquinoline, and the like.

"Alkylheterocyclic ring" refers to a heterocyclic ring radical, as defined herein, attached to an alkyl radical, as defined herein. Exemplary alkylheterocyclic rings include 2-pyridylmethyl, 1-methylpiperidin-2-one-3-methyl, and the like.

"Alkoxy" refers to $R_{50}O$—, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Aryloxy" refers to $R_{55}O$—, wherein $R_{55}$ is an aryl group, as defined herein. Exemplary arylkoxy groups include napthyloxy, quinolyloxy, isoquinolizinyloxy, and the like.

"Alkylthio" refers to $R_{50}S$—, wherein $R_{50}$ is an alkyl group, as defined herein.

"Lower alkylthio" refers to a lower alkyl group, as defined herein, appended to a thio group, as defined herein.

"Arylalkoxy" or "alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Arylalklythio" or refers to an alkylthio group, as defined herein, to which is appended an aryl group, as defined herein. Exemplary arylalklythio groups include benzylthio, phenylethylthio, chlorophenylethylthio, and the like.

"Arylalklythioalkyl" or refers to an arylalkylthio group, as defined herein, to which is appended an alkyl group, as defined herein. Exemplary arylalklythioalkyl groups include benzylthiomethyl, phenylethylthiomethyl, chlorophenylethylthioethyl, and the like.

"Alkylthioalkyl" or refers to an alkylthio group, as defined herein, to which is appended an alkyl group, as defined herein. Exemplary alkylthioalkyl groups include allylthiomethyl, ethylthiomethyl, trifluoroethylthiomethyl, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" refers to $R_{54}S$—, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy, 2-bromobutoxy, and the like.

"Hydroxy" refers to —OH.

"Oxy" refers to —O—

"Oxo" refers to =O.

"Oxylate" refers to —O$^-$R$_{77}$$^+$ wherein $R_{77}$ is an organic or inorganic cation.

"Thiol" refers to —SH.

"Thio" refers to —S—.

"Oxime" refers to =N—OR$_{81}$ wherein $R_{81}$ is a hydrogen, an alkyl group, an aryl group, an alkylsulfonyl group, an arylsulfonyl group, a carboxylic ester, an alkylcarbonyl group, an arylcarbonyl group, a carboxamido group, an alkoxyalkyl group or an alkoxyaryl group.

"Hydrazone refers to =N—N($R_{81}$)(R'$_{81}$) wherein R'$_{81}$ is independently selected from $R_{81}$, and $R_{81}$ is as defined herein.

"Hydrazino" refers to $H_2N$—N(H)—.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, magnesium, calcium, and the like.

"Hydroxyalkyl" refers to a hydroxy group, as defined herein, appended to an alkyl group, as defined herein.

"Nitrate" refers to —O—NO$_2$.

"Nitrite" refers to —O—NO.

"Thionitrate" refers to —S—NO$_2$.

"Thionitrite" and "nitrosothiol" refer to —S—NO.

"Nitro" refers to the group —NO$_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Amino" refers to —NH$_2$, an alkylamino group, a dialkylamino group, an arylamino group, a diarylamino group, an alkylarylamino group or a heterocyclic ring, as defined herein.

"Alkylamino" refers to $R_{50}$NH—, wherein $R_{50}$ is an alkyl group, as defined herein. Exemplary alkylamino groups include methylamino, ethylamino, butylamino, cyclohexylamino, and the like.

"Arylamino" refers to $R_{55}$NH—, wherein $R_{55}$ is an aryl group, as defined herein.

"Dialkylamino" refers to $R_{52}R_{53}$N—, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}$N—, wherein $R_{55}$ and $R_{60}$ are each independently an aryl group, as defined herein.

"Alkylarylamino or arylalkylamino" refers to $R_{52}R_{55}$N—, wherein $R_{52}$ is an alkyl group, as defined herein, and $R_{55}$ is an aryl group, as defined herein.

"Alkylarylalkylamino" refers to $R_{52}R_{79}$N—, wherein $R_{52}$ is an alkyl group, as defined herein, and $R_{79}$ is an arylalkyl group, as defined herein.

"Alkylcycloalkylamino" refers to $R_{52}R_{80}$N—, wherein $R_{52}$ is an alkyl group, as defined herein, and $R_{80}$ is an cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" refers to an aryl group to which is appended an alkylamino group, a arylamino group or an arylalkylamino group. Exemplary aminoaryl groups include anilino, N-methylanilino, N-benzylanilino, and the like.

"Thio" refers to —S—.

"Sulfinyl" refers to —S(O)—.

"Methanthial" refers to —C(S)—.

"Thial" refers to =S.

"Sulfonyl" refers to —S(O)$_2$$^-$.

"Sulfonic acid" refers to —S(O)$_2$OR$_{76}$, wherein $R_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to a sulfonic acid group, as defined herein, appended to an aryl group, as defined herein "Sulfonic ester" refers to —S(O)$_2$OR$_{58}$, wherein $R_{58}$ is an alkyl group, an aryl group, or an aryl heterocyclic ring, as defined herein.

"Sulfonamido" refers to —S(O)$_2$—N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}$S—, wherein $R_{50}$ is an alkyl group, as defined herein (preferably a lower alkyl group, as defined herein).

"Arylthio" refers to $R_{55}$S—, wherein $R_{55}$ is an aryl group, as defined herein.

"Arylalkylthio" refers to an aryl group, as defined herein, appended to an alkylthio group, as defined herein.

"Alkylsulfinyl" refers to $R_{50}$—S(O)—, wherein $R_{50}$ is an alkyl group, as defined herein.

"Alkylsulfonyl" refers to $R_{50}$—S(O)$_2$—, wherein $R_{50}$ is an alkyl group, as defined herein.

"Alkylsulfonyloxy" refers to $R_{50}$—S(O)$_2$—O—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—S(O)$_2$—, wherein $R_{55}$ is an aryl group, as defined herein.

"Arylsulfonyloxy" refers to $R_{55}$—S(O)$_2$—O—, wherein $R_{55}$ is an aryl group, as defined herein.

"Amidyl" refers to $R_{51}$C(O)N($R_{57}$)— wherein $R_{51}$ and $R_{57}$ are each independently a hydrogen atom, an alkyl group, an aryl group or an arylheterocyclic ring, as defined herein.

"Ester" refers to $R_{51}C(O)R_{76}$— wherein $R_{51}$ is a hydrogen atom, an alkyl group, an aryl group or an arylheterocyclic ring, as defined herein and $R_{76}$ is oxygen or sulfur.

"Carbamoyl" refers to —O—C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)O$R_{76}$, wherein $R_{76}$ is a hydrogen, an organic cation or an inorganic cation, as defined herein.

"Carbonyl" refers to —C(O)—.

"Alkylcarbonyl" refers to $R_{52}$—C(O)—, wherein $R_{52}$ is an alkyl group, as defined herein.

"Arylcarbonyl" refers to $R_{55}$—C(O)—, wherein $R_{55}$ is an aryl group, as defined herein.

"Arylalkylcarbonyl" refers to $R_{55}$—$R_{52}$—C(O)—, wherein $R_{55}$ is an aryl group, as defined herein, and $R_{52}$ is an alkyl group, as defined herein.

"Alkylarylcarbonyl" refers to $R_{52}$—$R_{55}$—C(O)—, wherein $R_{55}$ is an aryl group, as defined herein, and $R_{52}$ is an alkyl group, as defined herein.

"Heterocyclicalkylcarbonyl" refer to $R_{78}$C(O)— wherein $R_{78}$ is a heterocyclicalkyl group, as defined herein.

"Carboxylic ester" refers to —C(O)O$R_{58}$, wherein $R_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Alkyl ester" refers to an alkyl group, as defined herein, appended to an ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Aryl ester" refers to an aryl group, as defined herein, appended to an ester group, as defined herein.

"Carboxamido" refers to —C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{59}$)—C(O)N($R_{51}$)($R_{57}$) wherein $R_{51}$, $R_{57}$, and $R_{59}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Phosphoryl" refers to —P($R_{70}$)($R_{71}$)($R_{72}$), wherein $R_{70}$ is a lone pair of electrons, thial or oxo, and $R_{71}$ and $R_{72}$ are each independently a covalent bond, a hydrogen, a lower alkyl, an alkoxy, an alkylamino, a hydroxy, an oxy or an aryl, as defined herein.

"Silyl" refers to —Si($R_{73}$)($R_{74}$)($R_{75}$), wherein $R_{73}$, $R_{74}$ and $R_{75}$ are each independently a covalent bond, a lower alkyl, an alkoxy, an aryl or an arylalkoxy, as defined herein.

The compounds and compositions of the invention are diuretics, including, but are not limited to, thiazides (such as, for example, althiazide, bendroflumethiazide, benzclortriazide, benzhydrochlorothiazide, benzthiazide, buthiazide, chlorothiazide, cyclopenethiazide, cyclothiazide, epithiazide, ethiazide, hydrobenzthiazide, hydrochlorothiazide, hydroflumethiazide, methylclothiazide, methylcyclothiazide, penflutazide, polythiazide, teclothiazide, trichlormethiazide, triflumethazide, and the like); alilusem, ambuside, amiloride, aminometradine, azosemide, bemetizide, bumetanide, butazolamide, butizide, canrenone, carperitide, chloraminophenamide, chlorazanil, chlormerodrin, chlorthalidone, cicletanide, clofenamide, clopamide, clorexolone, conivaptan, daglutril, dichlorophenamide, disulfamide, ethacrynic acid, ethoxzolamide, etozolon, fenoldopam, fenquizone, furosemide, indapamide, mebutizide, mefruside, meralluride, mercaptomerin sodium, mercumallylic acid, mersalyl, methazolamide, meticane, metolazone, mozavaptan, muzolimine, N-(5-1,3,4-thiadiazol-2-yl) acetamide, nesiritide, pamabrom, paraflutizide, piretanide, protheobromine, quinethazone, scoparius, spironolactone, theobromine, ticrynafen, torsemide, torvaptan, triamterene, tripamide, ularitide, xipamide or potassium, AT 189000, AY 31906, BG 9928, BG 9791, C 2921, DTI 0017, JDL 961, KW 3902, MCC 134, SLV 306, SR 121463, WAY 140288, ZP 120, and the like. The contemplated diuretic compounds are described more fully in the literature, such as in Goodman and Gilman, The Pharmacological Basis of Therapeutics (9th Edition), McGraw-Hill, (1996); Merck Index on CD-ROM, 13$^{th}$ Edition; STN Express, file phar and file registry, the disclosures of each of which are incorporated by reference herein in their entirety.

The diuretic compounds are nitrosated and/or nitrosylated through one or more sites such as oxygen (hydroxyl condensation), sulfur (sulfhydryl condensation) and/or nitrogen. The diuretic compounds that are nitrosated and/or nitrosylated in accordance with the invention and/or are included in the compositions of the invention can be any of those known in the art, including those exemplified below.

In another embodiment, the invention described nitrosated and/or nitrosylated diuretic compounds of Formula (I) and pharmaceutically acceptable salts thereof:

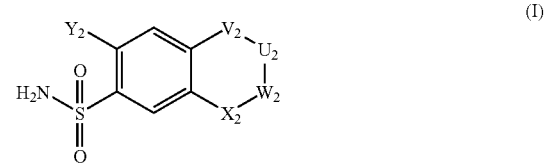

(I)

wherein:

$X_2$ is —C(O)— or —S(O)$_2$;

$Y_2$ is a hydrogen, chlorine or CF$_3$;

—$V_2$—$U_2$—$W_2$— is:

(i) —N(D$_1$)—(C(R$_o$)(R$_p$))—N(D$_1$)—;

(ii) —N=C(R$_o$))—N(D$_1$)—; or (iii) —N(D$_1$)—(C(R$_o$)(R$_p$))—N(R$_o$)—;

$R_o$ and $R_p$ at each occurrence are independently a hydrogen, a lower alkyl group, a substituted alkyl group, a benzyl group, an aryl group, an alkylaryl group, —CH$_2$—S—CH—CH=CH$_2$; —CH$_2$—S—CF$_3$ or —CH$_2$—S—CH$_2$—C$_6$H$_5$;

$D_1$ is a hydrogen, $V_3$ or K;

K is $-(W_3)_a-E_b-(C(R_e)(R_f))_{p1}-E_c-(C(R_e)(R_f))_x-(W_3)_d-(C(R_e)(R_f))_y-(W_3)_i-E_j-(W_3)_g-(C(R_e)(R_f))_z-U_3-V_3$;

$V_3$ is $-NO$ or $-NO_2$;

a, b, c, d, g, i and j are each independently an integer from 0 to 3;

$p_1$, x, y and z are each independently an integer from 0 to 10;

$W_3$ at each occurrence is independently $-C(O)-$, $-C(S)-$, $-T_3-$, $-(C(R_e)(R_f))_h-$, an alkyl group, an aryl group, a heterocyclic ring, an arylheterocyclic ring, or $-(CH_2CH_2O)_{q1}-$;

E at each occurrence is independently $-T_3-$, an alkyl group, an aryl group, $-(C(R_e)(R_f))_h-$, a heterocyclic ring, an arylheterocyclic ring, or $-(CH_2CH_2O)_{q1}-$;

$T_3$ at each occurrence is independently a covalent bond, a carbonyl, an oxygen, $-S(O)_o-$ or $-N(R_a)R_i$;

h is an integer form 1 to 10;

$q_1$ is an integer from 1 to 5;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, K or $R_e$ and $R_f$ taken together with the carbons to which they are attached form a carbonyl, a methanthial, a heterocyclic ring, a cycloalkyl group, an aryl group, an oxime, a hydrazone or a bridged cycloalkyl group;

$U_3$ at each occurrence is independently an oxygen, $-S(O)_o-$ or $-N(R_a)R_i$;

o is an integer from 0 to 2;

$R_a$ is a lone pair of electrons, a hydrogen or an alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, arylsulphonyloxy, a sulfonamido, a carboxamido, a carboxylic ester, an aminoalkyl, an aminoaryl, $-CH_2-C(U_3-V_3)(R_e)(R_f)$, a bond to an adjacent atom creating a double bond to that atom, $-(N_2O_2-)^-\cdot M_1^+$, wherein $M_1^+$ is an organic or inorganic cation; and with the proviso that the nitrosated and/or nitrosylated diuretic compounds of Formula (I) must contain at least one NO group, and/or at least one $NO_2$ group; wherein the at least one NO group and/or the at least one $NO_2$ group is linked to the diuretic compound through an oxygen atom, a nitrogen atom or a sulfur atom.

In cases where multiple designations of variables which reside in sequence are chosen as a "covalent bond" or the integer chosen is 0, the intent is to denote a single covalent bond connecting one radical to another. For example, $E_0$ would denote a covalent bond, while $E_2$ denotes (E-E) and $(C(R_4)(R_4))_2$ denotes $-C(R_4)(R_4)-C(R_4)(R_4)-$.

Another embodiment of the invention describes nitrosated and/or nitrosylated diuretic compounds of Formula (II) and pharmaceutically acceptable salts thereof:

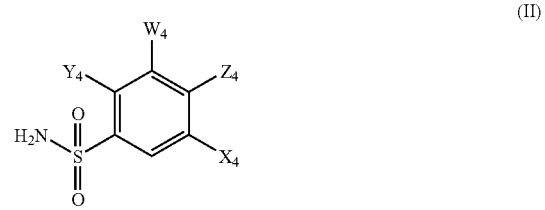

(II)

wherein:

$X_4$ is:

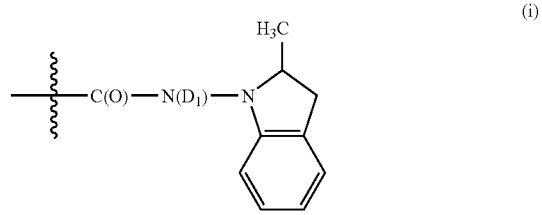

(i)

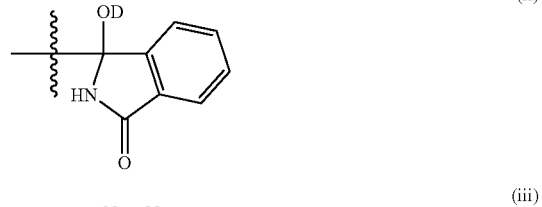

(ii)

(iii)

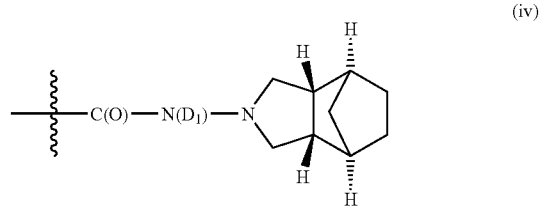

(iv)

(v)

(vi)

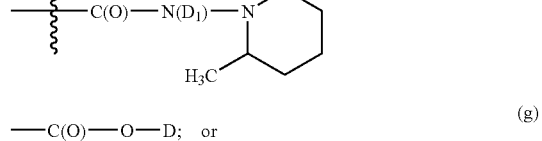

$-C(O)-O-D$; or (g)

-continued (h)

[structure: wavy bond—O—phenyl]

$Z_4$ is:

(i) a hydrogen;

(ii) [structure: wavy bonds—N(D$_1$)CH$_2$—furan/thiophene ring labeled V$_4$]

(iii) —N=C(H)—C(H)=C(OD)(CH$_3$);

(iv) —S(O)$_2$—N(D$_1$)—CH$_2$—CH=CH$_2$;

(v) —NH(D$_1$);

(vi) —CH$_3$; or (vii) —OD$_1$ $Y_4$ is:

(i) $Y_2$; or (ii) [structure: wavy bonds—O—phenyl];

$W_4$ is:

(i) a hydrogen;

(ii) [structure: wavy bonds—N-pyrrolidine ring]; or (iii) —N(D$_1$)—(CH$_2$)$_3$—CH$_3$;

D is $V_3$ or K;

$V_4$ is a thio group or an oxygen atom; and $D_1$, $Y_2$, $V_3$ and K are as defined herein; and with the proviso that the nitrosated and/or nitrosylated diuretic compounds of Formula (II) must contain at least one NO group, and/or at least one NO$_2$ group; wherein the at least one NO group and/or the at least one NO$_2$ group is linked to the diuretic compound through an oxygen atom, a nitrogen atom or a sulfur atom.

Another embodiment of the invention describes nitrosated and/or nitrosylated diuretic compounds of Formula (III) and pharmaceutically acceptable salts thereof:

(III)

[structure: dichlorobenzene with C(=O)X$_3$ and O—CH$_2$—C(=O)—K substituents]

wherein:

$X_3$ is:

(i) [structure: thiophene-2-yl with wavy bond]; or (ii) [structure: H$_3$C—CH$_2$—C(=CH$_2$)— with wavy bonds, methyl branch];

K is as defined herein; and with the proviso that the nitrosated and/or nitrosylated diuretic compounds of Formula (II) must contain at least one NO group, and/or at least one NO$_2$ group; wherein the at least one NO group and/or the at least one NO$_2$ group is linked to the diuretic compound through an oxygen atom, a nitrogen atom or a sulfur atom.

In another embodiment of the invention, the nitrosated and/or nitrosylated diuretic compounds of the invention do not include the compounds disclosed in EP 1,336,602; the disclosure of which is incorporated by reference herein in its entirety.

In another embodiment, the invention describes nitrosated and/or nitrosylated diuretic compounds of the invention and pharmaceutically acceptable salts thereof. In one embodiment, the pharmaceutically acceptable salts do not include the nitrate salt.

In other embodiments of the invention the compound of Formula (I) is a nitrosated althiazide, a nitrosylated althiazide, a nitrosated and nitrosylated althiazide, a nitrosated bendroflumethiazide, a nitrosylated bendroflumethiazide, a nitrosated and nitrosylated bendroflumethiazide, a nitrosated benzthiazide, a nitrosylated benzthiazide, a nitrosated and nitrosylated benzthiazide, a nitrosated buthiazide, a nitrosylated buthiazide, a nitrosated and nitrosylated buthiazide, a nitrosated chlorothiazide, a nitrosylated chlorothiazide, a nitrosated and nitrosylated chlorothiazide, a nitrosated cyclothiazide, a nitrosylated cyclothiazide, a nitrosated and nitrosylated cyclothiazide, a nitrosated ethiazide, a nitrosylated ethiazide, a nitrosated and nitrosylated ethiazide, a nitrosated fenquizone, a nitrosylated fenquizone, a nitrosated and nitrosylated fenquizone, a nitrosated hydrochlorothiazide, a nitrosylated hydrochlorothiazide, a nitrosated and nitrosylated hydrochlorothiazide, a nitrosated methyclothiazide, a nitrosylated methyclothiazide, a nitrosated and nitrosylated methyclothiazide, a nitrosated metolazone, a nitrosylated metolazone, a nitrosated and nitrosylated metolazone, a nitrosated paraflutizide, a nitrosylated paraflutizide, a nitrosated and nitrosylated paraflutizide, a nitrosated polythiazide, a nitrosylated polythiazide, a nitrosated and nitrosylated polythiazide, a nitrosated quinethazone, a nitrosylated quinethazone, a nitrosated and nitrosylated quinethazone, a nitrosated teclothiazide, a nitrosylated teclothiazide, a nitrosated and nitrosylated teclothiazide, a nitrosated trichlormethiazide, a nitrosylated trichlormethiazide, a nitrosated and nitrosylated trichlormethiazide; the compound of Formula (II) is a nitrosated ambuside, a nitrosylated ambuside, a nitrosated and nitrosylated ambuside, a nitrosated azosemide, a nitrosylated azosemide, a nitrosated and nitrosylated azosemide, a nitrosated bumetanide, a nitrosylated bumetanide, a nitrosated and nitrosylated bumetanide, a nitrosated chloraminophenamide, a nitrosylated chloraminophenamide, a nitrosated and nitrosylated chloraminophenamide, a nitrosated chlorthalidone, a nitrosylated chlorthalidone, a nitrosated and nitrosylated chlorthalidone, a nitrosated clofenamide, a nitrosylated clofenamide, a nitrosated and nitrosylated clofenamide, a nitrosated clopamide, a nitrosylated clopamide, a nitrosated and nitrosylated clopamide, a nitrosated disulfamide, a nitrosylated disulfamide, a nitrosated and nitrosylated disulfamide, a nitrosated furosemide, a nitrosylated furosemide, a nitrosated and nitrosylated furosemide, a nitrosated mefruside, a nitrosylated mefruside, a nitrosated and nitrosylated mefruside, a nitrosated piretanide, a nitrosylated piretanide, a nitrosated and nitrosylated piretanide, a nitrosated xipamide, a nitrosylated xipamide, a nitrosated and nitrosylated xipamide; the compound of Formula (III) is a nitrosated ethacrynic acid, a nitrosylated ethacrynic acid, a nitrosated and nitrosylated ethacrynic acid, a nitrosated ticrynafen, a nitrosylated ticrynafen, a nitrosated and nitrosylated ticrynafen, and pharmaceutically acceptable salts thereof.

In one embodiment of the invention for the compounds of Formula (I), (II) or (III) and pharmaceutically acceptable salts thereof, K is:

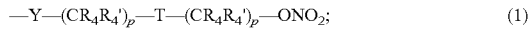  (1)

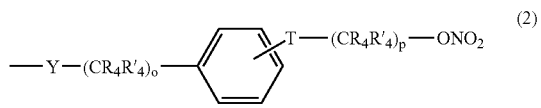  (2)

wherein T is ortho, meta or para;

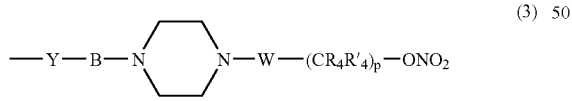  (3)

—Y—(CR₄C₄')ₚ—V—B—T—(CR₄R₄')ₚ—ONO₂;  (4)

—Y—(CR₄R₄')ₚ—T—C(O)—(CR₄R₄')ₒ—(CH₂)—ONO₂;  (5)

—Y—(CR₄R₄')ₚ—C(Z)—(CH₂)_q—T—(CR₄R₄')_q—(CH₂)—ONO₂;  (6)

—Y—(CR₄R₄')ₚ—T—(CH₂)_q—V—(CR₄R₄')_q—(CH₂)—ONO₂;  (7)

—Y—(CR₄R₄')ₚ—V—(CH₂)_q—V—(CR₄R₄')_q—(CH₂)—ONO₂;  (8)

—Y—(CR₄R₄')ₒ—(W)_q—(CR₄R₄')ₒ—(CH₂)—ONO₂;  (9)

—NR_f—O—(CH₂)ₒ—V—(CR₄R₄')_q—(CH₂)—ONO₂;  (10)

—NR_f—O—(CH₂)ₒ—(W)_q—(CR₄R₄')_q—(CH₂)—ONO₂;  (11)

—O—NR_f—(CH₂)ₒ—(W)_q—(CR₄R₄')_q—(CH₂)—ONO₂;  (12)

—Y—(CH₂)ₒ—(W)_q—(CH₂)ₒ—V—(CR₄R₄')ₒ—Q'—(CR₄R₄')ₒ—(CH₂)—ONO₂;  (13)

—Y—(CR₄R₄')ₚ—V—(CH₂)ₒ—(W)_q—(CR₄R₄')_q—(CH₂)—ONO₂;  (14)

—O—NR_f—(CH₂)ₒ—V—(CR₄R₄')_q—(CH₂)—ONO₂;  (15)

—Y—(CR₄R₄')ₒ—Q'—(CR₄R₄')ₒ—V—(CR₄R₄')ₒ—(CH₂)—ONO₂;  (16)

—Y—(CR₄R₄')ₒ—Q'—(CR₄R₄')ₒ—(W)_q—(CR₄R₄')ₒ—(CH₂)—ONO₂;  (17)

—Y—(CR₄R₄')ₚ—T—(CR₄R₄')ₚ—Q'—(CR₄R₄')ₒ—(CH₂)—ONO₂;  (18)

—Y—(CR₄R₄')_q—C(Z)—(CR₄R₄')ₒ—(CH₂)—ONO₂;  (19)

—Y—(CR₄R₄')ₚ—Q'—(CR₄R₄')ₒ—(CH₂)—ONO₂;  (20)

—Y—(CR₄R₄')_q—P(O)MM';  (21)

—Y—(CR₄R₄')ₒ—Q'—(CR₄R₄')ₒ—(CH₂)—ONO₂;  (22)

—Y—(CR₄R₄')ₒ—Q'—(CR₄R₄')ₒ—T—(CR₄R₄')ₒ—(CH₂)—ONO₂;  (23)

—Y—(CR₄R₄')_q—(W)_q—(CR₄R₄')ₒ—Q'—(CR₄R₄')ₒ—(CH₂)—ONO₂;  (24)

—Y—(CR₄R₄')_q—V—(CR₄R₄')ₒ—Q'—(CR₄R₄')ₒ—(CH₂)—ONO₂;  (25)

—Y—(CR₄R₄')ₚ—(T)ₒ—(W)_q—(CR₄R₄')ₒ—(CH₂)—ONO₂;  (26)

—Y—(CR₄R₄')ₚ—(W)_q—(T)ₒ—(CR₄R₄')ₒ—(CH₂)—ONO₂;  (27)

—Y—(CR₄R₄')_q—C(Z)—V—(CR₄R₄')_q—(CH₂)—ONO₂;  (28)

—Y—(CR₄R₄')ₒ—C(R₄)(ONO₂)—(CR₄R₄')_q—(T)ₒ—(W)_q—(T)ₒ—(CR₄R₄')ₒ—R₅;  (29)

—Y—(CR₄R₄')ₒ—V—(CR₄R₄')ₒ—Q'—(CR₄R₄')ₒ—(CH₂)—ONO₂;  (30)

—Y—(CR₄R₄')_q—C(Z)—Q'—(CR₄R₄')ₒ—(CH₂)—ONO₂;  (31)

—Y—(CR₄R₄')ₚ—V—(CR₄R₄')ₚ—(CH₂)—ONO₂;  (32)

—Y—(CR₄R₄')ₚ—V—(CH₂)_q—(T)ₒ—(CR₄R₄')_q—(CH₂)—ONO₂;  (33)

—Y—(CR₄R₄')ₚ—(T)ₒ—Q'—(T)ₒ—(CR₄R₄')_q—(CH₂)—ONO₂;  (34)

—Y—(CR₄R₄')_q—C(Z)—(CR₄R₄')_q—V—(CR₄R₄')ₒ—Q'—(CR₄R₄')ₒ—(CH₂)—ONO₂;  (35)

—Y—(CR₄R₄')_q—C(Z)—(CR₄R₄')_q—(W)_q—
(CR₄R₄')_o—Q'—(CR₄R₄')_o—(CH₂)—ONO₂;    (36)

—NR_j—O—(CH₂)_o—V—(CR₄R₄')_o—Q'—(CH₂)—
ONO₂;    (37)

—NR_j—O—(CH₂)_o—(W)_q—(CR₄R₄')_o—Q'—
(CH₂)—ONO₂;    (38)

—O—NR_j—(CH₂)_o—(W)_q—(CR₄R₄')_o—Q'—
(CH₂)—ONO₂;    (39)

—O—NR_j—(CH₂)_o—V—(CR₄R₄')_o—Q'—(CH₂)—
ONO₂;    (40)

—NR_j—NR_j—(CR₄R₄')_p—(W)_q—(T)_o—(CR₄R₄')_o
—(CH₂)—ONO₂; or    (41)

—Y—(CR₄R₄')_o—Q'—(CR₄R₄')_o—ONO₂; or    (42)

—Y—(CR₄R₄')_o—V—(CR₄R₄')_o—Q—(CR₄R₄')_o—
ONO₂;    (43)

$R_4$ and $R_4'$ at each occurrence are independently a hydrogen, lower alkyl group, —OH, —CH₂OH, —ONO₂, —NO₂ or —CH₂ONO₂; or $R_4$ and $R_4'$ taken together with the carbon atom to which they are attached are a cycloalkyl group or a heterocyclic ring;

V is —C(O)—T—, —T—C(O)—, —T—C(O)—T or T—C(O)—C(O)—T;

W is a covalent bond or a carbonyl group;

T at each occurrence is independently an oxygen, $(S(O)_o)_o$ or $NR_j$;

$R_j$ is a hydrogen, an alkyl group, an aryl group, a heterocyclic ring, an alkylcarbonyl group, an alkylaryl group, an alkylsulfinyl group, an alkylsulfonyl group, an arylsulfinyl group, an arylsulfonyl group, a sulfonamido group, a N-alkylsulfonamido group, a N,N-diarylsulfonamido group, a N-arylsulfonamido group, a N-alkyl-N-arylsulfonamido group, a carboxamido group or a hydroxyl group;

p at each occurrence is independently an integer from 1 to 6;

q at each occurrence is independently an integer from 1 to 3;

o at each occurrence is independently an integer from 0 to 2;

Y is independently a covalent bond, a carbonyl, an oxygen, —S(O)_o— or —NR_j;

B is either phenyl or (CH₂)_o;

Q' is a cycloalkyl group, a heterocyclic ring or an aryl group;

Z is (=O), (=N—OR₅), (=N—NR₅R'₅) or (=CR₅R'₅);

M and M' are each independently —O⁻H₃N⁺—(CR₄R'₄)_q—CH₂ONO₂ or —T—(CR₄R'₄)_o—CH₂ONO₂; and $R_5$ and $R_5'$ at each occurrence are independently a hydrogen, a hydroxyl group, an alkyl group, an aryl group, an alkylsulfonyl group, an arylsulfonyl group, a carboxylic ester, an alkylcarbonyl group, an arylcarbonyl group, a carboxamido group, an alkoxyalkyl group, an alkoxyaryl group, a cycloalkyl group or a heterocyclic ring.

In other embodiments for the compounds of Formula (I), (II) or (III) and pharmaceutically acceptable salts thereof, K is:

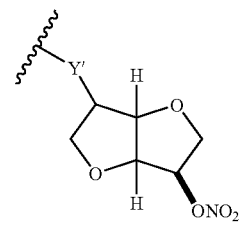
(1)

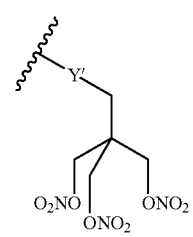
(2)

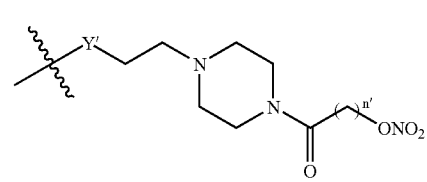
(3)

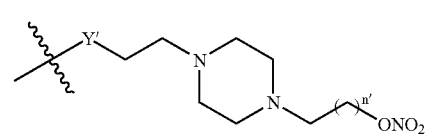
(4)

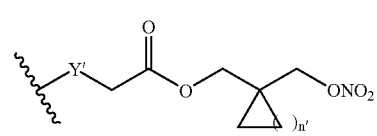
(5)

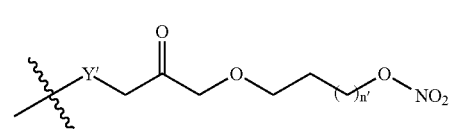
(6)

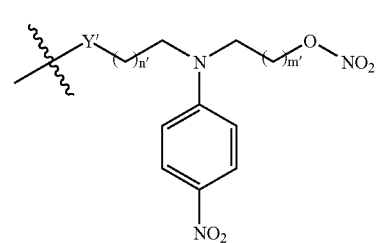
(7)

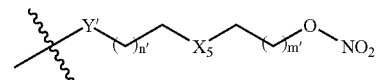
(8)

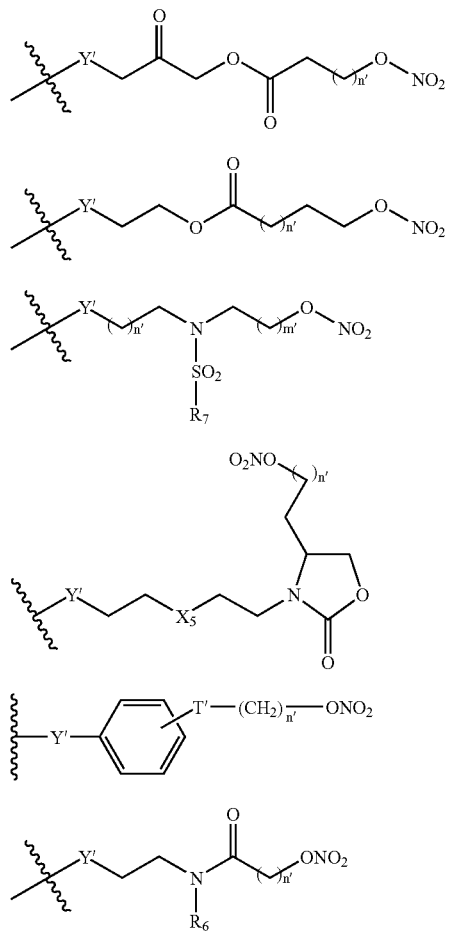
wherein T' maybe ortho, meta or para
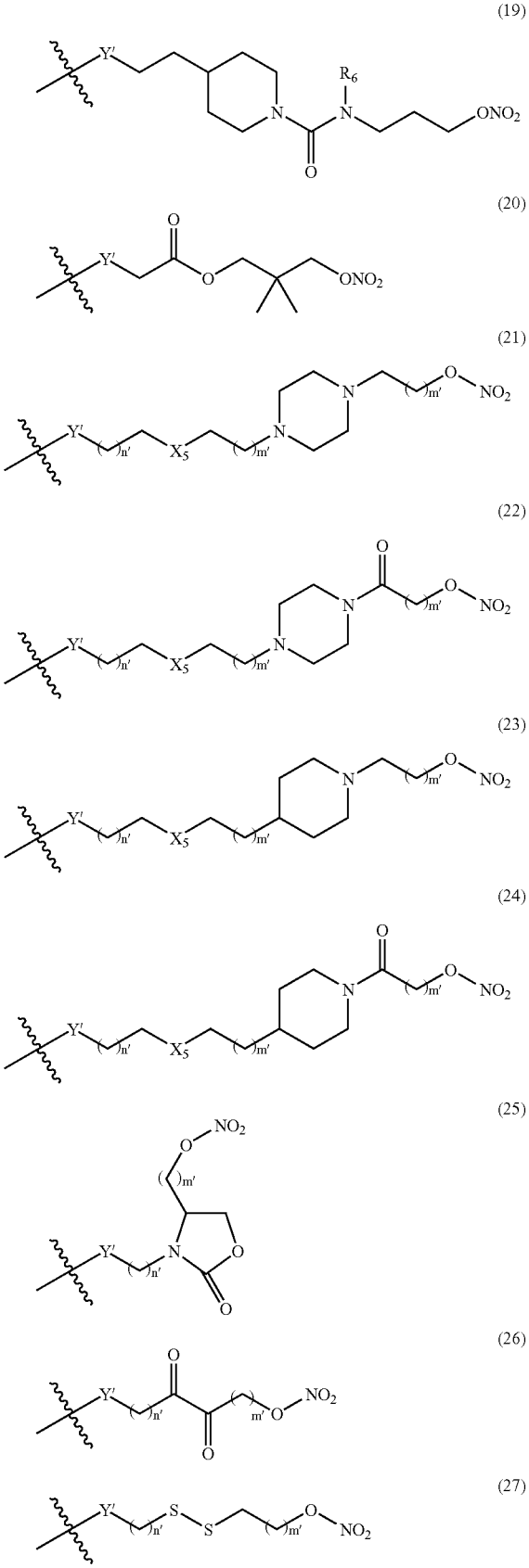

-continued

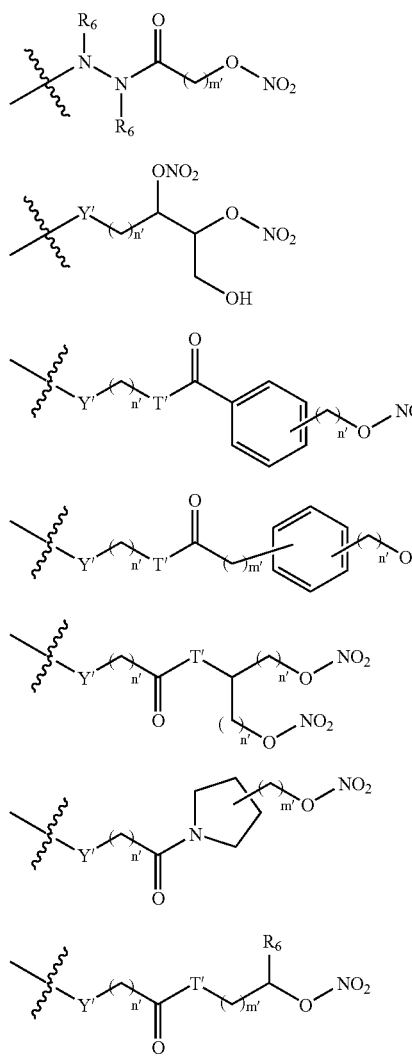

wherein the compound of Formula (IV) is:

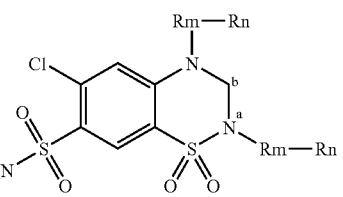

wherein the bond a-b can be a single bond (hydrochlorothiazide) or a double bond (chlorothiazide);
and the compound of Formula (V) is:

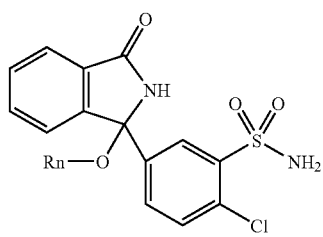

and the compound of Formula (VI) is:

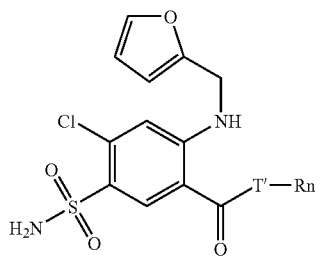

wherein:

Y' a covalent bond, a carbonyl, an oxygen, —S(O)$_o$— or —NR$_6$;

T' is oxygen, sulfur or NR$_6$;

X$_5$ is oxygen, (S(O)$_o$)$_o$ or NR$_6$;

R$_6$ is a hydrogen, a lower alkyl group, an aryl group;

R$_7$ is a lower alkyl group or an aryl group;

R$_8$ at each occurrence is independently is a hydrogen, a hydroxyl group, a lower alkyl group, an aryl group, —NO$_2$, —CH$_2$—ONO$_2$ or —CH$_2$—OH;

n' and m' are each independently an integer from 0 to 10; and o is an integer from 0 to 2.

In other embodiments of the invention, the nitrosated diuretic compounds of Formula (I) is a nitrosated chlorothiazide or a nitrosated hydrochlorothiazide of Formula (IV) and the nitrosated diuretic compound of Formula (II) is a nitrosated chlorthalidone of Formula (V) a nitrosated furosemide of Formula (VI) or a pharmaceutically acceptable salt thereof, wherein T' is oxygen, sulfur or NR$_6$;

R$_6$ is a hydrogen, a lower alkyl group, an aryl group;

R$_m$—R$_n$ taken together can be a hydrogen atom; or

R$_m$ is:
(i) —C—(O)—;
(ii) —C—(O)—NR$_6$;
(iii) —C(O)—O—;
(iv) —C(O)—S;
(v) —CH$_2$—O—; or
(vi) —CH(CH$_3$)—O—;

R$_n$ is:

a hydrogen or:

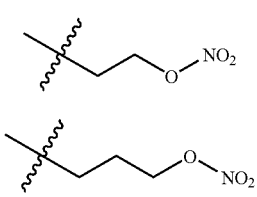

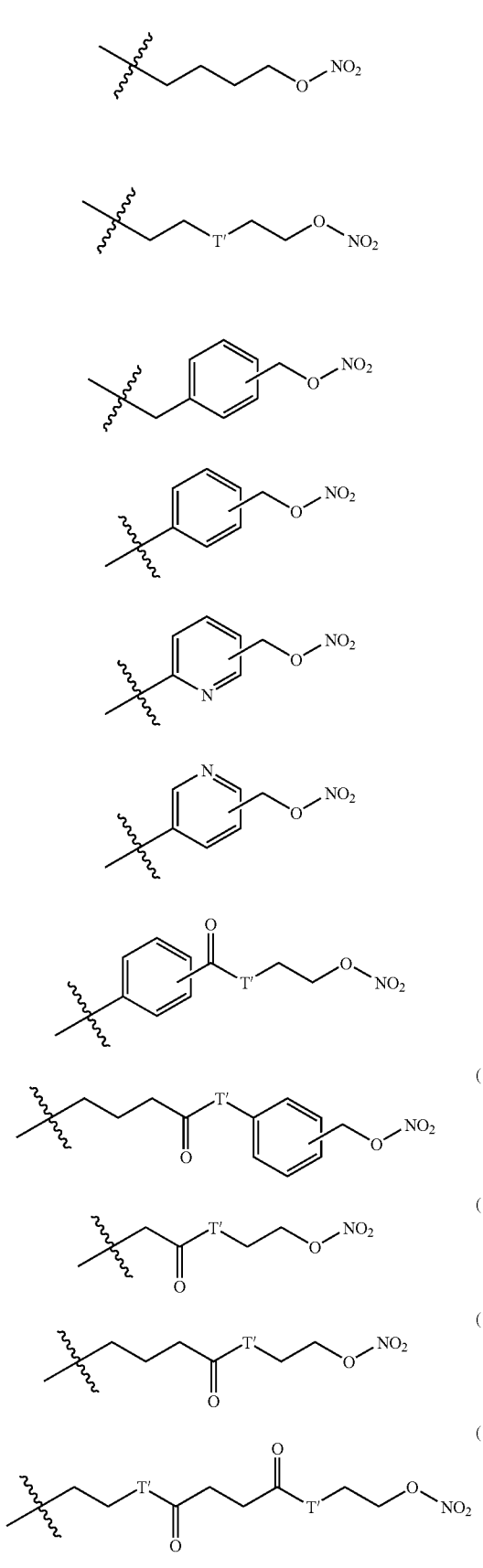
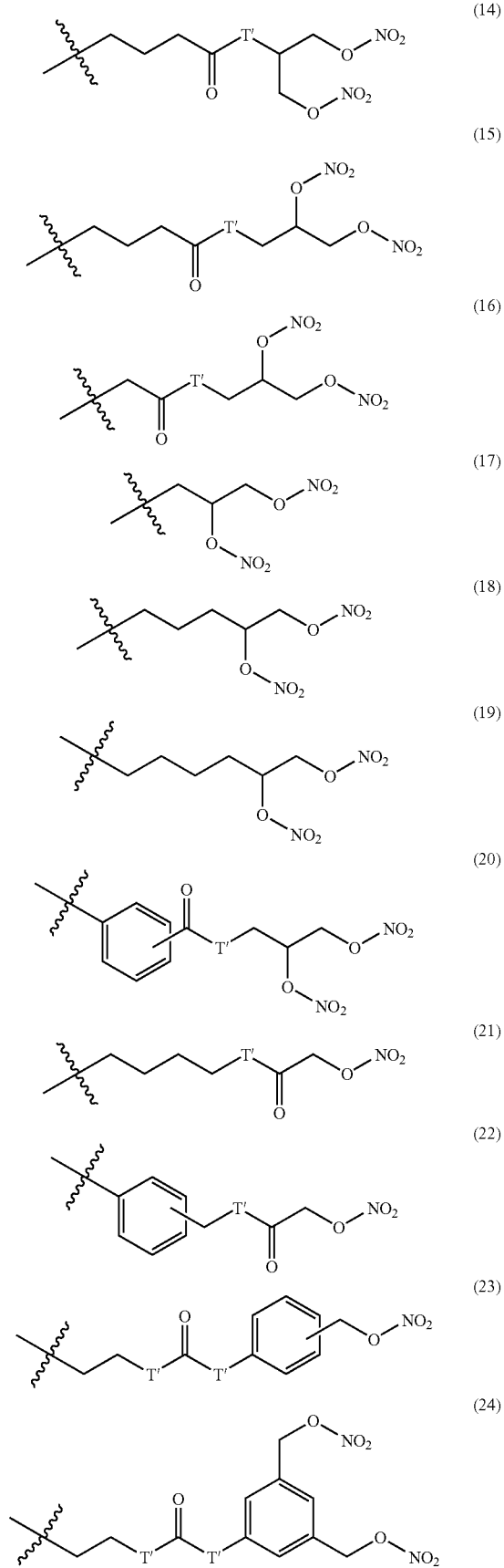

-continued

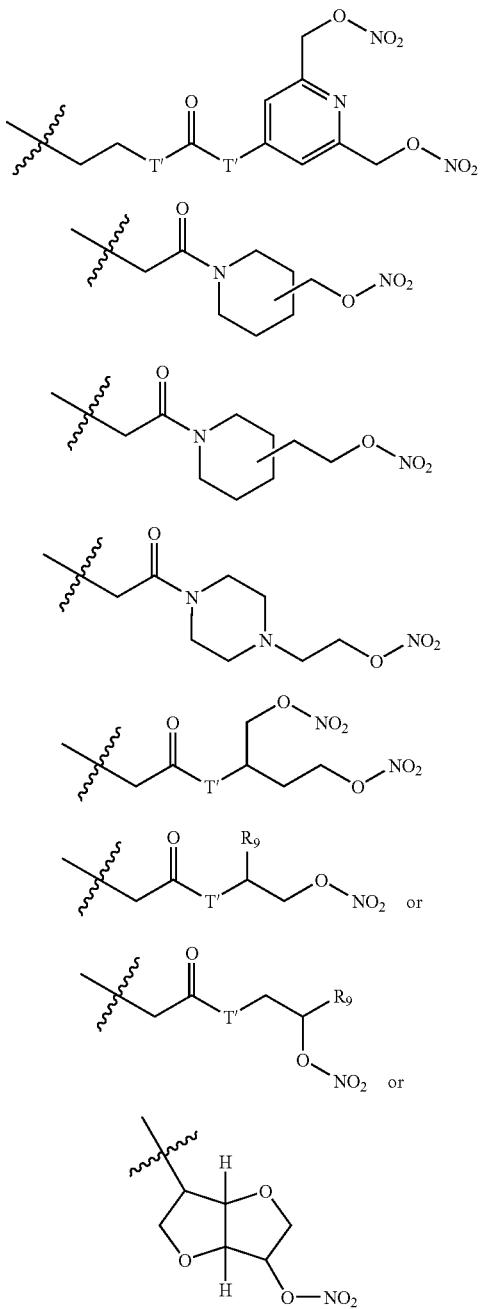

wherein:
R₉ is a lower alkyl group;
T' is oxygen, sulfur or NR₆;
R₆ is a hydrogen, a lower alkyl group, an aryl group; and
with the proviso that the compounds of Formula (IV), (V) and (VI) must contain at least one —NO₂ group.

In another embodiment, the nitrosated furosemide compound of Formula (IV) is:

(N-(2-(nitrooxy)ethyl)carbamoyl)methyl 4-chloro-2-((2-furylmethyl)amino)-5-sulfamoylbenzoate;

(N-methyl-N-(2-(nitrooxy)ethyl)carbamoyl)methyl 4-chloro-2-((2-furylmethyl)amino)-5-sulfamoylbenzoate;

2-(4-((nitrooxy)methyl)piperidyl)-2-oxoethyl 4-chloro-2-((2-furylmethyl)amino)-5-sulfamoylbenzoate;

2-(4-(2-(nitrooxy)ethyl)piperidyl)-2-oxoethyl 4-chloro-2-((2-furylmethyl)amino)-5-sulfamoylbenzoate;

2-(4-(2-(nitrooxy)ethyl)piperazinyl)-2-oxoethyl 4-chloro-2-((2-furylmethyl)amino)-5-sulfamoylbenzoate;

2-(4-(2-(nitrooxy)ethyl)piperazinyl)-2-oxoethyl 4-chloro-2-((2-furylmethyl)amino)-5-sulfamoylbenzoate, hydrochloride;

2-(4-(2-(nitrooxy)ethyl)piperazinyl)-2-oxoethyl 4-chloro-2-((2-furylmethyl)amino)-5-sulfamoylbenzoate, citric acid salt;

(N-ethyl-N-(2-(nitrooxy)ethyl)carbamoyl)methyl 4-chloro-2-((2-furylmethyl)amino)-5-sulfamoylbenzoate;

(N-((1S)-3-(nitrooxy)-1-((nitrooxy)methyl)propyl)carbamoyl)methyl 4-chloro-2-((2-furylmethyl)amino)-5-sulfamoylbenzoate;

2-((2R)-2-((nitrooxy)methyl)pyrrolidinyl)-2-oxoethyl 4-chloro-2-((2-furylmethyl)amino)-5-sulfamoylbenzoate;

(N-((1R)-1-((nitrooxy)methyl)propyl)carbamoyl)methyl4-chloro-2-((2-furylmethyl)amino)-5-sulfamoylbenzoate;

(N-((2S)-2-(nitrooxy)propyl)carbamoyl)methyl4-chloro-2-((2-furylmethyl)amino)-5-sulfamoylbenzoate;

(N-((2R)-2,3-bis(nitrooxy)propyl)carbamoyl)methyl4-chloro-2-((2-furylmethyl)amino)-5-sulfamoylbenzoate;

2-chloro-4-((2-furylmethyl)amino)-5-((4-(nitrooxy)piperidyl)carbonyl)benzenesulfonamide;

2-((4-chloro-6-((2-furylmethyl)amino)-3-sulfamoylphenyl) carbonylamino)ethyl (2S)-1-¹⁵N-nitroso-pyrrolidine-2-carboxylate;

2-(4-chloro-6-((2-furylmethyl)amino)-3-sulfamoylphenylcarbonyloxy)ethyl 2-(nitrooxy)ethyl butane-1,4-dioate; and ((2R)-1-nitrosopyrrolidin-2-yl)methyl 4-chloro-2-((2-furylmethyl)amino)-5-sulfamoylbenzoate.

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the invention anticipates and includes within its scope all such isomers and mixtures thereof.

Another embodiment of the invention describes the metabolites of the nitrosated and/or nitrosylated diuretic compounds and pharmaceutically acceptable salts thereof. These metabolites, include but are not limited to, the non-nitrosated and/or nitrosylated derivatives, degradation products, hydrolysis products, and the like, of the nitrosated and/or nitrosylated diuretic compounds and pharmaceutically acceptable salts thereof.

Another embodiment of the invention provides processes for making the novel compounds of the invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known for protecting thiol and alcohol groups against undesirable reactions during a synthetic procedure and many such protecting groups are known and described by, for example, Greene and Wuts, *Protective Groups in Organic Synthesis*, Third Edition, John Wiley & Sons, New York (1999).

The chemical reactions described herein are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

The compounds of Formulas (I), (II), (III), (IV), (V) and (VI) can be synthesized by one skilled in the art following the methods and examples described herein. Some of the parent diuretic compounds (i.e. non-nitrosated and/or non-nitrosylated diuretic compound) are commercially available. The synthesis of the parent diuretic compounds are also disclosed in, for example, U.S. Pat. Nos. 2,809,194, 2,976,289, 3,055,904, 3,058,882, 3,255,241, 3,360,518, 3,392,168, 3,565,911, 3,665,002, 3,758,506, 3,806,534, 4,010,273, 4,018,020, 6,767,917 and in JP 7305,585 and in DE 1,163,332, and in J. Am. Chem. Soc. 82: 1132 (1960), the disclosures of each of which are incorporated by reference herein in their entirety. The parent diuretic compounds are nitrosated and/or nitrosylated through one or more sites such as oxygen, sulfur and/or nitrogen using conventional methods known to one skilled in the art. Known methods for nitrosating and/or nitrosylating compounds are described in U.S. Pat. Nos. 5,380,758, 5,859,053, 5,703,073 and 6,297,260; and in WO 94/03421, WO 94/04484, WO 94/12463, WO 95/09831, WO 95/19952, WO 95/30641, WO 97/27749, WO 98/09948, WO 98/19672, WO 98/21193, WO 00/51988, WO 00/61604, WO 00/72838, WO 01/00563, WO 01/04082, WO 01/10814, WO 01/12584, WO 01/45703, WO 00/61541, WO 00/61537, WO 02/11707, WO 02/30866 and in Oae et al, *Org. Prep. Proc. Int.*, 15(3):165-198 (1983), the disclosures of each of which are incorporated by reference herein in their entirety. The methods of nitrosating and/or nitrosylating the compounds described in these references can be applied by one skilled in the art to produce any of the nitrosated and/or nitrosylated diuretic compounds described herein. The nitrosated and/or nitrosylated diuretic compounds of the invention donate, transfer or release a biologically active form of nitrogen monoxide (i.e., nitric oxide).

Compounds contemplated for use in the invention, e.g., diuretic compounds that are nitrosated and/or nitrosylated, through one or more sites such as oxygen (hydroxyl condensation), sulfur (sulfhydryl condensation) and/or nitrogen, are, optionally, used in combination with nitric oxide and compounds that release nitric oxide or otherwise directly or indirectly deliver or transfer a biologically active form of nitrogen monoxide to a site of its intended activity, such as on a cell membrane in vivo.

Nitrogen monoxide can exist in three forms: NO— (nitroxyl), NO• (nitric oxide) and NO$^+$ (nitrosonium). NO• is a highly reactive short-lived species that is potentially toxic to cells. This is critical because the pharmacological efficacy of NO depends upon the form in which it is delivered. In contrast to the nitric oxide radical (NO•), nitrosonium (NO$^+$) does not react with $O_2$ or $O_2$— species, and functionalities capable of transferring and/or releasing NO$^+$ and NO— are also resistant to decomposition in the presence of many redox metals. Consequently, administration of charged NO equivalents (positive and/or negative) does not result in the generation of toxic by-products or the elimination of the active NO moiety.

The term "nitric oxide" encompasses uncharged nitric oxide (NO•) and charged nitrogen monoxide species, preferably charged nitrogen monoxide species, such as nitrosonium ion (NO$^+$) and nitroxyl ion (NO—). The reactive form of nitric oxide can be provided by gaseous nitric oxide. The nitrogen monoxide releasing, delivering or transferring compounds have the structure F—NO, wherein F is a nitrogen monoxide releasing, delivering or transferring moiety, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-alkyl-2-((E)-hydroxyimino)-5-nitro-3-hexeneamines, N-((2Z, 3E)-4-ethyl-2-(hydroxyimino)-6-methyl-5-nitro-3-heptenyl)-3-pyridinecarboxamide (FR 146801), N-nitrosoamines, N-hydroxyl nitrosamines, nitrosimines, diazetine dioxides, oxatriazole 5-imines, oximes, hydroxylamines, N-hydroxyguanidines, hydroxyureas, benzofuroxanes, furoxans as well as substrates for the endogenous enzymes which synthesize nitric oxide.

Suitable NONOates include, but are not limited to, (Z)-1-(N-methyl-N-(6-(N-methyl-ammoniohexyl)amino)diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-(N-(3-aminopropyl)-N-(4-(3-aminopropylammonio)butyl)-amino)diazen-1-ium-1,2-diolate (spermine NONOate or "SPER/NO") and sodium(Z)-1-(N, N-diethylamino)diazenium-1,2-diolate (diethylamine NONOate or "DEA/NO") and derivatives thereof. NONOates are also described in U.S. Pat. Nos. 6,232,336, 5,910,316 and 5,650,447, the disclosures of which are incorporated herein by reference in their entirety. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

Suitable furoxanes include, but are not limited to, CAS 1609, C93-4759, C92-4678, S35b, CHF 2206, CHF 2363, and the like.

Suitable sydnonimines include, but are not limited to, molsidomine (N-ethoxycarbonyl-3-morpholinosydnonimine), SIN-1 (3-morpholinosydnonimine) CAS 936 (3-(cis-2,6-dimethylpiperidino)-N-(4-methoxybenzoyl)-sydnonimine, pirsidomine), C87-3754 (3-(cis-2,6-dimethylpiperidino)sydnonimine, linsidomine, C4144 (3-(3, 3-dimethyl-1,4-thiazane-4-yl)sydnonimine hydrochloride), C89-4095 (3-(3,3-dimethyl-1,1-dioxo-1,4-thiazane-4-yl) sydnonimine hydrochloride, and the like.

Suitable oximes, include but are not limited to, NOR-1, NOR-3, NOR-4, and the like.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5-200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3):165-198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) HS(C($R_e$)($R_f$))$_m$SNO;
(ii) ONS(C($R_e$)($R_f$))$_m$$R_e$; or
(iii) $H_2N$—CH($CO_2H$)—($CH_2$)$_m$—C(O)NH—CH($CH_2$SNO)—C(O)NH—$CH_2$—$CO_2H$;

wherein m is an integer from 2 to 20;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, K or $R_e$ and $R_f$ taken together with the carbons to which they are attached form a carbonyl, a methanthial, a heterocyclic ring, a cycloalkyl group, an aryl group, an oxime, a hydrazone or a bridged cycloalkyl group;

K is —($W_3$)$_a$—$E_b$—(C($R_e$)($R_f$))$_{p1}$—$E_c$—(C($R_e$)($R_f$))$_x$—($W_3$)$_d$—(C($R_e$)($R_f$))$_y$—($W_3$)$_i$—$E_j$—($W_3$)$_g$—(C($R_e$)($R_f$))$_z$—$U_3$—$V_3$;

$V_3$ is —NO or —$NO_2$;

a, b, c, d, g, i and j are each independently an integer from 0 to 3;

p1, x, y and z are each independently an integer from 0 to 10;

$W_3$ at each occurrence is independently —C(O)—, —C(S)—, -$T_3$-, —(C($R_e$)($R_f$))$_h$—, an alkyl group, an aryl group, a heterocyclic ring, an arylheterocyclic ring, or —($CH_2CH_2O$)$_{q1}$—;

E at each occurrence is independently -$T_3$-, an alkyl group, an aryl group, —(C($R_e$)($R_f$))$_h$—, a heterocyclic ring, an arylheterocyclic ring, or —($CH_2CH_2O$)$_{q1}$—;

$T_3$ at each occurrence is independently a covalent bond, a carbonyl, an oxygen, —S(O)$_o$— or —N($R_a$)$R_i$;

h is an integer form 1 to 10;

$q_1$ is an integer from 1 to 5;

$U_3$ at each occurrence is independently a covalent bond, a carbonyl, an oxygen, —S(O)$_o$— or —N($R_a$)$R_i$;

o is an integer from 0 to 2;

$R_a$ is a lone pair of electrons, a hydrogen or an alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, arylsulphonyloxy, a sulfonamido, a carboxamido, a carboxylic ester, an aminoalkyl, an aminoaryl, —$CH_2$—C($U_3$—$V_3$)($R_e$)($R_f$), a bond to an adjacent atom creating a double bond to that atom, —($N_2O_2$—)$^-$•$M_1^+$, wherein $M_1^+$ is an organic or inorganic cation.

In cases where $R_e$ and $R_f$ are a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the invention, where the NO adduct is a compound that donates, transfers or releases nitric oxide, include compounds comprising at least one ON—O— or ON—N— group. The compounds that include at least one ON—O— or ON—N— group are preferably ON—O— or ON—N-polypeptides (the term "polypeptide" includes proteins and polyamino acids that do not possess an ascertained biological function, and derivatives thereof); ON—O— or ON—N-amino acids (including natural and synthetic amino acids and their stereoisomers and racemic mixtures); ON—O— or ON—N-sugars; ON—O— or —ON—N— modified or unmodified oligonucleotides (comprising at least 5 nucleotides, preferably 5-200 nucleotides); ON—O— or ON—N— straight or branched, saturated or unsaturated, aliphatic or aromatic, substituted or unsubstituted hydrocarbons; and ON—O—, ON—N— or ON—C-heterocyclic compounds. Preferred examples of compounds comprising at least one ON—O— or ON—N— group include butyl nitrite, isobutyl nitrite, tert-butyl nitrite, amyl nitrite, isoamyl nitrite, N-nitrosamines, N-nitrosamides, N-nitrosourea, N-nitrosoguanidines, N-nitrosocarbamates, N-acyl-N-nitroso compounds (such as, N-methyl-N-nitrosourea); N-hydroxy-N-nitrosamines, cupferron, alanosine, dopastin, 1,3-disubstitued nitrosiminobenzimidazoles, 1,3,4-thiadiazole-2-nitrosimines, benzothiazole-2(3H)-nitrosimines, thiazole-2-nitrosimines, oligonitroso sydnonimines, 3-alkyl-N-nitrososydnonimines, 2H-1,3,4-thiadiazine nitrosimines.

Another group of NO adducts for use in the invention include nitrates that donate, transfer or release nitric oxide, such as compounds comprising at least one $O_2N$—O—, $O_2N$—N— or $O_2N$—S— group. Preferred among these compounds are $O_2N$—O—, $O_2N$—N— or $O_2N$—S— polypeptides (the term "polypeptide" includes proteins and also polyamino acids that do not possess an ascertained biological function, and derivatives thereof); $O_2N$—O—, $O_2N$—N— or $O_2N$—S— amino acids (including natural and synthetic amino acids and their stereoisomers and racemic mixtures); $O_2N$—O—, $O_2N$—N— or $O_2N$—S— sugars; $O_2N$—O—, $O_2N$—N— or $O_2N$—S— modified and unmodified oligonucleotides (comprising at least 5 nucleotides, preferably 5-200 nucleotides); $O_2N$—O—, $O_2N$—N— or $O_2N$—S— straight or branched, saturated or unsaturated, aliphatic or aromatic, substituted or unsubstituted hydrocarbons; and $O_2N$—O—, $O_2N$—N— or $O_2N$—S— heterocyclic compounds. Preferred examples of compounds comprising at least one $O_2N$—O—, $O_2N$—N— or $O_2N$—S— group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 5185, SPM 5186 and those disclosed in U. S. Pat. Nos. 5,284,872, 5,428,061, 5,661,129, 5,807,847 and 5,883,122 and in WO 97/46521, WO 00/54756 and in WO 03/013432, the disclosures of each of which are incorporated by reference herein in their entirety.

Another group of NO adducts are N-oxo-N-nitrosoamines that donate, transfer or release nitric oxide and are represented by the formula: $R^{1'''}R^{2'''}N$—$N(O-M^+)$—NO, where $R^{1'''}$ and $R^{2'''}$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where $M_1^+$ is an organic or inorganic cation, such, as for example, an alkyl substituted ammonium cation or a Group I metal cation.

The invention is also directed to compounds that stimulate endogenous NO or elevate levels of endogenous endothelium-derived relaxing factor (EDRF) in vivo or are oxidized to produce nitric oxide and/or are substrates for nitric oxide synthase and/or cytochrome P450. Such compounds include, for example, L-arginine, L-homoarginine, and N-hydroxy-L-arginine, N-hydroxy-L-homoarginine, N-hydroxydebrisoquine, N-hydroxypentamidine including their nitrosated and/or nitrosylated analogs (e.g., nitrosated L-arginine, nitrosylated L-arginine, nitrosated N-hydroxy-L-arginine, nitrosylated N-hydroxy-L-arginine, nitrosated and nitrosylated L-homoarginine), N-hydroxyguanidine compounds, amidoxime, ketoximes, aldoxime compounds, that can be oxidized in vivo to produce nitric oxide. Compounds that may be substrates for a cytochrome P450, include, for example, imino(benzylamino)methylhydroxylamine, imino(((4-methylphenyl)methyl) amino)methylhydroxylamine, imino(((4-methoxyphenyl)methyl)amino) methylhydroxylamine, imino(((4-(trifluoromethyl)phenyl) methyl)amino) methylhydroxylamine, imino(((4-nitrophenyl) methyl)amino)methylhydroxylamine, (butylamino)iminomethylhydroxylamine, imino (propylamino) methylhydroxylamine, imino (pentylamino)methylhydroxylamine, imino (propylamino)methylhydroxylamine, imino ((methylethyl)amino)methylhydroxylamine, (cyclopropylamino) iminomethylhydroxylamine, imino-2-1,2,3,4-tetrahydroisoquinolyl methylhydroxylamine, imino(1-methyl (2-1,2,3,4-tetrahydroisoquinolyl))methylhydroxylamine, (1,3-dimethyl(2-1,2,3,4-tetrahydroisoquinolyl)) iminomethylhydroxylamine, (((4-chlorophenyl)methyl)amino)iminomethylhydroxylamine, ((4-chlorophenyl)amino)iminomethylhydroxylamine, (4-chlorophenyl)(hydroxyimino) methylamine, and 1-(4-chlorophenyl)-1-(hydroxyimino) ethane, and the like, precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid), nitric oxide mediators and/ or physiologically acceptable salts thereof, including, for example, pyruvate, pyruvate precursors, α-keto acids having four or more carbon atoms, precursors of α-keto acids having four or more carbon atoms (as disclosed in WO 03/017996, the disclosure of which is incorporated herein in its entirety), and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature*, 327:524-526 (1987); Ignarro et al, *Proc. Natl. Acad. Sci. USA*, 84:9265-9269 (1987)).

In another embodiment of the invention the combination of the parent diuretic compounds of the invention (i.e. non-nitrosated and/or non-nitrosylated diuretic compounds) with nitric oxide donor compounds do not include the combinations disclosed in U.S. Ser. No. 2003/0216384, the disclosure of which is incorporated herein in its entirety.

The invention is also based on the discovery that compounds and compositions of the invention may be used in conjunction with other therapeutic agents for co-therapies, partially or completely, in place of other therapeutic agents, such as, for example, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. The therapeutic agent may optionally be nitrosated and/or nitrosylated.

Suitable aldosterone antagonists include, but are not limited to, canrenone, potassium canrenoate, drospirenone, spironolactone, eplerenone (INSPRA®), epoxymexrenone, fadrozole, pregn-4-ene-7,21-dicarboxylic acid, 9,11-epoxy-17-hydroxy-3-oxo, γ-lactone, methyl ester, (7α, 11α, 17β.)-; pregn-4-ene-7,21-dicarboxylic acid, 9,11-epoxy-17-hydroxy-3-oxo-dimethyl ester, (7α, 11α, 17β.)-; 3'H-cyclopropa(6,7)pregna-4,6-diene-21-carboxylic acid, 9,11-epoxy-6,7-dihydro-17-hydroxy-3-oxo-, γ-lactone, (6β,7β,11α, 17β)-; pregn-4-ene-7,21-dicarboxylic acid, 9,11-epoxy-17-hydroxy-3-oxo-, 7-(1-methylethyl) ester, monopotassium salt, (7α,11α,17β.)-; pregn-4-ene-7,21-dicarboxylic acid, 9,11,-epoxy-17-hydroxy-3-oxo-, 7-methyl ester, monopotassium salt, (7α,11α,17β.)-; 3'H-cyclopropa(6,7)pregna-1,4,6-triene-21-carboxylic acid, 9,11-epoxy-6,7-dihydro-17-hydroxy-3-oxo-, γ-lactone, (6β,7β,11α)-; 3'H-cyclopropa(6,7)pregna-4,6-diene-21-carboxylic acid, 9,11-epoxy-6,7-dihydro-17-hydroxy-3-oxo-, methyl ester, (6β,7β,11α,17β)-; 3'H-cyclopropa (6,7)pregna-4,6-diene-21-carboxylic acid, 9,11-epoxy-6,7-dihydro-17-hydroxy-3-oxo-, monopotassium salt, (6β,7β,11α,17β)-; 3'H-cyclopropa(6,7)pregna-1,4,6-triene-21-carboxylic acid, 9,11-epoxy-6,7-dihydro-17-hydroxy-3-oxo-, γ-lactone, (6β,7β,11α,17β)-; pregn-4-ene-7,21-dicarboxylic acid, 9,11-epoxy-17-hydroxy-3-oxo-, γ-lactone, ethyl ester, (7α, 11α,17β)-; pregn-4-ene-7,21-dicarboxylic acid, 9,11-epoxy-17-hydroxy-3-oxy-, γ-lactone, 1-methylethyl ester, (7α,11α, 17β)-; RU-28318, and the like. Suitable aldosterone antagonists are described more fully in the literature, such as in Goodman and Gilman, The Pharmacological Basis of Therapeutics (9th Edition), McGraw-Hill, 1995; and the Merck Index on CD-ROM, 13$^{th}$ Edition; and on STN Express, file phar and file registry.

In some embodiment the aldosterone antagonists is eplerenone or spironolactone (a potassium sparing diuretic that acts like an aldosterone antagonist). In more particular embodiments eplerenone is administered in an amount of about 25 milligrams to about 300 milligrams as a single dose or as multiple doses per day; the spironolactone is administered in an amount of about 25 milligrams to about 150 milligrams as a single dose or as multiple doses per day.

Suitable alpha-adrenergic receptor antagonists include but are not limited to, phentolamine, tolazoline, idazoxan, deriglidole, RX 821002, BRL 44408, BRL 44409, BAM 1303, labetelol, ifenprodil, rauwolscine, corynathine, raubascine, tetrahydroalstonine, apoyohimbine, akuammigine, β-yohimbine, yohimbol, yohimbine, pseudoyohimbine, epi-3α-yohimbine, 10-hydroxy-yohimbine, 11-hydroxy-yohimbine, tamsulosin, benoxathian, atipamezole, BE 2254, WB 4101, HU-723, tedisamil, mirtazipine, setiptiline, reboxitine, delequamine, naftopil, saterinone, SL 89.0591, ARC 239, urapidil, 5-methylurapidil, monatepi, haloperidol, indoramin, SB 216469, moxisylyte, trazodone, dapiprozole, efaroxan, Recordati 15/2739, SNAP 1069, SNAP 5089, SNAP 5272, RS 17053, SL 89.0591, KMD 3213, spiperone, AH 11110A, chloroethylclonidine, BMY 7378, niguldipine, and the like. Suitable alpha-adrenergic receptor antagonists are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable angiotensin II antagonists include, but are not limited to, angiotensin, abitesartan, candesartan, candesartan cilexetil, elisartan, embusartan, enoltasosartan, eprosartan, fonsartan, forasartan, glycyllosartan, irbesartan, losartan, olmesartan, milfasartan, medoxomil, ripisartan, pratosartan, saprisartan, saralasin, sarmesin, tasosartan, telmisartan, valsartan, zolasartan, 3-(2'(tetrazole-5-yl)-1,1'-biphen-4-yl)methyl-5,7-dimethyl-2-ethyl-3H-imidazo(4,5-b)pyridine, antibodies to angiotensin II, A-81282, A-81988, BAY 106734, BIBR-363, BIBS-39, BIBS-222, BMS-180560, BMS-184698, BMS-346567, CGP-38560A, CGP-42112A, CGP-48369, CGP-49870, CGP-63170, CI-996, CP-148130, CL-329167, CV-11194, DA-2079, DE-3489, DMP-811, DuP-167, DuP-532, DuP-753, E-1477, E-4177, E-4188, EMD-66397, EMD-666R4, EMD-73495, EMD-66684, EXP-063, EXP-929, EXP-3174, EXP-6155, EXP-6803, EXP-7711, EXP-9270, EXP-9954, FK-739, FRI 153332, GA-0050, GA-0056, HN-65021, HOE-720, HR-720, ICI-D6888, ICI-D7155, ICI-D8731, KRI-1177, KT3-671, KT-3579, KW-3433, L-158809, L-158978,, L-159282, L-159689, L-159874, L-161177, L-162154, L-162234, L-162441, L-163007, L-163017, LF-70156, LRB-057, LRB-081, LRB-087, LY-235656, LY-266099, LY-285434, LY-301875, LY-302289, LY-315995, ME-3221, MK-954, PD-123177, PD-123319, PD-126055, PD-150304, RG-13647, RWJ-38970, RWJ-46458, S-8307, S-8308, SC-51757, SC-54629, SC-52458, SC-52459, SK 1080, SL-910102, SR-47436, TAK-536, UP-2696, U-96849, U-97018, UK-77778, UP-275-22, WAY-126227, WK-1260, WK-1360, WK-1492, WY 126227, YH-1498, YM-358, YM-31472, X-6803, XH-148, XR-510, ZD-6888, ZD-7155, ZD-8731, ZD 8131, the compounds of ACS registry numbers 124750-92-1, 133240-46-7, 135070-05-2, 139958-16-0, 145160-84-5, 147403-03-0, 153806-29-2, 439904-54-8P, 439904-55-9P, 439904-56-0P, 439904-57-1P, 439904-58-2P, 155918-60-8P, 155918-61-9P, 272438-16-1P, 272446-75-0P, 223926-77-0P, 169281-89-4, 439904-65-1P, 165113-01-9P, 165113-02-0P, 165113-03-1P, 165113-03-2P, 165113-05-3P, 165113-06-4P, 165113-07-5P, 165113-08-6P, 165113-09-7P, 165113-10-0P, 165113-11-1P, 165113-12-2P, 165113-17-7P, 165113-18-8P, 165113-19-9P, 165113-20-2P, 165113-13-3P, 165113-14-4P, 165113-15-5P, 165113-16-6P, 165113-21-3P, 165113-22-4P, 165113-23-5P, 165113-24-6P, 165113-25-7P, 165113-26-8P, 165113-27-9P, 165113-28-0P, 165113-29-1P, 165113-30-4P, 165113-31-5P, 165113-32-6P, 165113-33-7P, 165113-34-8P, 165113-35-9P, 165113-36-0P, 165113-37-1P, 165113-38-2P, 165113-39-3P, 165113-40-6P, 165113-41-7P, 165113-42-8P, 165113-43-9P, 165113-44-0P, 165113-45-1P, 165113-46-2P, 165113-47-3P, 165113-48-4P, 165113-49-5P, 165113-50-8P, 165113-51-9P, 165113-52-0P, 165113-53-1P, 165113-54-2P, 165113-55-3P, 165113-56-4P, 165113-57-5P, 165113-58-6P, 165113-59-7P, 165113-60-0P, 165113-61-1P, 165113-62-2P, 165113-63-3P, 165113-64-4P, 165113-65-5P, 165113-66-6P, 165113-67-7P, 165113-68-8P, 165113-69-9P, 165113-70-2P, 165113-71-3P, 165113-72-4P, 165113-73-5P, 165113-74-6P, 114798-27-5, 114798-28-6, 114798-29-7, 124749-82-2, 114798-28-6, 124749-84-4, 124750-88-5, 124750-91-0,124750-93-2, 161946-65-2P, 161947-47-3P, 161947-48-4P, 161947-51-9P, 161947-52-0P, 161947-55-3P, 161947-56-4P, 161947-60-0P, 161947-61-1P, 161947-68-8P, 161947-69-9P, 161947-70-2P, 161947-71-3P, 161947-72-4P, 161947-74-6P, 161947-75-7P, 161947-81-5P, 161947-82-6P, 161947-83-7P, 161947-84-8P, 161947-85-9P, 161947-86-0P, 161947-87-1P, 161947-88-2P, 161947-89-3P, 161947-90-6P, 161947-91-7P, 161947-92-8P, 161947-93-9P, 161947-94-0P, 161947-95-1P, 161947-96-2P, 161947-97-3P, 161947-98-4P, 161947-99-5P, 161948-00-1P, 161948-01-2P, 161948-02-3P, 168686-32-6P, 167301-42-0P, 166813-82-7P, 166961-56-4P, 166961-58-6P, 158872-96-9P, 158872-97-0P, 158807-14-8P, 158807-15-9P, 158807-16-0P, 158807-17-1P, 158807-18-2P, 158807-19-3P, 158807-20-6P, 155884-08-5P, 154749-99-2, 167371-59-7P, 244126-99-6P, 177848-35-0P and 141309-82-2P, and the like. Suitable angiotensin II antagonists are described more fully in the literature, such as in Goodman and Gilman, The Pharmacological Basis of Therapeutics (9th Edition), McGraw-Hill, 1995; and the Merck Index on CD-ROM, 13$^{th}$ Edition; and on STN Express, file phar and file registry.

In some embodiments the angiotensin II antagonists are candesartan, eprosartan, irbesartan, losartan, omlesartan, telmisartan or valsartan. In more particular embodiments the candesartan is administered as candesartan cilexetil in an amount of about 15 milligrams to about 100 milligrams as a single dose or as multiple doses per day; the eprosartan, is administered as eprosartan mesylate in an amount of about 400 milligrams to about 1600 milligrams as a single does or as multiple doses per day; the irbesartan is administered in an amount of about 75 milligrams to about 1200 milligrams as a single dose or as multiple doses per day; the losartan is administered as losartan potassium in an amount of about 25 milligrams to about 100 milligrams as a single dose or as multiple doses per day; the omlesartan is administered as omlesartan medoxomil in an amount of about 5 milligrams to about 40 milligrams as a single dose or as multiple doses per day; the telmisartan is administered in an amount of about 20 milligrams to about 80 milligrams as a single dose or as multiple doses per day; the valsartan is administered in an amount of about 80 milligrams to about 320 milligrams as a single dose or as multiple doses per day.

Suitable angiotensin-converting enzyme inhibitors (ACE inhibitors) include, but are not limited to, alacepril, benazepril (LOTENSIN®, CIBACEN®), benazeprilat, captopril, ceronapril, cilazapril, delapril, duinapril, enalapril, enalaprilat, fasidotril, fosinopril, fosinoprilat, gemopatrilat, glycopril, idrapril, imidapril, lisinopril, moexipril, moveltipril, naphthopidil, omapatrilat, pentopril, perindopril, perindoprilat, quinapril, quinaprilat, ramipril, ramiprilat, rentipril, saralasin acetate, spirapril, temocapril, trandolapril, trandolaprilat, urapidil, zofenopril, acylmercapto and mercaptoalkanoyl pralines, carboxyalkyl dipeptides, carboxyalkyl dipeptide, phosphinylalkanoyl pralines, registry no.796406, AVE 7688, BP1.137, CHF 1514, E 4030, ER 3295, FPL-66564, MDL 100240, RL 6134, RL 6207, RL 6893, SA 760, S-5590, Z 13752A, and the like. Suitable angiotensin-converting enzyme inhibitors are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

In some embodiments the angiotensin-converting enzyme inhibitors are benazepril, captopril, enalapril, fosinopril, lisinopril, moexipril, quinapril, ramipril, trandolapril or trandolaprilat. In more particular embodiments the benazepril is administered as benazepril hydrochloride in an amount of about 5 milligrams to about 80 milligrams as a single dose or as multiple doses per day; the captopril is administered in an amount of about 12.5 milligrams to about 450 milligrams as a single does or as multiple doses per day; the enalapril is administered as enalapril maleate in an amount of about 2.5 milligrams to about 40 milligrams as a single dose or as multiple doses per day; the fosinopril is administered as fosinopril sodium in an amount of about 5 milligrams to about 60 milligrams as a single dose or as multiple doses per day; the lisinopril is administered in an amount of about 12.5 milligrams to about 75 milligrams as a single dose or as multiple doses per day; the moexipril is administered as moexipril hydrochloride in an amount of about 7.5 milligrams to about 45 milligrams as a single dose or as multiple doses per day; the quinapril is administered as quinapril hydrochloride in an amount of about 5 milligrams to about 40 milligrams as single or multiple doses per day; the ramapril hydrochloride in an amount of about 1.25 milligrams to about 40 milligrams as single or multiple doses per day; the trandolapril is administered as in an amount of about 0.5 milligrams to about 4 milligrams as single or multiple doses per day; the trandolaprilat is administered as in an amount of about 0.5 milligrams to about 4 milligrams as single or multiple doses per day.

Suitable antidiabetic compounds include but are not limited to, acarbose, acetohexamide, buformin, carbutamide, chlorpropamide, glibornuride, gliclazide, glimepiride, glipizide, gliquidone, glisoxepid, glyburide, glybuthiazol(e), glybuzole, glyhexamide, glymidine, glypinamide, insulin, metformin, miglitol, nateglinide, phenbutamide, phenformin, pioglitazone, repaglinide, rosiglitazone, tolazamide, tolbutamide, tolcyclamide, troglitazone, voglibose, and the like. Suitable antidiabetic compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable anti-hyperlipidemic compounds include, but are not limited to, statins or HMG-CoA reductase inhibitors, such as, for example, atorvastatin (LIPITOR®), bervastatin, cerivastatin (BAYCOL®), dalvastatin, fluindostatin (Sandoz XU-62-320), fluvastatin, glenvastatin, lovastatin (MEVACOR®), mevastatin, pravastatin (PRAVACHOL®), rosuvastatin (CRESTRO®), simvastatin (ZOCOR®), velostatin (also known as synvinolin), VYTORIN™ (ezetimibe/simvastatin), GR-95030, SQ 33,600, BMY 22089, BMY 22,566, CI 980, and the like; gemfibrozil, cholystyramine, colestipol, niacin, nicotinic acid, bile acid sequestrants, such as, for example, cholestyramine, colesevelam, colestipol, poly(methyl-(3-trimethylaminopropyl) imino-trimethylene dihalide) and the like; probucol; fibric acid agents or fibrates, such as, for example, bezafibrate (Bezalip™), beclobrate, binifibrate, ciprofibrate, clinofibrate, clofibrate, etofibrate, fenofibrate (Lipidil™, Lipidil Micro™), gemfibrozil (Lopid™.), nicofibrate, pirifibrate, ronifibrate, simfibrate, theofibrate and the like; cholesterol ester transfer protein (CETP) inhibitors, such as for example, CGS 25159, CP-529414 (torcetrapid), JTT-705, substituted N-[3-(1,1,2,2-tetrafluoroethoxy)benzyl]-N-(3-phenoxyphenyl)-trifluoro-3-amino-2-propanols, N,N-disubstituted trifluoro-3-amino-2-propanols, PD 140195 (4-phenyl-5-tridecyl-4H-1,2,4-triazole-3-thiol), SC-794, SC-795, SCH 58149, and the like.

In some embodiments the anti-hyperlipidemic compounds are atorvastatin, fluvastatin, lovastatin, pravastatin, rosuvastatin or simvastatin. In more particular embodiments the atorvastatin is administered in an amount of about 10 milligrams to about 80 milligrams as a single dose or as multiple doses per day; the fluvastatin is administered in an amount of about 20 milligrams to about 80 milligrams as a single does or as multiple doses per day; the lovastatin is administered in an amount of about 10 milligrams to about 80 milligrams as a single dose or as multiple doses per day; the pravastatin is administered in an amount of about 10 milligrams to about 80 milligrams as a single dose or as multiple doses per day; the rosuvastatin is administered in an amount of about 5 milligrams to about 40 milligrams as a single dose or as multiple doses per day; the simvastatin is administered in an amount of about 5 milligrams to about 80 milligrams as a single dose or as multiple doses per day.

Suitable antioxidants include, but are not limited to, small-molecule antioxidants and antioxidant enzymes. Suitable small-molecule antioxidants include, but are not limited to, hydralazine compounds, glutathione, vitamin C, vitamin E, cysteine, N-acetyl-cysteine, β-carotene, ubiquinone, ubiquinol-10, tocopherols, coenzyme Q, superoxide dismutase mimetics, such as, for example, 2,2,6,6-tetramethyl-1-piperidinyloxy (TEMPO), DOXYL, PROXYL nitroxide compounds; 4-hydroxy-2,2,6,6-tetramethyl-1-piperidinyloxy (Tempol), M-40401, M-40403, M-40407, M-40419, M-40484, M-40587, M-40588, and the like. Suitable antioxidant enzymes include, but are not limited to, superoxide dismutase, catalase, glutathione peroxidase, NADPH oxidase inhibitors, such as, for example, apocynin, aminoguanidine, ONO 1714, S17834 (benzo(b)pyran-4-one derivative), and the like; xanthine oxidase inhibitors, such as, for example, allopurinol, oxypurinol, amflutizole, diethyldithiocarbamate, 2-styrylchromones, chrysin, luteolin, kaempferol, quercetin, myricetin, isorhamnetin, benzophenones such as 2,2',4,4'-tetrahydroxybenzophenone, 3,4,5,2', 3',4'-hexahydroxybenzophenone and 4,4'-dihydroxybenzophenone; benzothiazinone analogues such as 2-amino-4H-1,3-benzothiazine-4-one, 2-guanidino-4H-1,3-benzothiazin-4-one and rhodanine; N-hydroxyguanidine derivative such as, PR5 (1-(3,4-dimethoxy-2-chlorobenzylideneamino)-3-hydroxyguanidine); 6-formylpterin, and the like. The antioxidant enzymes can be delivered by gene therapy as a viral vertor and/or a non-viral vector. Suitable antioxidants are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the antioxidants are apocynin, hydralazine compounds and superoxide dimutase mimetics.

Suitable antithrombotic and vasodilator compounds include, but are not limited to, abciximab, acetorphan, acetylsalicylic acid, argatroban, bamethan, benfurodil, benziodarone, betahistine, bisaramil, brovincamine, bufeniode, citicoline, clobenfurol, clopidogrel, cyclandelate, dalteparin, dipyridamol, droprenilamine, enoxaparin, fendiline, ifenprodil, iloprost, indobufen, isobogrel, isoxsuprine, heparin, lamifiban, midrodine, nadroparin, nicotinoyl alcohol, nylidrin, ozagrel, perhexiline, phenylpropanolamine, prenylamine, papaveroline, reviparin sodium salt, ridogrel, suloctidil, tinofedrine, tinzaparin, trifusal, vintoperol, xanthinal niacinate, and the like. Suitable antithrombotic and vasodilator compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable β-adrenergic antagonists include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, butofilolol, carazolol, capsinolol, carteolol, carvedilol (COREG®), celiprolol, cetamolol, cindolol, cloranolol, dilevalol, diprafenone, epanolol, ersentilide, esmolol, esprolol, hedroxalal, indenolol, labetalol, landiolol, laniolol, levobunolol, mepindolol, methylpranol, metindol, metipranolol, metrizoranolol, metoprolol, moprolol, nadolol, nadoxolol, nebivolol, nifenalol, nipradilol, oxprenolol, penbutolol, pindolol, practolol, pronethalol, propranolol, sotalol, sotalolnadolol, sulfinalol, taliprolol, talinolol, tertatolol, tilisolol, timolol, toliprolol, tomalolol, trimepranol, xamoterol, xibenolol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl) phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide, Acc 9369, AMO-140, BIB-16S, CP-331684, Fr-172516, ISV-208, L-653328, LM-2616, SB-226552, SR-58894A, SR-59230A, TZC-5665, UK-1745, YM-430, and the like. Suitable β-adrenergic antagonists are described more fully in the literature, such as in Goodman and Gilman, The Pharmacological Basis of Therapeutics (9th Edition), McGraw-Hill, 1995; and the Merck Index on CD-ROM, 13$^{th}$ Edition; and on STN Express, file phar and file registry.

In some embodiments the β-adrenergic antagonists are atenolol, bisoprolol, carvedilol, metoprolol, nebivolol, propranolol or timolol. In more particular embodiments the atenolol is administered in an amount of about 50 milligrams to about 200 milligrams as a single dose or as multiple doses per day; the bisoprolol is administered as bisoprolol fumarate in an amount of about 2.5 milligrams to about 30 milligrams as a single dose or as multiple doses per day; the carvedilol is administered in an amount of about 3.125 milligrams to about 200 milligrams as a single does or as multiple doses per day; the metoprolol is administered as metoprolol tartarate in an amount of about 50 milligrams to about 300 milligrams as a single dose or as multiple doses per day; the nebivolol is administered as nebivolol hydrochloride in an amount of about 2.5 milligrams to about 20 milligrams as a single dose or as multiple doses per day; the propranolol is administered as propranolol hydrochloride in an amount of about 40 milligrams to about 240 milligrams as a single dose or as multiple doses per day; the timolol is administered as timolol maleate in an amount of about 10 milligrams to about 30 milligrams as a single dose or as multiple doses per day.

Suitable calcium channel blockers include, but are not limited to, amlodipine (NORVASC®), anipamil, aranidipine, amrinone, azelnidipine, barnidipine, bencyclane, benidipine, bepridil, cilnidipine, cinnarizine, clentiazem, diltiazem, dotarizine, efonidipine, elgodipine, fantofarone, felodipine, fendiline, flunarizine, fluspirilene, furnidipine, gallopamil, ipenoxazone, isradipine, lacidipine, lemildipine, lercanidipine, lomerizine, manidipine, mibefradil, monatepil, nicardipine, nifedipine, niguldipine, niludipine, nilvadipine, nimodipine, nisoldipine, nitrendipine, nivaldipine, oxodipine, perhexilene, phenytoin, phenytprenylamine, pranidipine, ranolazine, ryosidine, semotiadil, tamolarizine, temiverine hydrochloride, terodiline, tiapamil, vatanidipine hydrochloride, verapamil, ziconotide, AE-0047, CAI, JTV-519, CHF-1521, L-651582, NS-7, NW-1015, RO-2933, SB-237376, SL-34.0829-08, S-312d, SD-3212, TA-993, YM-430, and the like. Suitable calcium channel blockers are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the calcium channel blockers are amlodipine, diltiazem, isradipine, nicardipine, nifedipine, nimodipine, nisoldipine, nitrendipine, verapamil.

Suitable digitals include but are not limited to digoxin and digoxitin. In some embodiments the digoxin is administered to achieve a steady state blood serum concentration of at least about 0.7 nanograms per ml to about 2.0 nanograms per ml.

Suitable diuretics include but are not limited to, thiazides (such as, for example, althiazide, bendroflumethiazide, benzclortriazide, benzhydrochlorothiazide, benzthiazide, buthiazide, chlorothiazide, cyclopenethiazide, cyclothiazide, epithiazide, ethiazide, hydrobenzthiazide, hydrochlorothiazide, hydroflumethiazide, methylclothiazide, methylcyclothiazide, penflutazide, polythiazide, teclothiazide, trichlormethiazide, triflumethazide, and the like); alilusem, ambuside, amiloride, aminometradine, azosemide, bemetizide, bumetanide, butazolamide, butizide, canrenone, carperitide, chloraminophenamide, chlorazanil, chlormerodrin, chlorthalidone, cicletanide, clofenamide, clopamide, clorexolone, conivaptan, daglutril, dichlorophenamide, disulfamide, ethacrynic acid, ethoxzolamide, etozolon, fenoldopam, fenquizone, furosemide, indapamide, mebutizide, mefruside, meralluride, mercaptomerin sodium, mercumallylic acid, mersalyl, methazolamide, meticane, metolazone, mozavaptan, muzolimine, N-(5-1,3,4-thiadiazol-2-yl) acetamide, nesiritide, pamabrom, paraflutizide, piretanide, protheobromine, quinethazone, scoparius, spironolactone, theobromine, ticrynafen, torsemide, torvaptan, triamterene, tripamide, ularitide, xipamide or potassium, AT 189000, AY 31906, BG 9928, BG 9791, C 2921, DTI 0017, JDL 961, KW 3902, MCC 134, SLV 306, SR 121463, WAY 140288, ZP 120, and the like. Suitable diuretics are described more fully in the literature, such as in Goodman and Gilman, The Pharmacological Basis of Therapeutics (9th Edition), McGraw-Hill, 1995; and the Merck Index on CD-ROM, $13^{th}$ Edition; and on STN Express, file phar and file registry.

Depending on the diuretic employed, potassium may also be administered to the patient in order to optimize the fluid balance while avoiding hypokalemic alkalosis. The administration of potassium can be in the form of potassium chloride or by the daily ingestion of foods with high potassium content such as, for example, bananas or orange juice. The method of administration of these compounds is described in further detail in U.S. Pat. No. 4,868,179, the disclosure of which is incorporated by reference herein in its entirety.

In some embodiments the diuretics are amiloride, furosemide, chlorthalidone, hydrochlorothiazide or triamterene. In more particular embodiments the amiloride is administered as amiloride hydrochloride in an amount of about 5 milligrams to about 15 milligrams as a single dose or as multiple doses per day; the furosemide is administered in an amount of about 10 milligrams to about 600 milligrams as a single does or as multiple doses per day; the chlorthalidone is administered in an amount of about 15 milligrams to about 150 milligrams as a single dose or as multiple doses per day; the hydrochlorothiazide is administered in an amount of about 12.5 milligrams to about 300 milligrams as a single dose or as multiple doses per day; the triamterene is administered in an amount of about 35 milligrams to about 225 milligrams as a single dose or as multiple doses per day.

Suitable endothelin antagonists include, but are not limited to, atrasentan, bosentan, darusentan, endothelin, enrasentan, sitaxsentan, sulfonamide endothelin antagonists, tezosentan, BMS 193884, BQ-123, SQ 28608, and the like. Suitable endothelin antagonists are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable hydralazine compounds include, but are not limited to, compounds having the formula:

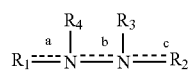

wherein a, b and c are independently a single or double bond; $R_1$ and $R_2$ are each independently a hydrogen, an alkyl, an ester or a heterocyclic ring, wherein alkyl, ester and heterocyclic rind are as defined herein; $R_3$ and $R_4$ are each independently a lone pair of electrons or a hydrogen, with the proviso that at least one of $R_1$, $R_2$, $R_3$ and $R_4$ is not a hydrogen. Exemplary hydralazine compounds include budralazine, cadralazine, dihydralazine, endralazine, hydralazine, pildralazine, todralazine, and the like. Suitable hydralazine compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the hydralazine compound is hydralazine or a pharmaceutically acceptable salt thereof such as hydralazine hydrochloride. In more particular embodiments the hydralazine is administered as hydralazine hydrochloride in an amount of about 10 milligrams to about 300 milligrams as a single dose or as multiple doses per day.

Suitable $H_2$ receptor antagonists include, but are not limited to, burimamide, cimetidine, ebrotidin, famotidine, nizatidine, roxatidine, rantidine, tiotidine, and the like. Suitable $H_2$ receptor antagonists are described more fully in the literature, such as in Goodman and Gilman, The Pharmacological Basis of Therapeutics (9th Edition), McGraw-Hill, 1995, Pgs. 901-915; the Merck Index on CD-ROM, $13^{th}$ Edition; and in WO 00/28988 assigned to NitroMed Inc., the disclosures of which are incorporated herein by reference in their entirety.

Suitable neutral endopeptidase inhibitors include, but are not limited to, atrial natriuretic peptides, diazapins, azepinones, ecadotril, fasidotril, fasidotrilat, omapatrilat, sampatrilat, BMS 189,921, Z 13752 A, and the like. Neutral endopeptidase inhibitors are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable NSAIDs include, but are not limited to, acetaminophen, acemetacin, aceclofenac, alminoprofen, amfenac, bendazac, benoxaprofen, bromfenac, bucloxic acid, butibufen, carprofen, cinmetacin, clopirac, diclofenac, etodolac, felbinac, fenclozic acid, fenbufen, fenoprofen, fentiazac, flunoxaprofen, flurbiprofen, ibufenac, ibuprofen, indomethacin, isofezolac, isoxepac, indoprofen, ketoprofen, lonazolac, loxoprofen, metiazinic acid, mofezolac, miroprofen, naproxen, oxaprozin, pirozolac, pirprofen, pranoprofen, protizinic acid, salicylamide, sulindac, suprofen, suxibuzone, tiaprofenic acid, tolmetin, xenbucin, ximoprofen, zaltoprofen, zomepirac, aspirin, acemetcin, bumadizon, carprofenac, clidanac, diflunisal, enfenamic acid, fendosal, flufenamic acid, flunixin, gentisic acid, ketorolac, meclofenamic acid, mefenamic acid, mesalamine, prodrugs thereof, and the like. Suitable NSAIDs are described more fully in the literature, such as in Goodman and Gilman, The Pharmacological Basis of Therapeutics (9th Edition), McGraw-Hill, 1995, Pgs. 617-657; the Merck Index on CD-ROM, $13^{th}$ Edition; and in U.S. Pat. Nos. 6,057,347 and 6,297,260 assigned to NitroMed Inc., the disclosures of which are incorporated herein by reference in their entirety.

In some embodiments the NSAIDs are acetaminophen, diclofenac, flurbiprofen, ibuprofen, indomethacin, ketoprofen, naproxen or aspirin. In more particular embodiments the acetaminophen is administered in an amount of about 325 milligrams to about 4 grams as a single dose or as multiple doses per day; the diclofenac is administered in an amount of about 50 milligrams to about 250 milligrams as a single does or as multiple doses per day; the flurbiprofen is administered in an amount of about 100 milligrams to about 300 milligrams as a single does or as multiple doses per day; the ibuprofen is administered in an amount of about 400 milligrams to about 3.2 grams as a single does or as multiple doses per day; the indomethacin is administered in an amount of about 25 milligrams to about 200 milligrams as a single does or as multiple doses per day; the ketoprofen is administered in an amount of about 50 milligrams to about 300 milligrams as a single does or as multiple doses per day; the naproxen is administered in an amount of about 250 milligrams to about 1.5 grams as a single does or as multiple doses per day; the aspirin is administered in an amount of about 10 milligrams to about 2 grams as a single does or as multiple doses per day.

Suitable phosphodiesterase inhibitors, include but are not limited to, filaminast, piclamilast, rolipram, Org 20241, MCI-154, roflumilast, toborinone, posicar, lixazinone, zaprinast, sildenafil, pyrazolopyrimidinones, motapizone, pimobendan, zardaverine, siguazodan, CI 930, EMD 53998, imazodan, saterinone, loprinone hydrochloride, 3-pyridinecarbonitrile derivatives, acefylline, albifylline, bamifylline, denbufyllene, diphylline, doxofylline, etofylline, torbafylline, theophylline, nanterinone, pentoxofylline, proxyphylline, cilostazol, cilostamide, MS 857, piroximone, milrinone, amrinone, tolafentrine, dipyridamole, papaveroline, E4021, thienopyrimidine derivatives, triflusal, ICOS-351, tetrahydropiperazino(1,2-b)beta-carboline-1,4-dione derivatives, carboline derivatives, 2-pyrazolin-5-one derivatives, fused pyridazine derivatives, quinazoline derivatives, anthranilic acid derivatives, imidazoquinazoline derivatives, tadalafil, vardenafil, and in Goodman and Gilman, The Pharmacological Basis of Therapeutics (9th Ed.), McGraw-Hill, Inc. (1995), The Physician's Desk Reference (49th Ed.), Medical Economics (1995), Drug Facts and Comparisons (1993 Ed), Facts and Comparisons (1993), and the Merck Index on CD-ROM, $13^{th}$ Edition; and the like. Phosphodiesterase inhibitors and their nitrosated and/or nitrosylated derivatives are also disclosed in U.S. Pat. Nos. 5,932,538, 5,994,294, 5,874,437, 5,958,926 reissued as U.S. Pat. Nos. RE 0,377,234 6,172,060, 6,197,778, 6,177,428, 6,172,068, 6,221,881, 6,232,321, 6,197,782, 6,133,272, 6,211,179, 6,316,457 and 6,331,542, the disclosures of each of which are incorporated herein by reference in their entirety.

Suitable potassium channel blockers include but are not limited to, nicorandil, pinacidil, cromakalim (BRL 34915), aprikalim, bimakalim, emakalim, lemakalim, minoxidil, diazoxide, 9-chloro-7-(2-chlorophenyl)-5H-pyrimido(5,4,-d) (2)-benzazepine, Ribi, CPG-11952, CGS-9896, ZD 6169, diazixide, Bay X 9227, P1075, Bay X 9228, SDZ PCO 400, WAY-120,491, WAY-120,129, Ro 31-6930, SR 44869, BRL 38226, S 0121, SR 46142A, CGP 42500, SR 44994, artilide fumarate, lorazepam, temazepam, rilmazafone, nimetazepam, midazolam, lormetazepam, loprazolam, ibutilide fumarate, haloxazolam, flunitrazepam, estazolam, doxefazepam, clonazepam, cinolazepam, brotizolam, and the like. Suitable potassium channel blockers are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable platelet reducing agents include but are not limited to, fibrinolytic agents such as for example, ancrod, anistreplase, bisobrin lactate, brinolase, Hageman factor (i.e. factor XII) fragments, plasminogen activators such as, for example, streptokinase, tissue plasminogen activators (TPA), urokinase, pro-Urokinase, recombinant TPA, plasmin, plasminogen, and the like; anti-coagulant agents including but are not limited to, inhibitors of factor Xa, factor TFPI, factor VIIa, factor IXc, factor Va, factor VIIIa, inhibitors of other coagulation factors, and the like; vitamin K antagonists, such as, for example, coumarin, coumarin derivatives (e.g., warfarin sodium); glycosoaminoglycans such as, for example, heparins both in unfractionated form and in low molecular weight form; ardeparin sodium, bivalirudin, bromindione, coumarin, dalteparin sodium, danaparoid sodium; dazoxiben hydrochloride, desirudin, dicumarol, efegatran sulfate, enoxaparin sodium, ifetroban, ifetroban sodium, lyapolate sodium, nafamostat mesylate, phenprocoumon, sulfatide, tinzaparin sodium, retaplase; trifenagrel, warfarin, dextrans and the like; abciximab, acadesine, anipamil, argatroban, aspirin, clopidogrel, diadenosine 5',5'''-P1,P4-tetraphosphate (Ap4A) analogs, difibrotide, dilazep dihydrochloride, dipyridamole, dopamine, 3-methoxytyramine, glucagon, glycoprotein IIb/IIIa antagonists, such as, for example, Ro-43-8857, L-700,462, iloprost, isocarbacyclin methyl ester, itazigrel, ketanserin, BM-13.177, lamifiban, lifarizine, molsidomine, nifedipine, oxagrelate, prostaglandins, platelet activating factor antagonists such as, for example, lexipafant, prostacyclins, pyrazines, pyridinol carbamate, ReoPro (i.e., abciximab), sulfinpyrazone, synthetic compounds BN-50727, BN-52021, CV-4151, E-5510, FK-409, GU-7, KB-2796, KBT-3022, KC-404, KF-4939, OP-41483, TRK-100, TA-3090, TFC-612, ZK-36374, 2,4,5,7-tetrathiaoctane, 2,4,5,7-tetrathiaoctane 2,2-dioxide, 2,4,5-trithiahexane, theophyllin pentoxifyllin, thromboxane and thromboxane synthetase inhibitors such as, for example, picotamide, sulotroban, ticlopidine, tirofiban, trapidil, ticlopidine, trifenagrel, trilinolein, 3-substituted 5,6-bis(4-methoxyphenyl)-1,2,4-triazines; antibodies to glycoprotein IIb/IIIa; anti-serotonin drugs, such as, for example, clopridogrel; sulfinpyrazone and the like; aspirin; dipyridamole; clofibrate; pyridinol carbamate; glucagon; caffeine; theophyllin pentoxifyllin; ticlopidine, and the like.

Suitable proton pump inhibitors include, but are not limited to, disulprazole, esomeprazole, lansoprazole, leminoprazole, omeprazole, pantoprazole, rabeprazole, timoprazole, tenatoprazole, 2-(2-benzimidazolyl)-pyridine, tricyclic imidazole, thienopydidine benzimidazole, fluoroalkoxy substituted benzimidazole, dialkoxy benzimidazole, N-substituted 2-(pyridylalkenesulfinyl) benzimidazole, cycloheptenepyridine, 5-pyrrolyl-2-pyridylmethylsulfinyl benzimidazole, alkylsulfinyl benzimidazole, fluoro-pyridylmethylsulfinyl benzimidazole, imidazo(4,5-b)pydridine, RO 18-5362, IY 81149, 4-amino-3-carbonyl quinoline, 4-amino-3-acylnaphthyride, 4-aminoquinoline, 4-amino-3-acylquinoline, 3-butyryl-4-(2-methylphenylamino)-8-(2-hydroxyethoxy)quinoline, quinazoline, tetrahydroisoquinolin-2-yl pyrimidine, YH 1885, 3-substituted 1,2,4-thiadiazolo (4,5-a) benzimidazole, 3-substituted imidazo(1,2-d)-thiadiazole, 2-sulfinylnicotinamide, pyridylsulfinylbenz imidazole, pyridylsulfinyl thieno imidazole, theinoimidazole-toluidine, 4,5-dihydrooxazole, thienoimidazole-toluidine, Hoe-731, imidazo(1,2-a)pyridine, pyrrolo(2,3-b)pyridine, and the like. Suitable proton pump inhibitors are described more fully in the literature, such as in Goodman and Gilman, The Pharmacological Basis of Therapeutics (9th Edition), McGraw-Hill, 1995; the Merck Index on CD-ROM, $13^{th}$ Edition; and in WO 00/50037 assigned to NitroMed Inc., the disclosures of which are incorporated herein by reference in their entirety.

Suitable renin inhibitors include, but are not limited to, aldosterone, aliskiren (SPP-100), ditekiren, enalkrein (A-64662), medullipin, terlkiren, tonin, zankiren, RO 42-5892 (remikiren), A 62198, A 64662, A 65317, A 69729, A 72517 (zankiren), A 74273, CP 80794, CGP 29287, CGP-38560A, EMD 47942, ES 305, ES 1005, ES 8891, FK 906, FK 744, H 113, H-142, KRI 1314, pepstatin A, RO 44-9375 (ciprokiren), RO 42-5892, RO 66-1132, RO 66-1168, SP 500, SP 800, SR-43845, SQ 34017, U 71038, YM-21095, YM-26365, urea derivatives of peptides, amino acids connected by nonpeptide bonds, di- and tri-peptide derivatives (e.g., Act-A, Act-B, Act-C, ACT-D, and the like), amino acids and derivatives thereof, diol sulfonamides and sulfinyls, modified peptides, peptidyl beta-aminoacyl aminodiol carbamates, monoclonal antibodies to renin. Suitable renin inhibitors are described more fully in U.S. Pat. Nos. 5,116,835, 5,114,937, 5,106,835, 5,104,869, 5,095,119, 5,098,924), 5,095,006, 5,089,471, 5,075,451, 5,066,643, 5,063,208, 4,845,079, 5,055,466, 4,980,283, 4,885,292), 4,780,401, 5,071,837, 5,064,965, 5,063,207, 5,036,054, 5,036,053, 5,034,512, and 4,894,437, the disclosures of each of which are incorporated herein by reference in their entirety; and in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable COX-2 inhibitors include, but are not limited to, nimesulide, celecoxib (CELEBREX®), etoricoxib (ARCOXIA®), flosulide, lumiracoxib (PREXIG®, COX-189), parecoxib (DYNSTAT®), rofecoxib (VIOXX®), tiracoxib (JTE-522), valdecoxib (BEXTRA®), ABT 963, BMS 347070, CS 502, DuP 697, GW-406381, NS-386, SC-57666, SC-58125, SC-58635, and the like, and mixtures of two or more thereof. Suitable COX-2 inhibitors are in U.S. Pat. Nos. 5,344,991, 5,380,738, 5,393,790, 5,409,944, 5,434,178, 5,436,265, 5,466,823, 5,474,995, 5,510,368, 5,536,752, 5,550,142, 5,552,422, 5,604,253, 5,604,260, 5,639,780, 5,932,598 and 6,633,272, and in WO 94/03387, WO 94/15723, WO 94/20480, WO 94/26731, WO 94/27980, WO 95/00501, WO 95/15316, WO 96/03387, WO 96/03388, WO 96/06840, WO 96/21667, WO 96/31509, WO 96/36623, WO 97/14691, WO 97/16435, WO 01/45703 and WO 01/87343, the disclosures of each of which are incorporated herein by reference in their entirety; and in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the COX-2 inhibitors are celecoxib, etoracoxib, lumiracoxib, paracoxib, rofecoxib or valdecoxib. In more particular embodiments the celecoxib is administered in an amount of about 100 milligrams to about 800 milligrams as a single dose or as multiple doses per day; the etoricoxib is administered in an amount of about 50 milligrams to about 200 milligrams as a single does or as multiple doses per day; the lumiracoxib is administered in an amount of about 40 milligrams to about 1200 milligrams as a single does or as multiple doses per day; the paracoxib is administered in an amount of about 20 milligrams to about 100 milligrams as a single does or as multiple doses per day; the rofecoxib is administered in an amount of about 12.5 milligrams to about 50 milligrams as a single does or as multiple doses per day; the valdecoxib is administered in an amount of about 10 milligrams to about 40 milligrams as a single does or as multiple doses per day.

The invention provides compositions comprising (i) a nitrosated and/or nitrosylated diuretic compound of the invention or pharmaceutically acceptable salt thereof, and (ii) at least one compound selected from the group consisting of aldosterone antagonists, angiotensin II antagonists, angiotensin-converting enzyme (ACE) inhibitors, β-adrenergic antagonists, diuretics, and hydralazine compounds in one or more pharmaceutically acceptable carriers. In other embodiments of the invention the aldosterone antagonist is eplerenone or spironolactone; the angiotensin II antagonist is candesartan cilexetil, eprosartan mesylate, irbesartan, losartan potassium, medoxomil, telmisartan, trandolapril, trandolaprilat or valsartan; the angiotensin-converting enzyme inhibitor is benazepril hydrochloride, captopril, enalapril maleate, fosinopril sodium, lisinopril, moexipril hydrochloride, quinapril hydrochloride; the β-adrenergic antagonist is bisoprolol fumarate, carvedilol, metoprolol tartrate, propranolol hydrochloride or timolol maleate; the diuretic is amiloride hydrochloride, chlorthalidone, hydrochlorothiazide or triamterene; and the hydralazine compound is hydralazine hydrochloride.

The invention provides methods for treating conditions resulting from excess water and/or electrolyte retention by administering to the patient in need thereof a therapeutically effective amount of the compounds and/or compositions described herein. For example, the patient can be administered a therapeutically effective amount of at least one nitrosated and/or nitrosylated diuretic compound. In another embodiment, the patient can be administered a therapeutically effective amount of at least diuretic compound, that is optionally nitrosated and/or nitrosylated, and at least one nitric oxide donor compound. In yet another embodiment, the patient can be administered a therapeutically effective amount of at least one diuretic compound, that is optionally nitrosated and/or nitrosylated, and, at least one therapeutic agent, including but not limited to, such as, for example, aldosterone antagonists, alpha-adrenergic receptor antagonists, angiotensin II antagonists, angiotensin-converting enzyme (ACE) inhibitors, antidiabetic compounds, antihyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. In another embodiment, the patient can be administered a therapeutically effective amount of at least one diuretic compound, that is optionally nitrosated and/or nitrosylated, and, at least one therapeutic agent, and, at least one nitric oxide donor compound. In one embodiment the condition resulting from excess water and/or electrolyte retention is lower extremity swelling, fatigue, body fluid retention, cardiac enlargement, shortness of breath, and edema. The diuretic compounds, that are optionally nitrosated and/or nitrosylated, nitric oxide donors, and/or therapeutic agents can be administered separately or as components of the same composition in one or more pharmaceutically acceptable carriers.

The invention provides methods for treating cardiovascular disorders by administering to the patient in need thereof a therapeutically effective amount of the compounds and/or compositions described herein. For example, the patient can be administered a therapeutically effective amount of at least one nitrosated and/or nitrosylated diuretic compound. In another embodiment, the patient can be administered a therapeutically effective amount of at least diuretic compound, that is optionally nitrosated and/or nitrosylated, and at least one nitric oxide donor compound. In yet another embodiment, the patient can be administered a therapeutically effective amount of at least one diuretic compound, that is optionally nitrosated and/or nitrosylated, and, at least one therapeutic agent, including but not limited to, such as, for example, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. In another embodiment, the patient can be administered a therapeutically effective amount of at least one diuretic compound, that is optionally nitrosated and/or nitrosylated, and, at least one therapeutic agent, and, at least one nitric oxide donor compound. In one embodiment the cardiovascular disorder is hypertension, congestive heart failure and/or diastolic dysfunction. The diuretic compounds, that are optionally nitrosated and/or nitrosylated, nitric oxide donors, and/or therapeutic agents can be administered separately or as components of the same composition in one or more pharmaceutically acceptable carriers.

The invention provides methods for treating renovascular diseases by administering to the patient in need thereof a therapeutically effective amount of the compounds and/or compositions described herein. For example, the patient can be administered a therapeutically effective amount of at least one nitrosated and/or nitrosylated diuretic compound. In another embodiment, the patient can be administered a therapeutically effective amount of at least diuretic compound, that is optionally nitrosated and/or nitrosylated, and at least one nitric oxide donor compound. In yet another embodiment, the patient can be administered a therapeutically effective amount of at least one diuretic compound, that is optionally nitrosated and/or nitrosylated, and, at least one therapeutic agent, including but not limited to, such as, for example, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. In another embodiment, the patient can be administered a therapeutically effective amount of at least one diuretic compound, that is optionally nitrosated and/or nitrosylated, and, at least one therapeutic agent, and, at least one nitric oxide donor compound. In one embodiment the renovascular disease is renal failure or renal insufficiency. The diuretic compounds, that are optionally nitrosated and/or nitrosylated, nitric oxide donors, and/or therapeutic agents can be administered separately or as components of the same composition in one or more pharmaceutically acceptable carriers.

The invention provides methods for treating diabetes; treating diseases resulting from oxidative stress; treating endothelial dysfunctions; treating diseases caused by endothelial dysfunctions; treating cirrhosis; treating pre-eclampsia; treating osteoporosis; and treating nephropathy by administering to the patient in need thereof a therapeutically effective amount of the compounds and/or compositions described herein. For example, the patient can be administered a therapeutically effective amount of at least one nitrosated and/or nitrosylated diuretic compound. In another embodiment, the patient can be administered a therapeutically effective amount of at least diuretic compound, that is optionally nitrosated and/or nitrosylated, and at least one nitric oxide donor compound. In yet another embodiment, the patient can be administered a therapeutically effective amount of at least one diuretic compound, that is optionally nitrosated and/or nitrosylated, and, at least one therapeutic agent, including but not limited to, such as, for example, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. In another embodiment, the patient can be administered a therapeutically effective amount of at least one diuretic compound, that is optionally nitrosated and/or nitrosylated, and, at least one therapeutic agent, and, at least one nitric oxide donor compound. The diuretic compounds, that are optionally nitrosated and/or nitrosylated, nitric oxide donors, and/or therapeutic agents can be administered separately or as components of the same composition in one or more pharmaceutically acceptable carriers.

Another embodiment of the invention describes methods for (a) treating conditions resulting from excessive water and/or electrolyte retention; (b) treating cardiovascular diseases; (c) treating renovascular diseases; (d) treating diabetes; (e) treating diseases resulting from oxidative stress; (f) treating endothelial dysfunctions; (g) treating diseases caused by endothelial dysfunctions; (h) treating cirrhosis; (j) treating pre-eclampsia; (k) treating osteoporosis; and (l) treating nephropathy by administering to the patient in need thereof a therapeutically effective amount of at least one nitrosated diuretic compound of Formula (VII) or pharmaceutically acceptable salts thereof, wherein the compound of Formula (VII) is:

$$A\text{-}X\text{—}NO_2 \qquad (VII)$$

wherein:

$A = R(COX)_t$;

t is an integer 0 or 1;

$X = $ oxygen, NH or $NR_{1C}$;

$R_{1C}$ is a linear or branched alkyl having from $C_1$ to $C_{10}$ atoms;

when t=1 in A=R(COX)$_r$; R is selected from the group consisting of V Ad1 (bumetanide), V Ad2 (ticrynafen), V Ad3 (ethacrynic acid) and V Ad4 (piretanide):

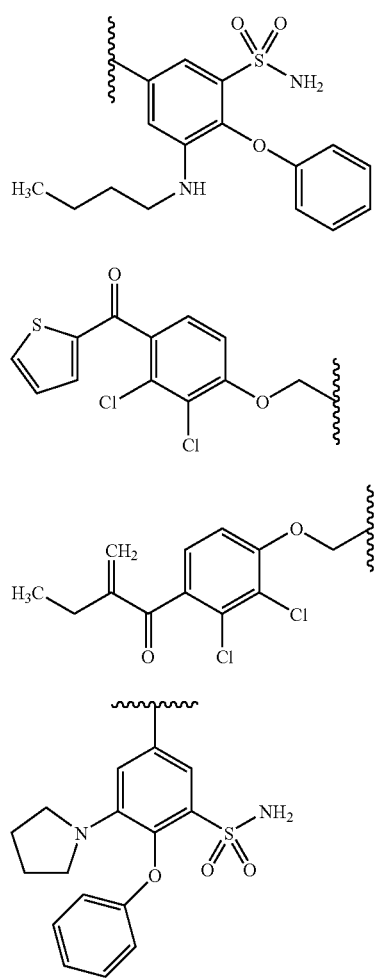

when t=0 in A=R(COX)$_r$; A=R(COX)$_r$; R is selected from the group consisting of V Ae1 (tripamide), V Ae2 (torsemide), V Ae3 (azosemide), V Ae4 (bendroflumethiazide), V Ae5 (chlorothiazide), V Ae6 (hydrochlorotiazide), V Ae7 (methyclothiazide), V Ae8 (chlorthalidone), V Ae8 (indapamide), V Ae10 (metolazone), V Ae11 (quinetazone) and V Ae12 (furosemide):

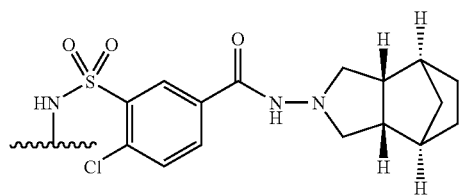

-continued

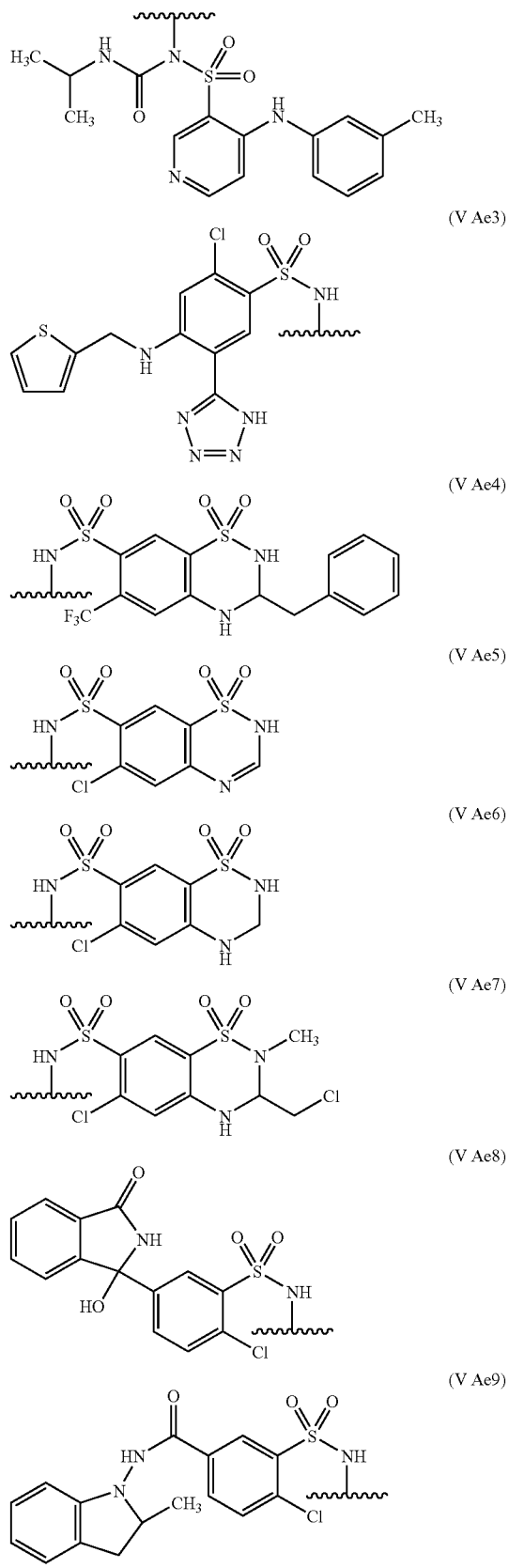

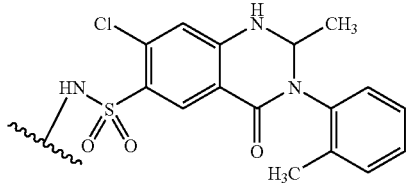 (V Ae10)

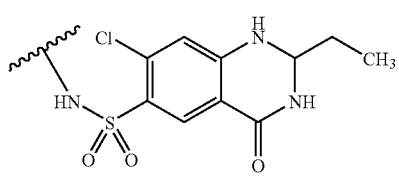 (V Ae11)

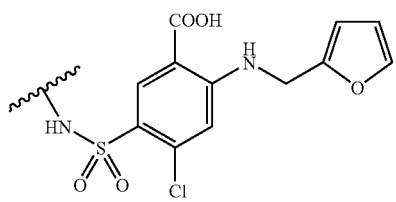 (V Ae12)

$X_1$ in formula $A-X_1-NO_2$, is a bivalent connecting bridge selected from the following:

—Y"O    (i)

wherein Y" is a linear or whenever possible branched $C_1$-$C_{20}$ alkylene, preferably having 2 to 5 carbon atoms or an optionally substituted cycloalkylene having from 5 to 7 carbon atoms;

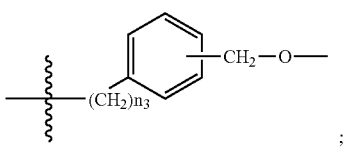 (ii)

wherein $n_3$ is an integer from 0 to 3:

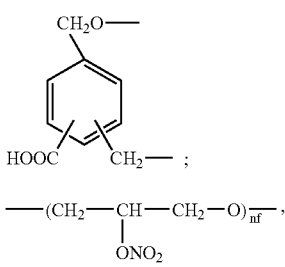 (iii)

—(CH$_2$—CH—CH$_2$—O)$\overline{nf}$—,   (iv)
       |
       ONO$_2$ wherein nf is an integer from 1 to 6, preferably an integer from 2 to 4;

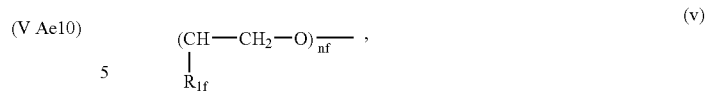 (v)

wherein $R_{1f}$ is a hydrogen or a methyl group; and
nf is as defined herein.

In this embodiment the nitrosated diuretic compound of Formula (VI) can be also administered in combination with a nitric oxide donor compound and/or a therapeutic agent. For example, the patient can be administered a therapeutically effective amount of at least one nitrosated diuretic compound of Formula (VI). In another embodiment, the patient can be administered a therapeutically effective amount of at least one nitrosated diuretic compound of Formula (VI) and at least one nitric oxide donor compound. In yet another embodiment, the patient can be administered a therapeutically effective amount of at least one nitrosated diuretic compound of Formula (VI), and, at least one therapeutic agent. In yet another embodiment, the patient can be administered a therapeutically effective amount of at least one nitrosated diuretic compound of Formula (VI), and, at least one nitric oxide donor compound and at least one therapeutic agent. The nitrosated diuretic compound of Formula (VI), nitric oxide donors, and/or therapeutic agents can be administered separately or as components of the same composition in one or more pharmaceutically acceptable carriers. The compounds of Formula (VI) can be prepared by methods described in WO 98/09948, the disclosure of which is incorporated herein in its entirety.

When administered separately, the diuretic compound, that is optionally nitrosated and/or nitrosylated, nitric oxide donor and/or therapeutic agent can be administered about the same time as part of the overall treatment regimen, i.e., as a combination therapy. "About the same time" includes administering the diuretic compound, that is optionally nitrosated and/or nitrosylated, simultaneously, sequentially, at the same time, at different times on the same day, or on different days, as long as they are administered as part of an overall treatment regimen, i.e., combination therapy or a therapeutic cocktail.

When administered in vivo, the compounds and compositions of the invention can be administered in combination with pharmaceutically acceptable carriers and in dosages described herein. When the compounds and compositions of the invention are administered as a combination of at least one diuretic compound and/or at least one nitrosated and/or nitrosylated diuretic compound and/or at least one nitric oxide donor and/or therapeutic agent, they can also be used in combination with one or more additional compounds which are known to be effective against the specific disease state targeted for treatment. The nitric oxide donors, therapeutic agents and/or other additional compounds can be administered simultaneously with, subsequently to, or prior to administration of the nitrosated and/or nitrosylated diuretic compound.

The compounds and compositions of the invention can be administered by any available and effective delivery system including, but not limited to, orally, bucally, parenterally, by inhalation, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrastemal injection, or infusion techniques. In one embodiment of the invention the nitrosated and/or nitrosylated diuretic compound is administered orally, parentally or by inhalation.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

The compositions can also be applied topically using a transdermal system, such as one of an acrylic-based polymer adhesive with a resinous crosslinking agent impregnated with the composition and laminated to an impermeable backing. In a particular embodiment, the compositions of the invention are administered as a transdermal patch, more particularly as a sustained-release transdermal patch. The transdermal patches of the invention can include any conventional form such as, for example, adhesive matrix, polymeric matrix, reservoir patch, matrix or monolithic-type laminated structure, and are generally comprised of one or more backing layers, adhesives, penetration enhancers, an optional rate controlling membrane and a release liner which is removed to expose the adhesives prior to application. Polymeric matrix patches also comprise a polymeric-matrix forming material. Suitable transdermal patches are described in more detail in, for example, U.S. Pat. Nos. 5,262,165, 5,948,433, 6,010,715 and 6,071,531, the disclosure of each of which are incorporated herein in their entirety.

Solid dosage forms for oral administration can include capsules, sustained-release capsules, tablets, sustained release tablets, chewable tablets, sublingual tablets, effervescent tablets, pills, powders, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention, such as for treating pediatric fever and the like, can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

The bioavailability of the compositions can be enhanced by micronization of the formulations using conventional techniques such as grinding, milling, spray drying and the like in the presence of suitable excipients or agents such as phospholipids or surfactants.

Sustained release dosage forms of the invention may comprise microparticles and/or nanoparticles having a therapeutic agent dispersed therein or may comprise the therapeutic agent in pure, preferably crystalline, solid form. For sustained release administration, microparticle dosage forms comprising pure, preferably crystalline, therapeutic agents are preferred. The therapeutic dosage forms of this aspect of the invention may be of any configuration suitable for sustained release.

Nanoparticle sustained release therapeutic dosage forms are preferably biodegradable and, optionally, bind to the vascular smooth muscle cells and enter those cells, primarily by endocytosis. The biodegradation of the nanoparticles occurs over time (e.g., 30 to 120 days; or 10 to 21 days) in prelysosomic vesicles and lysosomes. Preferred larger microparticle therapeutic dosage forms of the invention release the therapeutic agents for subsequent target cell uptake with only a few of the smaller microparticles entering the cell by phagocytosis. A practitioner in the art will appreciate that the precise mechanism by which a target cell assimilates and metabolizes a dosage form of the invention depends on the morphology, physiology and metabolic processes of those cells. The size of the particle sustained release therapeutic dosage forms is also important with respect to the mode of cellular assimilation. For example, the smaller nanoparticles can flow with the interstitial fluid between cells and penetrate the infused tissue. The larger microparticles tend to be more easily trapped interstitially in the infused primary tissue, and thus are useful to deliver anti-proliferative therapeutic agents.

Particular sustained release dosage forms of the invention comprise biodegradable microparticles or nanoparticles. More particularly, biodegradable microparticles or nanoparticles are formed of a polymer containing matrix that biodegrades by random, nonenzymatic, hydrolytic scissioning to release therapeutic agent, thereby forming pores within the particulate structure.

In a particular embodiment, the compositions of the invention are orally administered as a sustained release tablet or a sustained release capsule. For example, the sustained release formulations can comprise a therapeutically effective amount of at least one nitrosated and/or nitrosylated diuretic compound or a pharmaceutically acceptable salt thereof, and, optionally at least one nitric oxide donor, or the sustained release formulations can comprise a therapeutically effective amount of at least one nitrosated and/or nitrosylated diuretic compound or a pharmaceutically acceptable salt thereof, and at least one nitric oxide donor, and, optionally at least one therapeutic agent The compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound. In one embodiment, the pharmaceutically acceptable salts of the compounds of the invention do not include the nitrate salt.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given nitrosated and/or nitrosylated diuretic compound of the invention that will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The invention also provides pharmaceutical kits comprising one or more containers filled with one or more of the ingredients of the pharmaceutical compounds and/or compositions of the invention, including, at least, one or more of the novel diuretic compound, that is optionally nitrosated and/or nitrosylated, and one or more of the NO donors described herein. Associated with such kits can be additional

EXAMPLES

Example 1

(N-(2-(Nitrooxy)ethyl)carbamoyl)methyl 4-chloro-2-((2-furylmethyl)amino)-5-sulfamoylbenzoate 1a. Ethyl 2-(4-chloro-6-((2-furylmethyl)amino)-3-sulfamoylphenylcarbonyloxy)-acetate

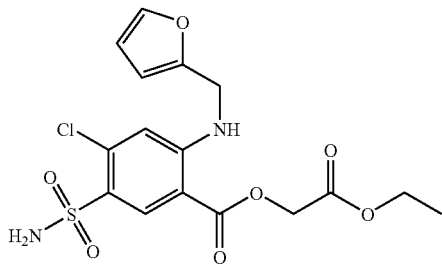

A mixture of furosemide (ONBIO Inc., 20 g, 60.5 mmol), $K_2CO_3$ (8.3 g, 60.5 mmol) and ethyl bromoacetate (10.1 g, 6.7 mL, 60.5 mmol) in dry acetone (400 mL) was stirred at room temperature for 16 hours. The solvent was evaporated at reduced pressure. The residue was diluted with $CH_2Cl_2$, the solid $K_2CO_3$ was removed by filtration. The filtrate was washed with water, brine and dried over $Na_2SO_4$. The residue obtained after evaporation of the solvent was dried under vacuum to give the title compound (23.5 g, 93% yield) as a white foam. Mp 46° C. $^1$H NMR (300 MHz, $d_6$-DMSO) δ 8.48 (s, 1H), 8.37 (br t, J=5.6 Hz, 1H), 7.62 (s, 1H), 7.39 (br s, 2H), 7.14 (s, 1H), 6.37-6.43 (m, 2H), 4.93 (s, 2H), 4.62 (br d, J=5.7 Hz, 2H), 4.17 (q, J=7.0 Hz, 2H), 1.19 (br t, J=14.1 Hz, 3H). $^{13}$C NMR (75 MHz, $d_6$-DMSO) δ 167.6, 165.8, 152.2, 151.1, 142.8, 137.0, 133.0, 127.1, 114.1, 110.5, 107.7, 106.3, 61.2, 61.0, 14.0. Mass spectrum (API-TIS) m/z 417 (MH$^+$), 434 (MNH$_4^+$). Anal. calcd for $C_{16}H_{17}ClN_2O_7S$: C, 46.10; H, 4.11; N, 6.72. Found: C, 46.13; H, 3.97; N, 6.47.

1b. 2-(4-Chloro-6-((2-furylmethyl)amino)-3-sulfamoylphenylcarbonyloxy)acetic acid

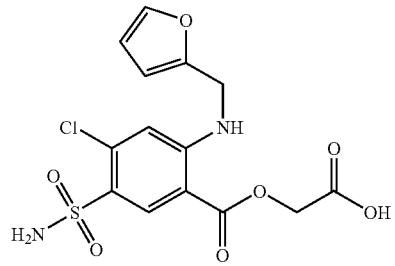

A mixture of lithium hydroxide (1.78 g, 74.5 mmol), the product of Example 1a (23 g, 55.2 mmol) in tetrahydrofuran (120 mL) and water (23 mL) was stirred at room temperature for 16 hours. The residue obtained after evaporation of the solvent was dissolved in water and washed with EtOAc. The aqueous layer was acidified with 10% citric acid (pH~5), extracted with EtOAc and the combined organic extracts were dried over $Na_2SO_4$. The residue after filtration and evaporation was chromatographed on silica gel eluting with $CH_2Cl_2$:EtOAc:MeOH (1:1:0.1) to give the title compound (15 g, 70% yield) as a white solid. Mp 228-230° C. (with decomposition). $^1$H NMR (300 MHz, $d_6$-DMSO) δ 9.68 (br s, 1H), 8.87 (br t, 1H), 8.36 (s, 1H), 7.61 (s, 1H), 7.34 (br s, 2H), 7.03 (s, 1H), 6.36-6.41 (m, 2H), 4.56 (d, J=5.5 Hz, 2H), 4.44 (br s, 2H). $^{13}$C NMR (75 MHz, $d_6$-DMSO) δ 169.6, 166.3, 151.7, 151.4, 142.6, 135.9, 132.9, 126.7, 113.5, 110.5, 109.2, 107.6, 64.1. Mass spectrum (API-TIS) m/z 387 (M−H), 389 (MH$^+$), 411 (MNa$^+$).

1c. (N-(2-(Nitrooxy)ethyl)carbamoyl)methyl 4-chloro-2-((2-furylmethyl)amino)-5-sulfamoylbenzoate

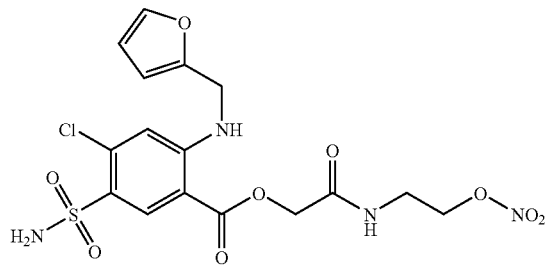

A mixture of the product of Example 1b (0.75 g, 1.9 mmol), 2-(nitrooxy)ethylammonium nitrate (prepared as described in Example 22a in US 2004/0024057; WO 2004/004648) (0.65 g, 3.85 mmol) and N,N-dimethylaminopyridine (DMAP, 0.47 g, 3.85 mmol) in $CH_2Cl_2$ (14 mL) at 0° C. was treated with 1-(3-(dimethylamino)propyl)-3-ethylcarbodiimide hydrochloride (0.37 g, 1.93 mmol). The reaction mixture was stirred at 0° C. for 4 hours, diluted with $CH_2Cl_2$, washed with water, brine and dried over $Na_2SO_4$. The residue after filtration and evaporation was chromatographed on silica gel eluting with $CH_2Cl_2$:EtOAc (1:1) to $CH_2Cl_2$:EtOAc:MeOH (1:1:0.1) to give the title compound (0.3 g, 33% yield) as a white solid. Mp 135° C. $^1$H NMR (300 MHz, $d_6$-DMSO) δ 8.47 (s, 1H), 8.36-8.44 (m, 2H), 7.62 (s, 1H), 7.37 (br s, 2H), 7.12 (s, 1H), 6.36-6.43 (m, 2H), 4.74 (s, 2H), 4.61 (d, J=5.8 Hz, 2H), 4.54 (t, J=5.1 Hz, 2H), 3.43-3.49 (m, 2H). $^{13}$C NMR (75 MHz, $d_6$-DMSO) δ 167.1, 165.9, 152.1, 151.1, 142.7, 136.8, 133.2, 127.0, 113.9, 110.5, 107.7, 106.8, 72.2, 62.6, 35.9. Mass spectrum (API-TIS) m/z 475 (M−H), 477 (MH⁺), 494 (MNH₄⁺). Anal. calcd for $C_{16}H_{17}ClN_4O_9S$: C, 40.30; H, 3.59; N, 11.75. Found: C, 40.15; H, 3.34; N, 11.78.

Example 2

(N-Methyl-N-(2-(nitrooxy)ethyl)carbamoyl)methyl 4-chloro-2-((2-furylmethyl)amino)-5-sulfamoylbenzoate

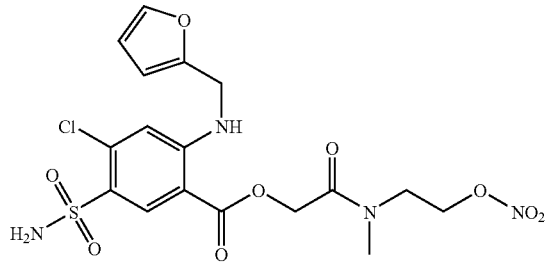

A mixture of the product of Example 1b (0.75 g, 1.9 mmol), methyl (2-(nitrooxy)ethyl)-ammonium nitrate (prepared as described in Example 17c in US 2004/0024057; WO 2004/004648) (0.65 g, 3.55 mmol) and N,N-dimethylaminopyridine (DMAP, 0.31 g, 2.5 mmol) in $CH_2Cl_2$ (14 mL) at 0° C. was treated with 1-(3-(dimethylamino)propyl)-3-ethylcarbodiimide hydrochloride (0.37 g, 1.9 mmol). The reaction mixture was stirred at 0° C. for 3 hours, diluted with $CH_2Cl_2$, washed with water, brine and dried over $Na_2SO_4$. The residue after filtration and evaporation was chromatographed on silica gel eluting with $CH_2Cl_2$:EtOAc (1.5:1 to 1:1) to give the title compound (0.3 g, 32% yield) as a white solid. Mp 70-72° C. $^1$H NMR (300 MHz, CDCl₃) δ 8.67 (s, 1H), 8.45 (br t, J=5.5 Hz, 1H), 7.37 (s, 1H), 6.85 (s, 1H), 6.26-6.34 (m, 2H), 5.29 (s, 2H), 4.94 (s, 2H), 4.60 (t, J=5.0 Hz, 2H), 4.42 (d, J=5.6 Hz, 2H), 3.69 (t, J=5.0 Hz, 2H), 3.09 (s, 3H). $^{13}$C NMR (75 MHz, CDCl₃) δ 167.0, 166.5, 153.0, 150.2, 142.7, 137.8, 134.5, 125.9, 113.6, 110.7, 108.1, 107.5, 71.0, 61.7, 46.3, 40.4, 35.8. Mass spectrum (API-TIS) nm/z 489 (M−H), 491 (MH⁺), 508 (MNH₄⁺). Anal. calcd for $C_{17}H_{19}ClN_4O_9S$·⅛ mol EtOAc: C, 41.88; H, 4.02; N, 11.16. Found: C, 42.06; H, 3.65; N, 10.96.

Example 3

2-(4-((Nitrooxy)methyl)piperidyl)-2-oxoethyl 4-chloro-2-((2-furylmethyl)amino)-5-sulfamoylbenzoate

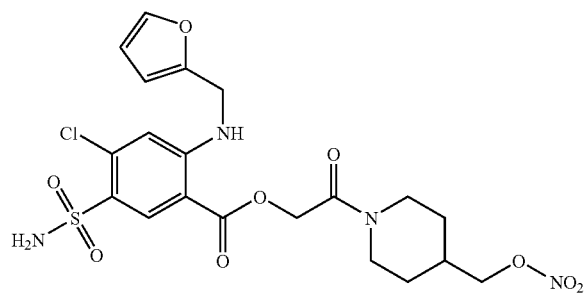

A mixture of the product of Example 1b (0.5 g, 1.29 mmol), nitrooxy(4-piperidylmethyl)-nitric acid salt (prepared as described in Example 19a in US 2004/0024057; WO 2004/004648) (0.57 g, 2.56 mmol) and N,N-dimethylaminopyridine (DMAP, 0.16 g, 1.3 mmol) in $CH_2Cl_2$ (9 mL) at 0° C. was treated with 1-(3-(dimethylamino)propyl)-3-ethylcarbodiimide hydrochloride (0.25 g, 1.3 mmol). The reaction mixture was stirred at 0° C. for 3 hours, diluted with $CH_2Cl_2$, washed with water, brine and dried over $Na_2SO_4$. The residue after filtration and evaporation was chromatographed on silica gel eluting with $CH_2Cl_2$:EtOAc (1:1) to give the title compound (0.36 g, 53% yield) as a white solid. Mp 115-117° C. $^1$H NMR (300 MHz, d₆-DMSO) δ 8.47 (s, 1H), 8.41 (br t, J=5.8 Hz, 1H), 7.61 (s, 1H), 7.36 (s, 2H), 7.12 (s, 1H), 6.37-6.43 (m, 2H), 5.08 (br s, 2H), 4.59 (d, J=5.7 Hz, 2H), 4.43 (d, J=6.4 Hz, 2H), 4.27-4.32 (m, 1H), 4.04-4.02 (m, 1H), 3.75-3.80 (m, 1H), 2.92-3.12 (m, 1H), 2.54-2.70 (m, 1H), 1.60-2.80 (m, 2H), 1.05-1.37 (m, 2H). $^{13}$C NMR (75 MHz, d₆-DMSO) δ 166.0, 164.3, 152.1, 151.2, 142.8, 136.8, 133.2, 127.1, 114.0, 110.6, 107.8, 107.2, 77.0, 62.1, 59.8, 43.3, 38.7, 33.3, 28.3, 27.6. Mass spectrum (API-TIS) m/z 529 (M−H), 531 (MH⁺), 548 (MNH₄⁺). Anal. calcd for $C_{20}H_{23}ClN_4O_9S$: C, 45.24; H, 4.37; N, 10.55. Found: C, 45.51; H, 4.41; N, 10.26.

Example 4

2-(4-(2-(Nitrooxy)ethyl)piperidyl)-2-oxoethyl 4-chloro-2-((2-furylmethyl)amino)-5-sulfamoylbenzoate

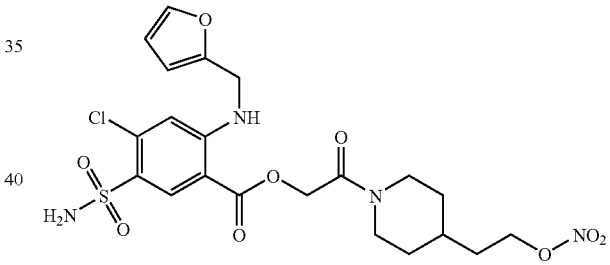

A mixture of the product of Example 1b (0.75 g, 1.9 mmol), nitrooxy(2-(4-piperidyl)ethyl)-nitric acid salt (prepared as described in Example 31a in US 2004/0024057; WO 2004/004648) (0.92 g, 3.88 mmol) and N,N-dimethylaminopyridine (DMAP, 0.24 g, 1.97 mmol) in $CH_2Cl_2$ (7 mL) and DMF (1 mL) at 0° C. was treated with 1-(3-(dimethylamino)propyl)-3-ethylcarbodiimide hydrochloride (0.44 g, 2.3 mmol). The reaction mixture was stirred at 0° C. for 1.5 hours, diluted with $CH_2Cl_2$, washed with water, brine and dried over $Na_2SO_4$. The residue after filtration and evaporation was chromatographed on silica gel eluting with $CH_2Cl_2$:EtOAc:MeOH (1:1:0.1) to give the title compound (0.48 g, 46% yield) as a white solid. Mp 170° C. $^1$H NMR (300 MHz, d₆-DMSO) δ 8.47 (s, 1H), 8.42 (br t, J=5.6 Hz, 1H), 7.62 (s, 1H), 7.36 (s, 2H), 7.11 (s, 1H), 6.36-6.42 (m, 2H), 5.06 (s, 2H), 4.52-4.68 (m, 4H), 4.15-4.30 (m, 1H), 3.67-3.83 (m, 1H), 2.90-3.10 (m, 1H), 2.50-2.70 (m, 1H), 1.50-1.82 (m, 5H), 0.80-1.30 (m, 2H). $^{13}$C NMR (75 MHz, d₆-DMSO) δ 166.0, 164.1, 152.0, 151.1, 142.7, 136.7, 133.1, 127.0, 113.9, 110.5, 107.7, 107.2, 71.7, 62.1, 43.7, 41.4, 32.2, 32.1, 31.6, 31.0. Mass spectrum (API-TIS) m/z 545 (MH⁺), 562 (MNH₄⁺). Anal. calcd for $C_{21}H_{25}ClN_4O_9S$·0.75 mol $H_2O$: C, 45.16; H, 4.78; N, 10.03. Found: C, 44.84; H, 4.31; N, 9.90.

Example 5

2-(4-(2-(Nitrooxy)ethyl)piperazinyl)-2-oxoethyl 4-chloro-2-((2-furylmethyl)amino)-5-sulfamoylbenzoate

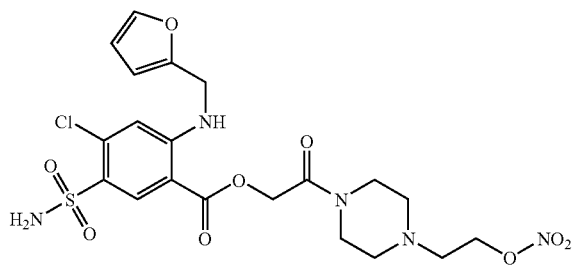

A mixture of the product of Example 1b (1 g, 2.58 mmol), nitrooxy(2-piperazinylethyl)-bis-nitric acid salt (prepared as described in Example 37a in US 2004/0024057; WO 2004/004648) (0.87 g, 2.88 mmol) and N,N-dimethylaminopyridine (DMAP, 0.89 g, 7.3 mmol) in $CH_2Cl_2$ (6 mL) and DMF (3 mL) at 0° C. was treated with 1-(3-(dimethylamino)propyl)-3-ethylcarbodiimide hydrochloride (0.49 g, 2.5 mmol). The reaction mixture was stirred at 0° C. for 2 hours, diluted with $CH_2Cl_2$, washed with water, brine and dried over $Na_2SO_4$. The residue after filtration and evaporation was chromatographed on silica gel eluting with $CH_2Cl_2$:EtOAc (1:1) to $CH_2Cl_2$:EtOAc:MeOH (1:1:0.1) to give the title compound (0.4 g, 28% yield) as a white solid. Mp 145° C. (with decomposition). $^1$H NMR (300 MHz, $d_6$-DMSO) δ 8.47 (s, 1H), 8.41 (br t, J=5.8 Hz, 1H), 7.62 (s, 1H), 7.38 (s, 2H), 7.12 (s, 1H), 6.36-6.43 (m, 2H), 5.08 (s,2H), 4.65 (t, J=5.2 Hz, 2H), 4.60 (d, J=5.8 Hz, 2H), 3.32-3.48 (m, 4H), 2.70 (t, J=5.2 Hz, 2H), 2.35-2.48 (m, 4H). $^{13}$C NMR (75 MHz, $d_6$-DMSO) δ 165.9, 152.1, 151.1, 142.8, 136.8, 133.1, 127.0, 113.9, 110.5, 107.8, 107.1, 71.7, 62.0, 53.5, 52.2, 52.1, 43.7, 41.4. Mass spectrum (API-TIS) m/z 546 (MH$^+$). Anal. calcd for $C_{20}H_{24}ClN_5O_9S$: C, 44.00; H, 4.43; N, 12.83. Found: C, 43.69; H, 4.48; N, 12.54.

Example 6

2-(4-(2-(Nitrooxy)ethyl)piperazinyl)-2-oxoethyl 4-chloro-2-((2-furylmethyl)amino)-5-sulfamoylbenzoate, hydrochloride

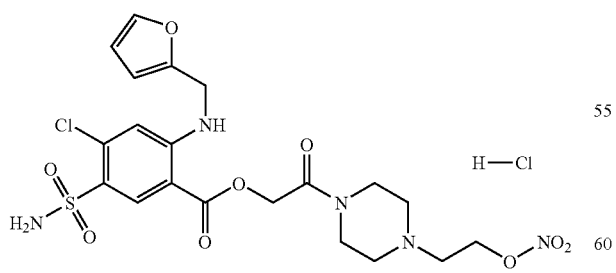

To a solution of the product of Example 5 (0.125 g, 0.23 mmol) in a mixture of $CH_2Cl_2$:EtOAc:MeOH (1:1:0.5) (5 mL) at 0° C. was added dropwise a solution of HCl gas in $Et_2O$ (0.23 mL, 8.3 mg, 1 M solution, 0.23 mmol). The cloudy solution was stirred at 0° C. for 5 minutes and hexane was added. The precipitate was filtered, washed with hexane and dried under vacuum to give the title compound (30 mg, 22% yield) as a white solid. Mp 120-125° C. (with decomposition). $^1$H NMR (300 MHz, $d_6$-DMSO) δ 10.60-10.82 (br s, 1H), 8.47 (s, 1H), 8.37 (br t, J=5.6 Hz, 1H), 7.62 (s, 1H), 7.38 (s, 2H), 7.14 (s, 1H), 6.36-6.43 (m, 2H), 5.15 (br s, 2H), 4.94 (br s, 2H), 4.61 (d, J=5.6 Hz, 2H), 3.85-4.12 (m, 4H), 3.42-3.64 (m, 2H), 2.90-3.25 (m, 4H). Mass spectrum (API-TIS) m/z 546 (MH$^+$), 568 (MNa$^+$).

Example 6a 2-(4-(2-(Nitrooxy)ethyl)piperazinyl)-2-oxoethyl 4-chloro-2-((2-furylmethyl)amino)-5-sulfamoylbenzoate, citric acid salt

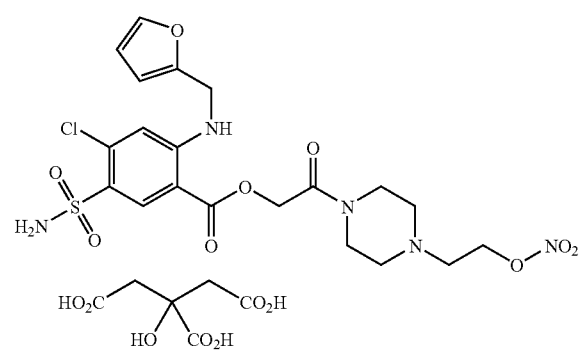

To a solution of citric acid (35.2 mg, 0.18 mmol) in MeOH (0.1 mL) at 0° C. was added dropwise a solution of the product of Example 5 (0.1 g, 0.18 mmol) in $CH_3CN$ (30 mL). The cloudy solution was stirred at 0° C. for 5 minutes, the solvent was evaporated in vacuo and hexane was added. The precipitate was filtered, washed with hexane and dried under vacuum to give the title compound (0.1 g, 74% yield) as a white solid. Mp 80-85° C. $^1$H NMR (300 MHz, $d_6$-DMSO) δ 11.40-12.80 (br s, 3H), 8.47 (s, 1H), 8.41 (br t, J=5.7 Hz, 1H), 7.62 (s, 1H), 7.38 (s, 2H), 7.12 (s, 1H), 6.36-6.42 (m, 2H), 5.08 (br s, 2H), 4.66 (t, J=5.1 Hz, 2H), 4.60 (d, J=5.6 Hz, 2H), 3.20-3.50 (m, 6H), 2.61-2.78 (m, 6H), 2.40-2.50 (m, 2H). Mass spectrum (API-TIS) m/z 545 (M–H), 546 (MH$^+$). LCMS 98.2%.

Example 7

(N-Ethyl-N-(2-(nitrooxy)ethyl)carbamoyl)methyl 4-chloro-2-((2-furylmethyl)amino)-5-sulfamoylbenzoate

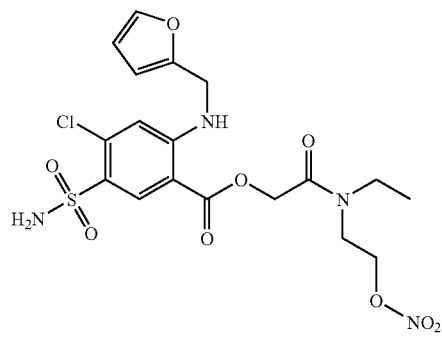

A mixture of the product of Example 1b (0.75 g, 1.9 mmol), ethyl(2-(nitrooxy)ethyl)-ammonium nitrate (prepared as described in Example 18a in US 2004/0024057; WO 2004/004648) (0.7 g, 3.8 mmol) and N,N-dimethylaminopyridine (DMAP, 0.31 g, 2.5 mmol) in $CH_2Cl_2$ (14 mL) and DMF (1 mL) at 0° C. was treated with 1-(3-(dimethylamino)propyl)-3-ethylcarbodiimide hydrochloride (0.37 g, 1.9 mmol). The reaction mixture was stirred at 0° C. for 1 hour, diluted with $CH_2Cl_2$, washed with water, brine and dried over $Na_2SO_4$. The residue after filtration and evaporation was chromatographed on silica gel eluting with $CH_2Cl_2$:EtOAc (1:1) to give the title compound (0.2 g, 20% yield) as a white solid. Mp 60-62° C. $^1$H NMR (300 MHz, $CDCl_3$) δ 8.71 (s, 1H), 8.51 (br t, J=5.4 Hz, 1H), 7.39 (s, 1H), 6.88 (s, 1H), 6.26-6.35 (m, 2H), 4.95 (br s, 4H), 4.63 (t, J=5.1 Hz, 2H), 4.44 (d, J=5.4 Hz, 2H), 3.66 (t, J=5.3 Hz, 2H), 3.30-3.55 (m, 2H), 1.26 (t, J=7.2 Hz, 3H). $^{13}$C NMR (75 MHz, $CDCl_3$) δ 166.6, 153.1, 150.2, 142.7, 137.7, 134.6, 125.9, 113.7, 110.7, 108.0, 107.6, 70.8, 61.6, 53.6, 44.0, 43.3, 40.4, 14.3. Mass spectrum (API-TIS) m/z 503 (M–H), 505 (MH$^+$), 522 (MNH$_4^+$).

Example 8

(N-((1S)-3-(Nitrooxy)-1-((nitrooxy)methyl)propyl) carbamoyl)methyl 4-chloro-2-((2-furylmethyl) amino)-5-sulfamoylbenzoate 8a. (2S)-1,4-Bis(nitrooxy)but-2-ylamine, nitric acid salt

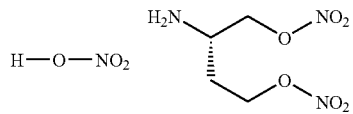

(2S)-2-Aminobutane-1,4-diol (prepared as described by Sandrin et al, U.S. Pat. No. 4,291,022) (0.3 g, 2.85 mmol) in a mixture of EtOAc (3 mL) and THF (3 mL) was added dropwise to a mixture of fuming $HNO_3$ (0.9 g, 0.6 mL, 14.2 mmol) and $Ac_2O$ (2.3 g, 2.1 mL, 22.8 mmol) at –10° C. The reaction mixture was stirred at –10° C. for 30 minutes and 0° C. for 2 hours and then diluted with EtOAc and hexane. The precipitate was collected by filtration and washed with hexane to give the title compound (0.3 g, 41% yield) as a white solid. Mp 93-95° C. $^1$H NMR (300 MHz, $d_6$-DMSO) δ 8.20 (br s, 3H), 4.61-4.81 (m, 4H), 3.55-3.75 (m, 1H), 1.90-2.15 (m, 2H). $^{13}$C NMR (75 MHz, $d_6$-DMSO) δ 72.4, 69.9, 46.2, 26.7. Mass spectrum (API-TIS) m/z 196 (MH$^+$).

8b. (N-((1S)-3-(Nitrooxy)-1-((nitrooxy)methyl)propyl)carbamoyl)methyl 4-chloro-2-((2-furylmethyl)amino)-5-sulfamoylbenzoate

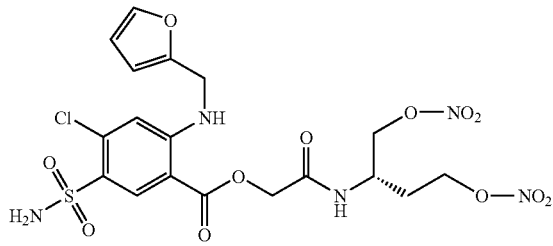

A mixture of the product of Example 1b (0.15 g, 0.39 mmol), the product of Example 8a (0.1 g, 0.39 mmol) and N,N-dimethylaminopyridine (DMAP, 47 mg, 0.39 mmol) in $CH_2Cl_2$ (7 mL) and DMF (1 mL) at 0° C. was treated with 1-(3-(dimethylamino)propyl)-3-ethylcarbodiimide hydrochloride (76 mg, 0.39 mmol). The reaction mixture was stirred at 0° C. for 1 hour and the solvent was evaporated, diluted with $CH_2Cl_2$, washed with water, brine and dried over $Na_2SO_4$. The residue after filtration and evaporation was chromatographed on silica gel eluting with $CH_2Cl_2$:EtOAc:MeOH (1:1:0.1) to give the title compound (0.1 g, 46% yield) as a white solid. Mp 115-118° C. $^1$H NMR (300 MHz, $d_6$-DMSO) δ 8.54 (s, 1H), 7.68 (s, 1H), 7.45 (s, 1H), 7.20 (s, 2H), 6.43-6.50 (m, 2H), 4.83 (s, 2H), 4.50-4.82 (m, 6H), 4.15-4.25 (m, 1H), 1.90-2.15 (m, 2H). $^{13}$C NMR (75 MHz, $d_6$-DMSO) δ 167.0, 166.0, 152.1, 151.1, 142.8, 141.0, 136.8, 127.1, 113.7, 110.5, 107.0, 106.9, 74.0, 70.3, 63.0, 43.4, 27.5. Mass spectrum (API-TIS) m/z 566 (MH$^+$), 583 (MNH$_4^+$).

Example 9

2-((2R)-2-((Nitrooxy)methyl)pyrrolidinyl)-2-oxoethyl 4-chloro-2-((2-furylmethyl)amino)-5-sulfamoylbenzoate 9a. (((2S)Pyrrolidin-2-yl)methyl)nitrooxy nitric acid salt

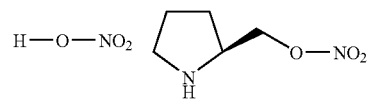

L-Prolinol (10 g, 98.9 mmol) in EtOAc (100 mL) was added dropwise to a mixture of fuming $HNO_3$ (31.2 g, 20.8 mL, 0.49 mol) and $Ac_2O$ (80.7 g, 75 mL, 0.79 mol) at –10° C. The reaction mixture was stirred at –10° C. for 30 minutes and then diluted with hexane. The precipitate was collected by filtration and washed with hexane to give the title compound (12 g, 58% yield) as a white solid. Mp 75-77° C. $^1$H NMR (300 MHz, $d_6$-DMSO) δ 8.80-9.45 (br s, 2H), 4.62-4.92 (m, 2H), 3.80-3.98 (m, 1H), 3.15-3.37 (m, 2H), 1.60-2.20 (m, 4H). $^{13}$C NMR (75 MHz, $d_6$-DMSO) δ 71.7, 55.9, 45.6, 26.4, 23.3. Mass spectrum (API-TIS) m/z 147 (MH$^+$).

9b. 2-((2R)-2-((Nitrooxy)methyl)pyrrolidinyl)-2-oxoethyl 4-chloro-2-((2-furylmethyl) amino)-5-sulfamoylbenzoate

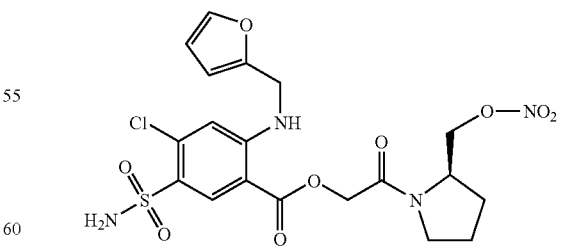

A mixture of the product of Example 1b (0.75 g, 1.9 mmol), the product of Example 9a (0.8 g, 3.8 mmol) and N,N-dimethylaminopyridine (DMAP, 0.46 g, 3.8 mmol) in $CH_2Cl_2$ (7 mL) and DMF (3 mL) at 0° C. was treated with 1-(3-(dimethylamino)propyl)-3-ethylcarbodiimide hydrochloride (0.37 g, 1.9 mmol). The reaction mixture was stirred at 0° C. for 1 hour and the solvent was evaporated, diluted with CH$_2$Cl$_2$, washed with water, brine and dried over Na$_2$SO$_4$. The residue after filtration and evaporation was chromatographed on silica gel eluting with CH$_2$Cl$_2$: EtOAc:MeOH (1:1:0.1) to give the title compound (0.35 g, 35% yield) as a white solid. Mp 64-66° C. $^1$H NMR (300 MHz, CDCl$_3$) δ 8.64 (s, 1H), 8.43 (br t, J=5.6 Hz, 1H), 7.38 (s, 1H), 6.85 (s, 1H), 6.23-6.37 (m, 2H), 5.34 (br s, 2H), 4.72-4.95 (m, 2H), 4.50-4.67 (m, 2H), 4.32-4.47 (m, 3H), 3.38-3.60 (m, 2H), 1.80-2.22 (m, 4H). $^{13}$C NMR (75 MHz, CDCl$_3$) δ 166.5, 165.9 153.1, 150.2, 142.7, 137.7, 134.6, 125.9, 113.6, 110.7, 108.1, 107.6, 72.0, 62.2, 55.2, 46.1, 40.4, 27.1, 24.5. Mass spectrum (API-TIS) m/z 517 (MH$^+$), 536 (MNH$_4^+$). Anal. calcd for C$_{19}$H$_{21}$ClN$_4$O$_9$S•0.25 mol CH$_2$Cl$_2$: C, 42.96; H, 4.02; N, 10.41. Found: C, 42.70; H, 3.72; N, 10.00.

Example 10

(N-((1R)-1-((Nitrooxy)methyl)propyl)carbamoyl) methyl4-chloro-2-((2-furylmethyl)amino)-5-sulfamoylbenzoate 10a. (2R)-1-(Nitrooxy)but-2-ylamine nitric acid salt

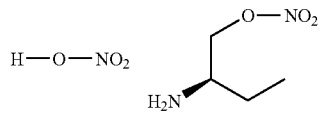

(2R)-Aminobutan-1-ol (1.01 g, 11.3 mmol) was dissolved in anhydrous acetonitrile (50 mL) and the solution was cooled using an ice bath. To the solution, fuming nitric acid (0.5 mL) was added. A mixture of acetic anhydride (8.3 mL, 90 mmol) and fuming nitric acid (2.3 mL, 57 mmol) were cooled in an ice bath and then added slowly to the aminobutan-1-ol reaction mixture and stirred for 1 hour. Solvent was removed under reduced pressure and the residue obtained was dried overnight under high vacuum to yield the title compound (2.07 g, 10.5 mmol, 93% yield) as a light green solid. $^1$H NMR (300 MHz, CDCl$_3$) δ 8.22 (s, 2H), 4.75 (dd, J=11.9 and 2.7 Hz, 1H), 4.60-4.53 (m, 1H), 3.46 (s, 1H), 1.61 (m, 2H), 0.92 (t, J=7.4 Hz, 3H). $^{13}$C NMR (CDCl$_3$, 75.45 MHz) δ 72.1, 49.7, 22.5, 9.5. LRMS (APIMS) m/z 135 (M−HNO$_3$+H)$^+$.

10b. (N-((1R)-1-((Nitrooxy)methyl)propyl)carbamoyl)methyl4-chloro-2-((2-furylmethyl)amino)-5-sulfamoylbenzoate

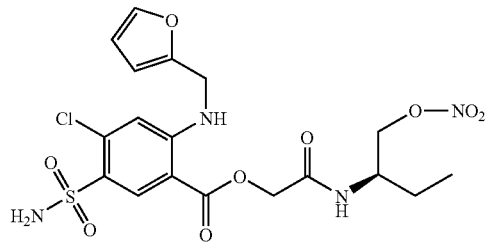

The product of Example 1b (470 mg, 1.2 mmol) was dissolved in DMSO (2 mL) and anhydrous CH$_2$Cl$_2$ (8 mL). To this solution were added successively the product of Example 10a (260 mg, 1.3 mmol), EDAC (230 mg, 1.2 mmol) and DMAP (150 mg, 1.2 mmol) and the reaction mixture was stirred overnight at room temperature under nitrogen. Additional product of Example 10a (240 mg, 1.2 mmol), EDAC (230 mg, 1.2 mmol) and DMAP (150 mg, 1.2 mmol) were added and the reaction mixture was continued stirring for 3 hours. The reaction mixture was diluted with CH$_2$Cl$_2$, washed with water (2×), brine, dried (Na$_2$SO$_4$), filtered and the solvent was removed under reduced pressure. The residue was purified by silica gel flash column chromatography using 50% ethyl acetate in hexanes to give the title compound (330 mg, 55% yield) as a white solid. Mp 125-128° C. (with decomposition). $^1$H NMR (CDCl$_3$, 300 MHz) δ 7.77 (s, 1H), 6.61 (s, 1H), 6.16 (s, 1H), 5.52 (s, 2H), 4.12-3.93 (m, 6H), 3.74 (s, 1H), 3.65 (s, 2H), 3.32 (s, 2H), 0.44 (m, 2H), 0.12 (m, 3H). $^{13}$C NMR (CDCl$_3$, 75.45 MHz) δ 170.0, 167.6, 154.0, 152.2, 143.6, 138.8, 135.0, 127.6, 114.8, 111.4, 108.7, 108.3, 75.1, 63.9, 50.0, 40.6, 24.8, 10.6.

Example 11

(N-((2S)-2-(Nitrooxy)propyl)carbamoyl)methyl4-chloro-2-((2-furylmethyl)amino)-5-sulfamoylbenzoate 11a. (2S)-2-(Nitrooxy)propylamine nitric acid salt

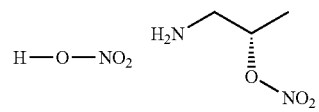

The procedure described for Example 10a was used with S-(+)-1-amino-2-propanol (960 mg, 12.8 mmol), fuming nitric acid (0.62 mL) and acetic anhydride (9.7 ml) and 2.7 mL fuming nitric acid (2.7 ml) to give the title compound as a light green solid in quantitative yield. $^1$H NMR (CDCl$_3$, 300 MHz) δ 8.08 (s, 3H), 5.32 (m, 1H), 3.24-3.06 (m, 2H), 1.34 (d, J=6.4 Hz, 3H). $^{13}$C NMR (CDCl$_3$, 75.45 MHz) δ 78.1, 40.8, 15.9. LRMS (APIMS) m/z 121 (M−HNO$_3$ +H)$^+$.

11b. (N-((2S)-2-(Nitrooxy)propyl)carbamoyl)methyl4-chloro-2-((2-furylmethyl)amino)-5-sulfamoylbenzoate

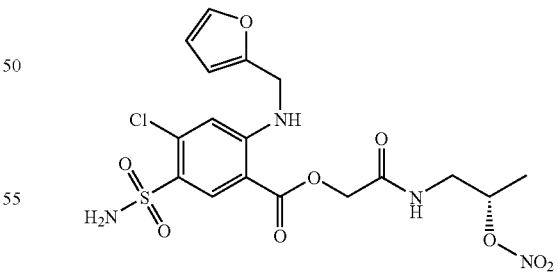

The product of Example 1b (430 mg, 1.1 mmol) was dissolved in DMSO (2 mL) and anhydrous CH$_2$Cl$_2$ (8 mL). To this solution were added successively the product of Example 11a (220 mg, 1.2 mmol), EDAC (210 mg, 1.1 mmol) and DMAP (140 mg, 1.1 mmol) and the reaction mixture was stirred overnight at room temperature under nitrogen. Additional product of Example 11a (200 mg, 1.1 mmol), EDAC (210 mg, 1.1 mmol) and DMAP (140 mg, 1.1 mmol) were added and the reaction mixture was further stirred for 6 hours. The reaction mixture was diluted with CH$_2$Cl$_2$, washed with water (2×), brine, dried (Na$_2$SO$_4$), filtered and solvent was removed under reduced pressure. The residue was purified by silica gel flash column chromatography using 50% ethyl acetate in hexanes to give the title compound (250 mg, 46% yield) as a white solid. Mp 125-138° C. with decomposition). $^1$H NMR (CDCl$_3$, 300 MHz) δ 8.61 (s, 1H), 7.49 (s, 1H), 7.02 (s, 1H), 6.34 (d, J=8.6 Hz, 2H), 5.22 (d, J=4.3 Hz, 1H), 4.84 (s, 4H), 4.75 (s, 2H), 4.50 (s, 2H), 3.60-3.54 (m, 2H), 3.41-3.31 (m, 1H), 1.31 (d, J=6.2 Hz, 3H). $^{13}$C NMR (CDCl$_3$, 75.45 MHz) δ 170.5, 167.7, 154.1, 152.3, 143.7, 138.9, 135.1, 127.8, 114.9, 111.4, 108.7, 108.4, 80.5, 63.9, 42.5, 40.7, 16.1. LRMS (APIMS) m/z 508 (M+NH$_4$)$^+$, 491 (M+H)$^+$.

Example 12

(N-((2R)-2,3-Bis(nitrooxy)propyl)carbamoyl)methyl4-chloro-2-((2-furylmethyl)amino)-5-sulfamoylbenzoate 12a. (2R)-2,3-Bis(nitrooxy)propylamine nitric acid salt

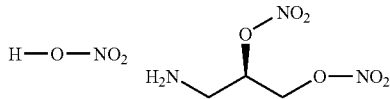

The procedure described for Example 10a was followed using (R)-3-Amino-1,2-propanediol (5.0 g, 54.9 mmol), fuming nitric acid (2.75 nmL), acetic anhydride (41.5 mL) and fuming nitric acid (11.6 mL) to give the title compound as a light green solid in quantitative yield. $^1$H NMR (CDCl$_3$, 300 MHz) δ 8.14 (s, 3H), 5.68-5.61 (m, 1H), 4.98 (dd, J=12.7, 3.3 Hz, 1H), 4.80 (dd, J=12.8, 5.3 Hz, 1H), 3.56-3.53 (m, 1H), 3.23-3.21 (m, 1H). LRMS (APIMS) m/z 182 (M−HNO$_3$+H)$^+$.

12b. (N-((2R)-2,3-Bis(nitrooxy)propyl)carbamoyl)methyl-4-chloro-2-((2-furylmethyl)amino)-5-sulfamoylbenzoate

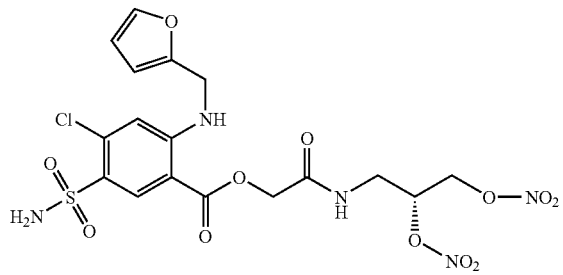

The product of Example 1b (200 mg, 0.51 mmol) was dissolved in DMSO (1 mL) and CH$_2$Cl$_2$ (10 mL). To this solution were added successively the product of Example 12a (130 mg, 0.51 mmol), triethylamine (0.07 mL, 0.51 mmol), EDAC (98 mg, 0.51 mmol), and DMAP (62 mg, 0.51 mmol) and the reaction mixture was stirred at room temperature for 3 hours under nitrogen. The reaction mixture was diluted with CH$_2$Cl$_2$, washed with water (2×), brine, dried, filtered (Na$_2$SO$_4$) and solvent was removed under reduced pressure. The residue was purified by silica gel flash column chromatography using 50% ethyl acetate in hexanes to give the title compound (90 mg, 31% yield) as a white solid. Mp 143-153° C. (with decomposition). $^1$H NMR (CDCl$_3$, 300 MHz) δ 8.16 (s, 1H), 7.96 (s, 1H), 6.57 (s, 1H), 5.86 (d, J=8.5 Hz, 2H), 5.01 (br s, 1H), 4.37 (s, 4H), 4.28 (s, 2H), 4.03 (m, 2H), 3.22-3.01 (m, 2H), 2.82 (s, 1H). LRMS (APIMS) m/z 569 (M+NH$_4$)$^+$, 552 (M+H)$^+$.

Example 13

2-Chloro-4-((2-furylmethyl)amino)-5-((4-(nitrooxy)piperidyl)carbonyl)benzenesulfonamide

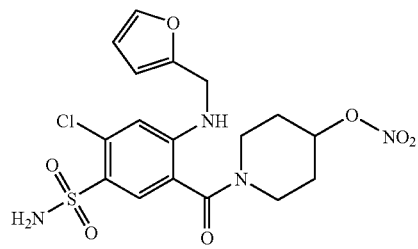

To a mixture of furosemide (331 mg, 1 mmol) and nitrooxy-4-piperidyl, nitric acid salt (prepared as described in U.S. application Ser. No. 60/505,921, Example 16a) (209 mg, 1 mmol) in ethyl acetate (25 mL) and methylsulfoxide (10 mL) was added triethyl amine (0.125 mL) and the reaction mixture was stirred at room temperature for 10 minutes. To the resulting mixture were added successively EDAC (0.192 g, 1 mmol) followed by DMAP (0.122 g, 1 mmol). The resulting solution was then stirred under nitrogen atmosphere at room temperature overnight. The reaction mixture was diluted with ethyl acetate and washed with water, aqueous NaHCO$_3$, water, brine, dried over sodium sulfate, filtered, and the organic extracts were evaporated. The product was purified by column chromatography over silica gel using 5% methanol in dichloromethane to give the title compound (390 mg, 85% yield) as colorless thick oil. $^1$H NMR (CDCl$_3$) δ 7.74(s, 1H), 7.47 (s, 1H), 6.83 (s, 1 H), 6.25-6.15 (m, 3H), 5.31 (s, 2H), 5.18 (m, 1H), 4.34 (d, J=5.2 Hz, 2H), 3.74-3.64 (m, 2 H), 3.53-3.52 (m, 2H), 2.02 (m, 2H), 1.79 (m, 2H); LRMS (APIMS) m/z 459 (MH$^+$), 441 (M−H$_2$O).

Example 14

2-((4-Chloro-6-((2-furylmethyl)amino)-3-sulfamoylphenyl)carbonylamino)ethyl (2S)-1-$^{15}$N-nitroso-pyrrolidine-2-carboxylate 14a. (2S)-1-$^{15}$N-nitroso-pyrrolidine-2-carboxylic acid

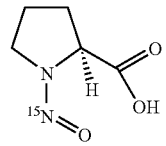

To L-proline (20.645 g, 17.932 mmol) in 2 M HCl in an ice-water bath was added sodium $^{15}$N-nitrite (1.55 g, 17.93 mmol) in water (10 mL) over a period of 10 minutes. The reaction solution was stirred at 0° C. for 20 minutes and at ambient temperature for 20 minutes, and extracted with ethyl acetate six times. The combined ethyl acetate solution was dried (magnesium sulfate), filtered, and concentrated to give the title compound (1.87 g, 72% yield). Mp 88-90° C. $^1$H NMR (300 MHz, CDCl$_3$) δ 9.98 (br s, 1 H), 5.34-5.31 (m, ⅓H), 4.55-4.41 (m, 2H), 3.71-3.68 (m, ⅔H), 2.43-2.07 (m, 4H). $^{13}$C NMR (75 MHz, CDCl$_3$) δ 161.17, 61.9, 61.8, 58.0, 50.11, 50.05, 45.8, 28.9, 27.6, 23.2, 21.1. $^{15}$N NMR (30 MHz, CDCl$_3$) δ 161.7, 154.6. LRMS (APIMS) m/z 146 (MH$^+$). LRMS (APIMS) m/z 144 (MH$^-$).

14b. (4-Chloro-6-((2-furylmethyl)amino)-3-sulfamoylphenyl)-N-(2-hydroxyethyl)carboxamide

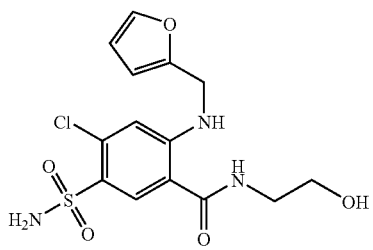

To furosemide (1.013 g, 3.0627 mmol) in DMF (3 mL) was added EDAC (608.3 mg, 3.173 mmol) in dichloromethane (3 mL) and then ethanolamine (185 μL, 3.065 mmol). The reaction solution was stirred at ambient temperature for 3 hours, and concentrated to dryness under high vacuum. The crude product was treated with water, and the resultant gum collected and chromatographed on silica gel eluting with methanol:dichloromethane (1:20) to give the title compound (476 mg, 42% yield). Mp 183-185° C. $^1$H NMR (300 MHz, CD$_3$OD) δ8.17 (s, 1H), 7.45 (m, 1H), 6.94 (s, 1H), 6.37-6.36 (m, 1 H), 6.32-6.31 (m, 1H), 4.44 (s, 2H), 3.70-3.66 (m, 2H), 3.32-3.29 (m, 2H). $^{13}$C NMR (75 MHz, CD$_3$OD) δ 170.4, 153.0, 152.7, 143.6, 136.7, 131.3, 127.5, 114.8, 114.4, 111.4, 108.5, 61.5, 43.2, 40.7. LRMS (APIMS) m/z 374(MH$^+$).

14c. 2-((4-Chloro-6-((2-furylmethyl)amino)-3-sulfamoylphenyl)carbonylamino)ethyl (2S)-1-$^{15}$N-nitroso-pyrrolidine-2-carboxylate

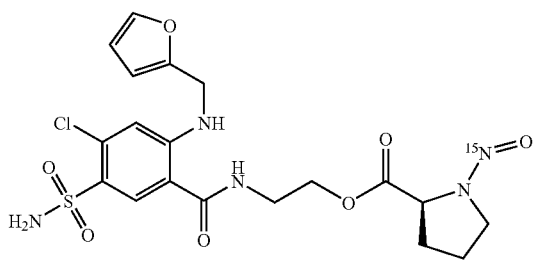

The product of Example 14a (127.6 mg, 0.880 mmol), the product of Example 14b (300.4 mg, 0.8037 mmol), EDAC (184.6 mg, 0.963 mmol), and DMAP (110.2 mg, 0.902 mmol) were mixed, and DMF-dichloromethane (1:1, 2 mL) was added. The reaction mixture was stirred at ambient temperature for 1 hour, and more of the product of Example 14a (64.2 mg, 0.443 mmol) and EDAC (82.1 mg, 0.428 mmol) were added. The resultant reaction mixture was stirred at ambient temperature for 1 hour, and concentrated to dryness under high vacuum. The resultant gum was stirred with 2 M citric acid to give a crude product. The crude product was washed with water three times and then chromatographed on silica gel eluting with methanol:chloroform (1:50) to give the title compound (250.3 mg, 62% yield). Mp 51-61° C. $^1$H NMR (300 MHz, CDCl$_3$) δ 8.11 (s, 0.4H), 8.00 (s, 0.6H), 7.38 (m, 0.6H), 7.27 (m, 0.4H), 6.78 (m, 0.6H), 6.33 (m, 0.6H), 6.27 (m, 0.4H), 5.74 (m, 0.4H), 5.30 (m, 0.6H), 5.30 (m, 0.4H), 4.52-4.29 (m, 3 H), 3.65-3.61 (m, 1H), 2.35-1.90 (m 3H). $^{13}$C NMR (75 MHz, CDCl$_3$) δ 170.4, 168.6, 168.2, 168.0, 162.6, 152.1, 152.0, 142.3, 135.3, 130.11, 129.99, 124.8, 124.7, 113.1, 112.2, 112.1, 110.4, 107.5, 63.8, 62.0, 58.5, 50.2, 45.9, 40.0, 38.4, 36.4, 31.3, 28.7, 27.5, 23.1, 21.0. $^{15}$N NMR (30 MHz, CDCl$_3$) δ 160.2, 152.7. LRMS (APIMS) m/z 501 (MH$^+$).

Example 15

2-(4-Chloro-6-((2-furylmethyl)amino)-3-sulfamoylphenylcarbonyloxy)ethyl 2-(nitrooxy)ethyl butane-1,4-dioate 15a. 3-((2-Bromoethyl)oxycarbonyl)propanoic acid

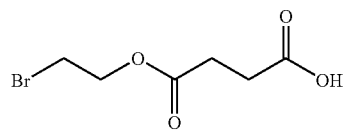

Bromoethanol (Aldrich, Wis., U.S., 1.7 mL, 24.9 mmmol), succinic anhydride (Aldrich, Wis., U.S., 1.3 g, 12.5 mmol), and N,N-dimethylaminopyridine (DMAP, 301.2 mg, 2.5 mmol) were dissolved in CHCl$_3$ (30 mL) and heated at 60° C. for 63 hours. The sample was washed with water (3×10 mL) and brine, and dried (MgSO$_4$). The solvent was removed under reduced pressure to afford the title compound (1.3 g, 48% yield) as a yellow oil which was carried on without further purification. $^1$H NMR (300 MHz, CDCl$_3$) δ 4.41 (t, J=6.1 Hz, 2H), 3.50 (t, J=6.1 Hz, 2H), 2.72-2.65 (br s, 4H). Mass Spectrum (API-TIS) m/z 225

15b. 3-((2-(Nitrooxy)ethyl)oxycarbonyl)propanoic acid

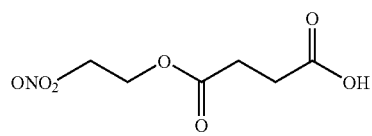

The product of Example 15a (1.3 g, 6.0 mmol) was dissolved in CH$_3$CN (30 mL) and silver nitrate (1.3 g, 7.77 mmol) was added. The mixture was stirred at 60° C. for 1.5 hours and additional silver nitrate (1.3 g, 6.0 mmol) was added. The reaction mixture was stirred at 60° C. for 24 hours. 1N HCl (10 mL) was added and the mixture stirred for 1 hour. The resulting solid was removed via filtration through Celite. The filtrate was extracted with CH$_2$Cl$_2$ (3×10 mL) and the organics collected, dried (MgSO$_4$), and the solvent removed under reduced pressure. The residue was chromatographed on silica gel eluting with 2:1 Hexanes/EtOAc to give the title compound (370.0 mg, 30% yield) as a pale yellow solid. $^1$H NMR (300 MHz, CDCl$_3$) δ 4.65-4.68 (m, 2H), 4.38-4.41 (m, 2H), 2.63-2.73 (m, 4H). Mass Spectrum (API-TIS) m/z 208 (MH$^+$).

15c. 2-Hydroxyethyl 4-chloro-2-((2-furylmethyl)amino)-5-sulfamoylbenzoate

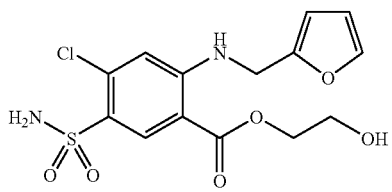

To a solution of furosemide (OnBio, Canada, 5.2 g, 15.6 mmol) in a mixture of CH$_2$Cl$_2$/DMF (15 mL /20 mL) was added ethylene glycol (Aldrich, Wis., U.S., 4.4 mL, 78.0 mmol) and DMAP (377.5 mg, 3.1 mmol). A solid formed upon the addition of the DMAP and additional DMF (15 mL) was added followed by EDAC (3.9 g, 20.3 mmol). The reaction mixture was allowed to stir at room temperature for 24 hours. The solvent was removed under reduced pressure and the residue redissolved in CH$_2$Cl$_2$ (100 mL). The sample was washed with H$_2$O (3×50 mL), brine, and the sample dried (MgSO$_4$). The residue after evaporation was chromatographed on silica gel eluting with 1:1 hexanes/EtOAc to give the title compound (1.4 g, 24% yield) as a white solid. $^1$H NMR (300 MHz, CDCl$_3$) δ 8.45-8.43 (m, 2H), 7.64 (s, 1H), 7.35 (s, 2H), 7.09 (s, 1H), 6.42-6.41 (m, 1H), 6.37-6.36 (m, 1H), 4.92 (t, J=5.4 Hz, 1H), 4.60 (d, J=5.8 Hz, 2H), 4.28 (br t, 2H), 3.71-3.65 (m, 2H). Mass Spectrum (API-TIS) m/z 375 (MH$^+$).

15d. 2-(4-Chloro-6-((2-furylmethyl)amino)-3-sulfamoylphenylcarbonyloxy)ethyl 2-(nitrooxy)ethyl butane-1,4-dioate

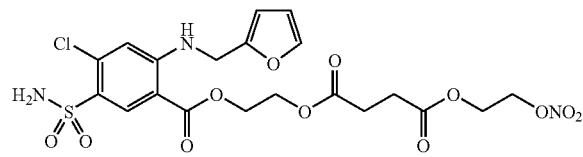

The product of Example 15c (576.1 mg, 1.5 mmol), the product of Example 15b (350.0 mg, 1.7 mmol) and DMAP (37.0 mg, 0.31 mmol) were dissolved in a CH$_2$Cl$_2$/DMF mixture (30 mL/1 mL) and EDAC (350.0 mg, 1.8 mmol) was added. The reaction mixture was stirred at room temperature for 48 hours and then at reflux for an additional 4.5 hours. The reaction mixture was washed with H$_2$O (3×10 mL), brine, and dried (MgSO$_4$) and the solvent removed under reduced pressure. The resulting residue was dissolved in MeOH and Celite was added. The solvent was removed under reduced pressure and the Celite/sample mixture chromatographed on silica gel eluting with 1:1 hexanes/EtOAc to give the title compound (180.0 mg, 21% yield) as a yellow oil. $^1$H NMR (300 MHz, CDCl$_3$) δ 8.89-8.50 (m, 1H), 8.47 (s, 1H), 7.40 (br s, 1H), 6.84 (s, 1H), 6.36-6.35 (m, 1H), 6.30-6.29 (m, 1H), 5.43 (s, 2H), 4.69-4.63 (m, 2H), 4.57-4.38 (m, 6H), 4.35-4.32 (m, 2H), 2.67 (s, 4H). Mass Spectrum (API-TIS) m/z 564 (MH$^+$).

Example 16

((2R)-1-Nitrosopyrrolidin-2-yl)methyl 4-chloro-2-((2-furylmethyl)amino)-5-sulfamoylbenzoate 16a. ((2S)-1-Nitrosopyrrolidin-2-yl)methan-1-ol

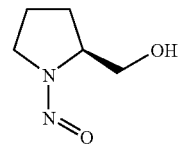

To a stirred mixture of (S)-(+)-2-pyrrolidinemethanol (6.52 g, 64.4 mmol) in THF (120 mL) and 3N hydrochloric acid (33 mL, 99 mmol) at 3° C. was added dropwise a solution of sodium nitrite (5.80 g, 84 mmol) in water (25 mL) over 20 minutes. The reaction mixture was warmed to room temperature and stirred for 15 hours. After being basified with aqueous sodium carbonate, the mixture was extracted with EtOAc twice, and the combined organic layers were dried over sodium sulfate, filtered, and concentrated. The residue was purified by column chromatography (silica gel, EtOAc) to give the title compound (8.04 g, 96% yield) as a liquid. $^1$H NMR (300 MHz, CDCl$_3$) δ 4.53-4.31 (m, 1H), 4.30-4.27 (m, 1H), 4.02-3.93 (m, 2H), 3.70-3.52 (m, 2H), 2.23-1.89 (m, 4H). $^{13}$C NMR (75 MHz, CDCl$_3$) δ 63.4, 62.6, 45.9, 26.2, 20.5, LRMS (API-TIS) m/z 131 (MH$^+$).

16b. ((2S)-1-Nitrosopyrrolidin-2-yl)methyl 4-chloro-2-((2-furylmethyl)amino)-5-sulfamoylbenzoate

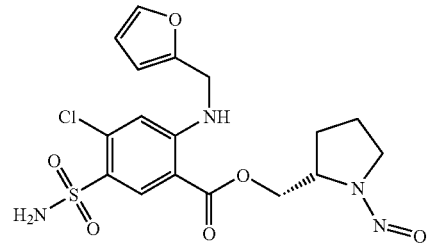

To a stirred solution of the product of Example 16a (0.78 g, 6.00 mmol), furosemide (1.80 g, 5.44 mmol), and DCC (1.24 g, 6.00 mmol) in THF (50 mL) was added DMAP (10 mg). After being stirred at ambient temperature for 18 hours, the mixture was filtered, and the filtrate was concentrated. Chromatography of the residue (1:2 EtOAc:Hex, silica gel) afforded the title compound (1.23 g, 51% yield) as a white solid. Mp 79-81° C. $^1$H NMR (300 MHz, DMSO-d$_6$) δ 8.67 (m, 1H), 8.44 (s, 1H), 7.65 (m, 1H), 7.38 (s, 2H), 7.10 (s, 1H), 6.47-6.40 (m, 2H), 4.62 (m, 2H), 4.51 (m, 1H), 3.78-3.45 (m, 4H), 2.12-1.86 (m, 4H). LRMS (API-TIS) m/z 443 and 445 (MH$^+$).

Example 17

Measurement of Urine Excretion using Furosimide and/or a Nitric Oxide Donor Compound All procedures were approved by the Institutional Animal Care and Use Committee of NitroMed Inc. Male Wistar rats (200-240 g) were purchased from Charles River Laboratories (Kingston, N.Y. or Raleigh, N.C.) and were allowed to acclimate in the facilities for a period of 72 hours. Rats were randomly housed 2-3 per cage in a light-controlled room with a 12 hour light/dark cycle and allowed ad libitum access to food and water.

Prior to the experiment, rats were singly housed in metabolic cages (Nalgene; Model MTB 0100) and allowed to acclimate for an additional period of 24 hours. During this acclimation period, the rats receive mash food instead of pellets to prevent contamination of the urine samples collected. All rats were fasted 18 hours prior to the experiment and water was removed immediately prior to intravenous administration of test compound or vehicle.

The test compounds were dissolved in a vehicle consisting of 25% dimethylethanolamine, 50% propylene glycol, and 25% $H_2O$ containing 5% glucose and were freshly prepared immediately before dosing. The suspension/solution of the test compound was gently vortexed prior to each dosing. The rats were intravenously administered either (i) vehicle alone i.e. no test compound (ii) furosemide (1 mg/kg) (iii) the nitric oxide donor compound, isosorbide dinitrate (ISDN; 1 mg/kg) or (iv) furosemide (1 mg/kg) and isosorbide dinitrate (ISDN; 1 mg/kg) as a slow bolus at a dose volume of 1 ml/kg. Urine volume (ml) was monitored over a 2-3 hour period.

As illustrated in Table I, the combination of ISDN and furosemide produced an additive effect on urine output in the rat compared to administration of either compound alone.

TABLE I

Effect of Intravenous Isosorbide Dinitrate (ISDN) and/or Furosemide on Urine Excretion in the Normal Rat.

| Treatment | Dose (mg/kg) | Total Urine Volume (ml) at: | | |
|---|---|---|---|---|
| | | 1 h | 2 h | 3 h |
| Vehicle (n = 3) | — | 0 | 1.0 ± 0.1 | 1.3 ± 1.3 |
| ISDN (n = 3) | 1 | 1.7 ± 0.9 | 3.3 ± 0.9 | 3.7 ± 0.9 |
| Furosemide (n = 3) | 1 | 3.3 ± 1.7 | 3.3 ± 1.7 | 5.0 ± 0.6 |
| ISDN + Furosemide (n = 3) | 1 1 | 5.8 ± 0.3 | 6.0 ± 0.4 | 6.8 ± 0.5 |

Example 18

Measurement of Urine Excretion using a Nitrosated Diuretic Compound

The procedure described in Example 17 was followed except the rats were intravenously administered either (i) vehicle i.e. no test compound (ii) furosemide (3 mg/kg) or (iii) Example 12 (3 mg/kg equivalent) as a slow bolus at a dose volume of 1 ml/kg.

As illustrated in Table II, the nitrosated diuretic compound, Example 12, elicits diuresis in the rat

TABLE II

Effect of Intravenous Furosemide or Example 12, on Urine Excretion in the Normal Rat

| Treatment | Dose (mg/kg) | Total Urine Volume (ml) at: | | |
|---|---|---|---|---|
| | | 0.5 h | 1 h | 2 h |
| Vehicle (n = 4) | — | 0.8 ± 0.8 | 1.5 ± 0.9 | 2.3 ± 1.1 |
| Furosemide (n = 6) | 3 | 6.7 ± 1.2 | 8.8 ± 1.2 | 11.0 ± 1.3 |
| Example 12 (n = 6) | 3 | 4.2 ± 0.4 | 5.3 ± 0.5 | 6.2 ± 0.5 |

Example 19

Measurement of Acute Renal Failure

All procedures will be approved by the Institutional Animal Care and Use Committee of NitroMed Inc. Male Wistar rats (200-240 g) will be purchased from Charles River Laboratories (Kingston, N.Y. or Raleigh, N.C.) and will be allowed to acclimate in the facilities for a period of 72 hours. Rats will be randomly housed 2-3 per cage in a light-controlled room with a 12 hour light/dark cycle and allowed ad libitum access to food and water.

Prior to the experiment, rats will be singly housed in metabolic cages (Nalgene; Model MTB 0100) and allowed to acclimate for a period of 24 hours. During this acclimation period, rats receive mash food instead of pellets to prevent contamination of the urine sarnples. All rats will be fasted 18 hours prior to the experiment and water will be removed 90 minutes before oral dosing with test compound or vehicle.

The test compounds, after being pulverized using a mortar and pestle, will be suspended in 0.5% Methocel (Dow Chemical Company, USA) and homogenized with a glass/ Teflon pestle motorized homogenizer. All test compounds will be prepared immediately before dosing and gently vortexed before each dosing. Each test compounds is administered intragastrically (p.o.) at a dose volume of 1 ml/kg or 0.3 ml/rat using an 18 gauge gavage needle.

Urine volume (ml) will be collected and recorded over a 1-24 hour period. Depending on the study a urine sample will be analyzed for urine chemistry (albumin, blood urine nitrogen (BUN), calcium, creatinine, glucose, and total protein) and electrolyte analysis (chloride, sodium, and potassium) using a VetACE Clinical Chemistry System (Alfa Wasserman; West Caldwell, N.J.). Blood will be collected from the tail vein as needed to examine blood clinical chemistry. At the termination of the study, animals will be sacrificed using pre-charged $CO_2$.

The disclosure of each patent, patent application and publication cited or described in the present specification is hereby incorporated by reference herein in its entirety.

Although the invention has been set forth in detail, one skilled in the art will appreciate that numerous changes and modifications can be made to the invention, and that such changes and modifications can be made without departing from the spirit and scope of the invention.

What is claimed is:
1. A nitrosated furosemide of Formula (VI) or a pharmaceutically acceptable salt thereof,
wherein the compound of Formula (VI) is:
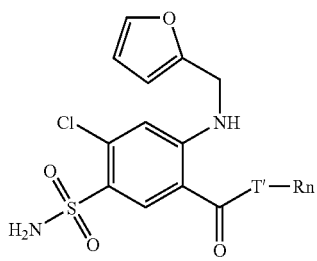
(VI)
wherein
T' is oxygen or $NR_6$;
$R_6$ is a hydrogen, a lower alkyl group, an aryl group;
$R_n$ is:
a hydrogen or
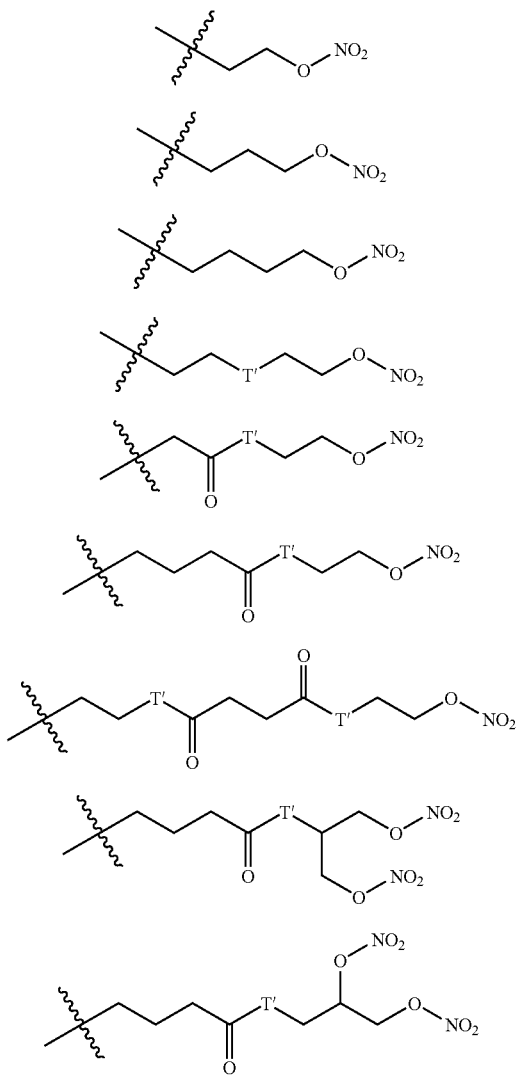
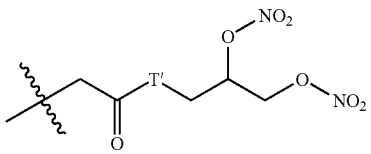
(10)
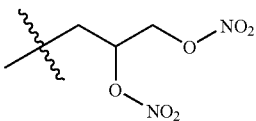
(11)
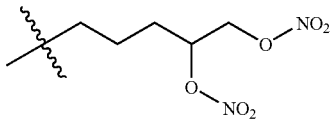
(12)
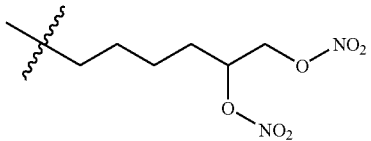
(13)
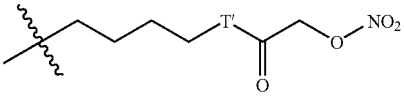
(14)
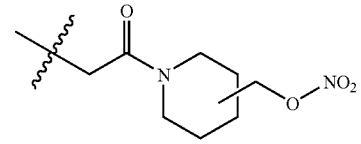
(15)
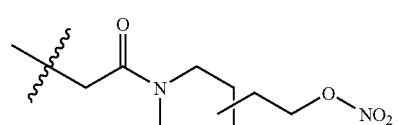
(16)
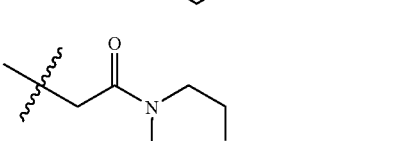
(17)
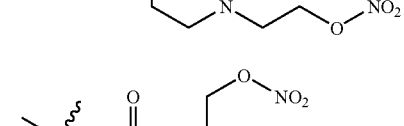
(18)
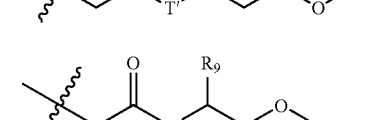
(19) or
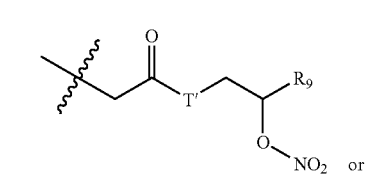
(20) or

-continued

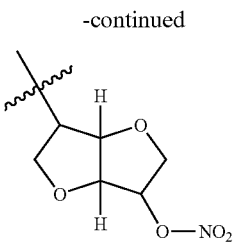

(21)

wherein:
R₉ is a lower alkyl group; and
T' is as defined herein, and T' is oxygen or NR₆;
R₆ is a hydrogen, a lower alkyl group, an aryl group; and with the proviso that the compounds of Formula (VI) must contain at least one —NO₂ group.

2. A composition comprising the compound of claim 1 and a pharmaceutically acceptable carrier.

3. The composition of claim 2, further comprising (i) at least one therapeutic agent; (ii) at least one nitric oxide donor compound; or (iii) at least one therapeutic agent and at least one nitric oxide donor compound, wherein the nitric oxide donor compound is selected from the group consisting of a S-nitrosothiol, a nitrite, a nitrate, a S-nitrothiol, a sydnonimine, a NONOate, a N-nitrosoamine, a N-hydroxyl nitrosamine, a nitrosimine, a diazetine dioxide, an oxatriazole 5-imine, an oxime, a hydroxylamine, a N-hydroxyguanidine, a hydroxvurea or a furoxan, and wherein the therapeutic agent is an aldosterone antagonist, an aipha-adrenergic receptor antagonist, an angiotensin II antagonist, an angiotensin-converting enzyme inhibitor, an antidiabetic compound, an anti-hyperlipidemic compound, an antioxidant, an antithrombotic and vasodilator compound, a β-adrenergic antagonist, a calcium channel blocker, a digitalis, a diuretic, an endothelin antagonist, a hydralazine compound, a H₂ receptor antagonist, a neutral endopeptidase inhibitor, a nonsteroidal antiinflammatory compound, a phosphodiesterase inhibitor, a potassium channel blocker, a platelet reducing agent, a proton pump inhibitor, a renin inhibitor, a selective cyclooxygenase-2 inhibitor, or a combination of two or more thereof.

4. The composition of claim 3, wherein the therapeutic agent is at least one compound selected from the group consisting of an aldosterone antagonist, an angiotensin II antagonist, an angiotensin-converting enzyme inhibitor, a β-adrenergic antagonist, a diuretic and a hydralazine compound.

5. The composition of claim 4, wherein the aldosterone antagonist is eplerenone or spironolactone; the angiotensin II antagonist is candesartan cilexetil, eprosartan mesylate, irbesartan, losartan potassium, medoxomil, telmisartan, trandolapril, trandolaprilat or valsartan; the angiotensin-converting enzyme inhibitor is benazepril hydrochloride, captopril, enalapril maleate, fosinopril sodium, lisinopril, moexipril hydrochloride, quinapril hydrochloride; the β-adrenergic antagonist is bisoprolol fumarate, carvedilol, metoprolol tartrate, propranolol hydrochloride or timolol maleate; the diuretic is amiloride hydrochloride, chlorthalidone, hydrochlorothiazide or triamterene; and the hydralazine compound is hydralazine hydrochloride.

6. A compound selected from the group consisting of:
(N-(2-(nitrooxy)ethyl)carbamoyl)methyl 4-chloro-2-((2-furylmethyl)amino)-5-sulfamoylbenzoate;
(N-methyl-N-(2-(nitrooxy)ethyl)carbamoyl)methyl 4-chloro-2-((2-furylmethyl)amino)-5-sulfamoylbenzoate;
2-(4-((nitrooxy)methyl)piperidyl)-2-oxoethyl 4-chloro-2-((2-furylmethyl)amino)-5-sulfamoylbenzoate;
2-(4-(2-(nitrooxy)ethyl)piperidyl)-2-oxoethyl 4-chloro-2-((2-furylmethyl)amino)-5-sulfamoylbenzoate;
2-(4-(2-(nitrooxy)ethyl)piperazinyl)-2-oxoethyl 4-chloro-2-((2-furylmethyl)amino)-5-sulfamoylbenzoate;
2-(4-(2-(nitrooxy)ethyl)piperazinyl)-2-oxoethyl 4-chloro-2-((2-furylmethyl)amino)-5-sulfamoylbenzoate, hydrochloride;
2-(4-(2-(nitrooxy)ethyl)piperazinyl)-2-oxoethyl 4-chloro-2-((2-furylmethyl)amino)-5-sulfamoylbenzoate, citric acid salt;
(N-ethyl-N-(2-(nitrooxy)ethyl)carbamoyl)methyl 4-chloro-2-((2-ftirylmethyl)amino)-5-sulfamoylbenzoate;
(N-((1S)-3-(nitrooxy)-1-((nitrooxy)methyl)propyl)carbamoyl)methyl 4-chloro-2-((2-furylmethyl)amino)-5-sulfamoylbenzoate;
(N-((1R)-1-((nitrooxy)methyl)propyl)carbamoyl)methyl4-chloro-2-((2-furylmethyl)amino)-5-sulfamoylbenzoate;
(N-((2S)-2-(nitrooxy)propyl)carbamoyl)methyl4-chloro-2-((2-furylmethyl)amino)-5-sulfamoylbenzoate;
(N-((2R)-2,3-bis(nitrooxy)propyl)carbamoyl)methyl4-chloro-2-((2-furylmethyl)amino)-5-sulfamoylbenzoate;
2-(4-chloro-6-((2-furylmethyl)amino)-3-sulfamoylphenylcarbonyloxy)ethyl 2-(nitrooxy)ethyl butane-1,4-dioate.

* * * * *